US010999353B2

(12) United States Patent
Florissi

(10) Patent No.: US 10,999,353 B2
(45) Date of Patent: *May 4, 2021

(54) BEACON-BASED DISTRIBUTED DATA PROCESSING PLATFORM

(71) Applicant: EMC IP Holding Company LLC, Hopkinton, MA (US)

(72) Inventor: Patricia Gomes Soares Florissi, Briarcliff Manor, NY (US)

(73) Assignee: EMC IP Holding Company LLC, Hopkinton, MA (US)

( * ) Notice: Subject to any disclaimer, the term of this patent is extended or adjusted under 35 U.S.C. 154(b) by 59 days.

This patent is subject to a terminal disclaimer.

(21) Appl. No.: 16/295,730

(22) Filed: Mar. 7, 2019

(65) Prior Publication Data
US 2019/0208004 A1    Jul. 4, 2019

Related U.S. Application Data

(63) Continuation of application No. 14/982,355, filed on Dec. 29, 2015, now Pat. No. 10,277,668.
(Continued)

(51) Int. Cl.
*G06F 15/16* (2006.01)
*H04L 29/08* (2006.01)
(Continued)

(52) U.S. Cl.
CPC .............. *H04L 67/10* (2013.01); *G06N 5/04* (2013.01); *G16B 5/00* (2019.02); *G16B 20/00* (2019.02);
(Continued)

(58) Field of Classification Search
CPC ..... H04L 67/10; H04L 47/827; H04L 43/065; H04L 47/762; H04L 47/783; H04L 47/70;
(Continued)

(56) References Cited

U.S. PATENT DOCUMENTS 6,112,225 A    8/2000 Kraft et al.
6,385,652 B1    5/2002 Brown et al.
(Continued)

FOREIGN PATENT DOCUMENTS

CN    104731595 A    6/2015

OTHER PUBLICATIONS

E.R. Ganser et al., "A Technique for Drawing Directed Graphs," IEEE Transactions on Software Engineering, Mar. 1993, pp. 214-230, vol. 19, No. 3.
(Continued)

*Primary Examiner* — Thuong Nguyen
(74) *Attorney, Agent, or Firm* — Ryan, Mason & Lewis, LLP

(57) ABSTRACT

A method comprises initiating a first application in a first one of a plurality of distributed processing nodes, and responsive to initiation of the first application, identifying a plurality of beacon entities to be contacted in conjunction with execution of at least a portion of the first application. The method also comprises, for each of at least a subset of the identified beacon entities, initiating an additional application in an additional one of the plurality of distributed processing nodes. The method further comprises aggregating processing results from the first and one or more additional processing nodes, and providing the aggregated processing results to a client. The plurality of distributed processing nodes may comprise a plurality of YARN clusters associated with respective data zones, with each of the clusters being configured to perform processing operations utilizing local data resources locally accessible within its corresponding data zone.

20 Claims, 25 Drawing Sheets

Related U.S. Application Data

(60) Provisional application No. 62/143,404, filed on Apr. 6, 2015, provisional application No. 62/143,685, filed on Apr. 6, 2015.

(51) Int. Cl.

| | | |
|---|---|---|
| *G16B 30/00* | (2019.01) | |
| *G16B 20/00* | (2019.01) | |
| *G16B 40/00* | (2019.01) | |
| *G16B 45/00* | (2019.01) | |
| *H04L 12/911* | (2013.01) | |
| *H04L 12/26* | (2006.01) | |
| *H04L 12/923* | (2013.01) | |
| *G16B 5/00* | (2019.01) | |
| *G06N 5/04* | (2006.01) | |

(52) U.S. Cl.
CPC ............ *G16B 30/00* (2019.02); *G16B 40/00* (2019.02); *G16B 45/00* (2019.02); *H04L 43/065* (2013.01); *H04L 47/70* (2013.01); *H04L 47/762* (2013.01); *H04L 47/783* (2013.01); *H04L 47/827* (2013.01)

(58) Field of Classification Search
CPC .......... G16B 5/00; G16B 30/00; G16B 20/00; G16B 40/00; G16B 45/00; G06N 5/04
USPC ................ 709/201, 208, 221, 224; 370/329; 725/25; 455/404.2
See application file for complete search history.

(56) References Cited

U.S. PATENT DOCUMENTS

| | | |
|---|---|---|
| 6,516,350 B1 | 2/2003 | Lumelsky et al. |
| 7,010,163 B1 | 3/2006 | Weiss |
| 7,499,915 B2 | 3/2009 | Chandrasekar et al. |
| 7,657,537 B1 | 2/2010 | Corbett |
| 7,934,018 B1 | 4/2011 | Lavallee et al. |
| 7,934,248 B1 | 4/2011 | Yehuda et al. |
| 7,953,843 B2 | 5/2011 | Cherkasova |
| 8,224,825 B2 | 7/2012 | Wang et al. |
| 8,392,564 B1 | 3/2013 | Czajkowski et al. |
| 8,499,331 B1 | 7/2013 | Yehuda et al. |
| 8,706,798 B1 | 4/2014 | Suchter et al. |
| 8,732,118 B1 | 5/2014 | Cole et al. |
| 8,806,061 B1 | 8/2014 | Lobo et al. |
| 8,873,836 B1 | 10/2014 | Dietrich et al. |
| 8,886,649 B2 | 11/2014 | Zhang et al. |
| 8,904,506 B1 | 12/2014 | Canavor et al. |
| 8,938,416 B1 | 1/2015 | Cole et al. |
| 9,020,802 B1 | 4/2015 | Florissi et al. |
| 9,031,992 B1 | 5/2015 | Florissi et al. |
| 9,130,832 B1 | 9/2015 | Boe et al. |
| 9,158,843 B1 | 10/2015 | Florissi et al. |
| 9,229,952 B1 | 1/2016 | Meacham et al. |
| 9,235,446 B2 | 1/2016 | Bruno et al. |
| 9,239,711 B1 | 1/2016 | Mistry |
| 9,280,361 B2 | 3/2016 | Florissi et al. |
| 9,298,613 B2 | 3/2016 | Kim et al. |
| 9,338,218 B1 | 5/2016 | Florissi et al. |
| 9,361,263 B1 | 6/2016 | Florissi et al. |
| 9,374,660 B1 | 6/2016 | Tilles |
| 9,418,085 B1 | 8/2016 | Shih et al. |
| 9,451,012 B1 | 9/2016 | Neill et al. |
| 9,489,233 B1 | 11/2016 | Florissi et al. |
| 9,538,332 B1 * | 1/2017 | Mendelson ......... H04W 40/244 |
| 9,613,124 B2 | 4/2017 | Rabinowitz et al. |
| 9,659,057 B2 | 5/2017 | Tian |
| 9,665,660 B2 | 5/2017 | Wensel |
| 9,678,497 B2 | 6/2017 | Karypis et al. |
| 9,697,262 B2 | 7/2017 | Chandramouli et al. |
| 9,747,127 B1 | 8/2017 | Florissi et al. |
| 9,747,128 B1 | 8/2017 | Vijendra et al. |
| 9,767,149 B2 | 9/2017 | Ozcan et al. |
| 9,805,170 B2 | 10/2017 | Keyes et al. |
| 9,832,068 B2 | 11/2017 | McSherry et al. |
| 9,838,410 B2 | 12/2017 | Muddu et al. |
| 9,848,041 B2 | 12/2017 | Einkauf et al. |
| 9,922,334 B1 * | 3/2018 | Rothman ............... G06Q 30/02 |
| 9,996,662 B1 | 6/2018 | Florissi et al. |
| 10,015,106 B1 | 7/2018 | Florissi et al. |
| 10,111,492 B2 | 10/2018 | Florissi et al. |
| 10,114,923 B1 | 10/2018 | Florissi et al. |
| 10,122,806 B1 | 11/2018 | Florissi et al. |
| 10,127,352 B1 | 11/2018 | Florissi et al. |
| 10,148,736 B1 | 12/2018 | Lee et al. |
| 10,250,708 B1 | 4/2019 | Carver et al. |
| 10,270,707 B1 | 4/2019 | Florissi et al. |
| 10,277,668 B1 * | 4/2019 | Florissi ................ G16B 5/00 |
| 10,311,363 B1 | 6/2019 | Florissi et al. |
| 10,331,380 B1 | 6/2019 | Florissi et al. |
| 10,348,810 B1 | 7/2019 | Florissi et al. |
| 10,374,968 B1 | 8/2019 | Duerk et al. |
| 10,404,787 B1 | 9/2019 | Florissi et al. |
| 10,425,350 B1 | 9/2019 | Florissi |
| 10,496,926 B2 | 12/2019 | Florissi et al. |
| 10,505,863 B1 | 12/2019 | Florissi et al. |
| 10,509,684 B2 | 12/2019 | Florissi et al. |
| 10,511,659 B1 | 12/2019 | Florissi et al. |
| 10,515,097 B2 | 12/2019 | Florissi et al. |
| 10,528,875 B1 | 1/2020 | Florissi et al. |
| 10,541,936 B1 | 1/2020 | Florissi |
| 10,541,938 B1 | 1/2020 | Timmerman et al. |
| 10,664,856 B2 * | 5/2020 | Robbin ................ H04W 4/80 |
| 2002/0056025 A1 | 5/2002 | Qiu et al. |
| 2002/0073167 A1 | 6/2002 | Powell et al. |
| 2002/0129123 A1 | 9/2002 | Johnson et al. |
| 2003/0005140 A1 | 1/2003 | Dekel et al. |
| 2003/0212741 A1 | 11/2003 | Giasco |
| 2004/0247198 A1 | 12/2004 | Ghosh et al. |
| 2005/0010712 A1 | 1/2005 | Kim et al. |
| 2005/0102354 A1 | 5/2005 | Hollenbeck et al. |
| 2005/0114476 A1 | 5/2005 | Chen et al. |
| 2005/0132297 A1 | 6/2005 | Milic-Frayling et al. |
| 2005/0153686 A1 | 7/2005 | Kall et al. |
| 2005/0165925 A1 | 7/2005 | Dan et al. |
| 2005/0257400 A1 | 11/2005 | Sommerer et al. |
| 2005/0266420 A1 | 12/2005 | Pusztai et al. |
| 2005/0278761 A1 | 12/2005 | Gonder et al. |
| 2006/0002383 A1 | 1/2006 | Jeong et al. |
| 2006/0074967 A1 | 4/2006 | Shaburov |
| 2006/0122927 A1 | 6/2006 | Huberman et al. |
| 2006/0126865 A1 | 6/2006 | Blarney Et Ai |
| 2006/0173628 A1 | 8/2006 | Sampas et al. |
| 2007/0026426 A1 | 2/2007 | Fuernkranz et al. |
| 2007/0076703 A1 | 4/2007 | Yoneda et al. |
| 2007/0088703 A1 | 4/2007 | Kasiolas et al. |
| 2007/0174541 A1 * | 7/2007 | Chandrasekaran ......................... G06F 12/0817 711/100 |
| 2008/0027954 A1 | 1/2008 | Gan et al. |
| 2008/0028086 A1 | 1/2008 | Chetuparambil et al. |
| 2008/0077607 A1 | 3/2008 | Gatawood et al. |
| 2008/0155100 A1 | 6/2008 | Ahmed et al. |
| 2008/0184245 A1 | 7/2008 | St-Jean |
| 2008/0260119 A1 | 10/2008 | Marathe et al. |
| 2008/0279167 A1 | 11/2008 | Cardei et al. |
| 2009/0062623 A1 | 3/2009 | Cohen et al. |
| 2009/0076851 A1 | 3/2009 | Rao |
| 2009/0150084 A1 | 6/2009 | Colwell et al. |
| 2009/0198389 A1 | 8/2009 | Kirchhof-Falter et al. |
| 2009/0310485 A1 | 12/2009 | Averi et al. |
| 2009/0319188 A1 | 12/2009 | Otto |
| 2010/0005077 A1 | 1/2010 | Krishnamurthy et al. |
| 2010/0042809 A1 | 2/2010 | Schenfeld et al. |
| 2010/0076845 A1 | 3/2010 | Ramer et al. |
| 2010/0076856 A1 | 3/2010 | Mullins |
| 2010/0122065 A1 | 5/2010 | Dean et al. |
| 2010/0131639 A1 | 5/2010 | Narayana et al. |
| 2010/0131700 A1 | 5/2010 | Castillo |
| 2010/0184093 A1 | 7/2010 | Donovan et al. |
| 2010/0229178 A1 | 9/2010 | Ito |

(56) References Cited

U.S. PATENT DOCUMENTS

| | | | |
|---|---|---|---|
| 2010/0250646 A1 | 9/2010 | Dunagan et al. | |
| 2010/0290468 A1 | 11/2010 | Lynam et al. | |
| 2010/0293334 A1 | 11/2010 | Xun et al. | |
| 2010/0299437 A1 | 11/2010 | Moore | |
| 2011/0020785 A1 | 1/2011 | Lowery, Jr. et al. | |
| 2011/0029999 A1* | 2/2011 | Foti | H04L 63/10 725/25 |
| 2011/0103364 A1 | 5/2011 | Li | |
| 2011/0144932 A1* | 6/2011 | Alles | G01D 4/002 702/61 |
| 2011/0145828 A1 | 6/2011 | Takahashi et al. | |
| 2011/0208703 A1 | 8/2011 | Fisher et al. | |
| 2011/0314002 A1 | 12/2011 | Oliver et al. | |
| 2012/0030599 A1 | 2/2012 | Butt et al. | |
| 2012/0059707 A1 | 3/2012 | Goenka et al. | |
| 2012/0071774 A1 | 3/2012 | Osorio et al. | |
| 2012/0102409 A1* | 4/2012 | Fan | G06F 3/0481 715/738 |
| 2012/0191699 A1 | 7/2012 | George et al. | |
| 2012/0209526 A1 | 8/2012 | Imhof | |
| 2013/0035956 A1 | 2/2013 | Carmeli et al. | |
| 2013/0044925 A1 | 2/2013 | Kozuka et al. | |
| 2013/0054670 A1 | 2/2013 | Keyes et al. | |
| 2013/0194928 A1 | 8/2013 | Iqbal | |
| 2013/0246460 A1 | 9/2013 | Maltbie et al. | |
| 2013/0252631 A1* | 9/2013 | Alizadeh-Shabdiz | H04W 4/025 455/456.1 |
| 2013/0282897 A1 | 10/2013 | Siegel et al. | |
| 2013/0290249 A1 | 10/2013 | Merriman et al. | |
| 2013/0291118 A1 | 10/2013 | Li et al. | |
| 2013/0318257 A1 | 11/2013 | Lee et al. | |
| 2013/0326538 A1 | 12/2013 | Gupta et al. | |
| 2013/0346229 A1 | 12/2013 | Martin et al. | |
| 2013/0346988 A1 | 12/2013 | Bruno et al. | |
| 2014/0012843 A1 | 1/2014 | Soon-Shiong | |
| 2014/0025393 A1 | 1/2014 | Wang et al. | |
| 2014/0032240 A1 | 1/2014 | Lougheeci et al. | |
| 2014/0075161 A1 | 3/2014 | Zhang et al. | |
| 2014/0081984 A1 | 3/2014 | Sitsky et al. | |
| 2014/0082178 A1 | 3/2014 | Boidyrev et al. | |
| 2014/0143251 A1 | 5/2014 | Wang et al. | |
| 2014/0173331 A1 | 6/2014 | Martin et al. | |
| 2014/0173618 A1 | 6/2014 | Neuman et al. | |
| 2014/0188596 A1 | 7/2014 | Nangle, III | |
| 2014/0214752 A1 | 7/2014 | Rash et al. | |
| 2014/0215007 A1 | 7/2014 | Rash et al. | |
| 2014/0278808 A1 | 9/2014 | Iyoob et al. | |
| 2014/0279201 A1 | 9/2014 | Iyoob et al. | |
| 2014/0280298 A1 | 9/2014 | Petride et al. | |
| 2014/0280363 A1 | 9/2014 | Heng et al. | |
| 2014/0280604 A1 | 9/2014 | Ahiska et al. | |
| 2014/0280695 A1 | 9/2014 | Sharma et al. | |
| 2014/0280880 A1 | 9/2014 | Tellis et al. | |
| 2014/0280990 A1 | 9/2014 | Dove et al. | |
| 2014/0310258 A1 | 10/2014 | Tian | |
| 2014/0310718 A1* | 10/2014 | Gerphagnon | G06F 9/5094 718/103 |
| 2014/0320497 A1 | 10/2014 | Voinovic et al. | |
| 2014/0324647 A1 | 10/2014 | Iyoob et al. | |
| 2014/0325041 A1* | 10/2014 | Xu | H04L 41/0816 709/221 |
| 2014/0333638 A1 | 11/2014 | Kaminski | |
| 2014/0358999 A1 | 12/2014 | Rabinowitz et al. | |
| 2014/0365518 A1 | 12/2014 | Calo et al. | |
| 2014/0365662 A1 | 12/2014 | Dave et al. | |
| 2014/0372611 A1 | 12/2014 | Matsuda et al. | |
| 2014/0379722 A1 | 12/2014 | Mysur et al. | |
| 2015/0006619 A1 | 1/2015 | Banadaki et al. | |
| 2015/0019710 A1 | 1/2015 | Shaashua et al. | |
| 2015/0039586 A1 | 2/2015 | Kerschbaum et al. | |
| 2015/0039667 A1 | 2/2015 | Shah et al. | |
| 2015/0058843 A1 | 2/2015 | Holler et al. | |
| 2015/0066646 A1 | 3/2015 | Sriharsha et al. | |
| 2015/0081877 A1 | 3/2015 | Sethi et al. | |
| 2015/0088786 A1 | 3/2015 | Anandhakrishnan | |
| 2015/0092561 A1 | 4/2015 | Sigoure | |
| 2015/0120791 A1 | 4/2015 | Gummaraju et al. | |
| 2015/0121371 A1 | 4/2015 | Gummaraju et al. | |
| 2015/0169683 A1 | 6/2015 | Chandramouli et al. | |
| 2015/0170616 A1 | 6/2015 | Corpet et al. | |
| 2015/0178052 A1 | 6/2015 | Gupta et al. | |
| 2015/0193583 A1 | 7/2015 | McNair et al. | |
| 2015/0201036 A1 | 7/2015 | Nishiki et al. | |
| 2015/0222723 A1 | 8/2015 | Adapalli et al. | |
| 2015/0254344 A1 | 9/2015 | Kulkarni et al. | |
| 2015/0254558 A1 | 9/2015 | Arnold et al. | |
| 2015/0262268 A1 | 9/2015 | Padmanabhan et al. | |
| 2015/0264122 A1 | 9/2015 | Shau et al. | |
| 2015/0269230 A1 | 9/2015 | Kardes et al. | |
| 2015/0277791 A1 | 10/2015 | Li et al. | |
| 2015/0278513 A1 | 10/2015 | Krasin et al. | |
| 2015/0295781 A1 | 10/2015 | Maes | |
| 2015/0302075 A1 | 10/2015 | Schechter et al. | |
| 2015/0319144 A1* | 11/2015 | Barton | G06F 9/485 713/168 |
| 2015/0326644 A1 | 11/2015 | Yahalom et al. | |
| 2015/0334548 A1* | 11/2015 | Liu | H04W 84/12 370/329 |
| 2015/0339210 A1 | 11/2015 | Kopp et al. | |
| 2015/0355946 A1 | 12/2015 | Kang | |
| 2015/0369618 A1 | 12/2015 | Barnard et al. | |
| 2016/0004827 A1 | 1/2016 | Siiva et al. | |
| 2016/0006628 A1 | 1/2016 | Herring et al. | |
| 2016/0020967 A1 | 1/2016 | Thubert et al. | |
| 2016/0063191 A1 | 3/2016 | Vesto et al. | |
| 2016/0072726 A1* | 3/2016 | Soni | H04L 41/0896 709/208 |
| 2016/0087909 A1 | 3/2016 | Chatterjee et al. | |
| 2016/0088023 A1 | 3/2016 | Handa et al. | |
| 2016/0098021 A1 | 4/2016 | Zornio et al. | |
| 2016/0098472 A1 | 4/2016 | Appleton | |
| 2016/0098662 A1 | 4/2016 | Voss et al. | |
| 2016/0112531 A1 | 4/2016 | Milton et al. | |
| 2016/0117373 A1 | 4/2016 | Gang et al. | |
| 2016/0123941 A1* | 5/2016 | Bowers | G01N 33/0009 422/98 |
| 2016/0125056 A1 | 5/2016 | Knezevic et al. | |
| 2016/0132576 A1 | 5/2016 | Qi et al. | |
| 2016/0170882 A1 | 6/2016 | Choi et al. | |
| 2016/0171072 A1 | 6/2016 | Jagtiani et al. | |
| 2016/0179642 A1 | 6/2016 | Cai | |
| 2016/0179979 A1 | 6/2016 | Aasman et al. | |
| 2016/0182305 A1 | 6/2016 | Martin et al. | |
| 2016/0182327 A1 | 6/2016 | Coleman, Jr. et al. | |
| 2016/0183313 A1* | 6/2016 | Vallabhu | H04W 76/12 370/329 |
| 2016/0188594 A1 | 6/2016 | Ranganathan | |
| 2016/0196324 A1 | 7/2016 | Haviv et al. | |
| 2016/0205106 A1 | 7/2016 | Yacoub et al. | |
| 2016/0241893 A1 | 8/2016 | Allhands et al. | |
| 2016/0246981 A1 | 8/2016 | Nakagawa et al. | |
| 2016/0260023 A1 | 9/2016 | Miserendino, Jr. et al. | |
| 2016/0261727 A1 | 9/2016 | Yang et al. | |
| 2016/0267132 A1 | 9/2016 | Castellanos et al. | |
| 2016/0269228 A1 | 9/2016 | Franke et al. | |
| 2016/0283551 A1 | 9/2016 | Fokoue-Nkoutche et al. | |
| 2016/0323377 A1 | 11/2016 | Einkauf et al. | |
| 2016/0328661 A1 | 11/2016 | Reese et al. | |
| 2016/0337473 A1 | 11/2016 | Rao | |
| 2016/0350157 A1 | 12/2016 | Necas | |
| 2017/0006135 A1 | 1/2017 | Siebel et al. | |
| 2017/0032263 A1 | 2/2017 | Yuan et al. | |
| 2017/0053008 A1 | 2/2017 | Frenkel et al. | |
| 2017/0083573 A1 | 3/2017 | Rogers et al. | |
| 2017/0109299 A1 | 4/2017 | Beiair et al. | |
| 2017/0116289 A1 | 4/2017 | Deshmukh et al. | |
| 2017/0149630 A1 | 5/2017 | Feller et al. | |
| 2017/0155707 A1 | 6/2017 | Rash et al. | |
| 2017/0187785 A1 | 6/2017 | Johnson et al. | |
| 2017/0220646 A1 | 8/2017 | Schechter et al. | |
| 2017/0272458 A1 | 9/2017 | Muddu et al. | |
| 2017/0323028 A1 | 11/2017 | Jonker et al. | |

(56) References Cited

U.S. PATENT DOCUMENTS

| | | |
|---|---|---|
| 2017/0337135 A1 | 11/2017 | Hu et al. |
| 2017/0346690 A1 | 11/2017 | Dorado et al. |
| 2018/0054355 A1 | 2/2018 | Baser et al. |
| 2018/0101583 A1 | 4/2018 | Li et al. |
| 2018/0109934 A1* | 4/2018 | Grube .............. G06Q 10/06315 |
| 2018/0181957 A1 | 6/2018 | Crabtree et al. |
| 2018/0189296 A1 | 7/2018 | Ashour et al. |
| 2018/0232262 A1 | 8/2018 | Chowdhury et al. |
| 2018/0240062 A1 | 8/2018 | Crabtree et al. |
| 2018/0308585 A1 | 10/2018 | Holmes et al. |
| 2019/0018965 A1 | 1/2019 | Hoscheit et al. |
| 2019/0026146 A1 | 1/2019 | Peffers et al. |
| 2019/0130122 A1 | 5/2019 | Barnes et al. |
| 2019/0149418 A1 | 5/2019 | Bertsche et al. |
| 2019/0149479 A1 | 5/2019 | Florissi et al. |
| 2019/0173666 A1 | 6/2019 | Ardashev et al. |
| 2019/0176335 A1 | 6/2019 | Shivararn et al. |
| 2019/0179672 A1 | 6/2019 | Christidis et al. |
| 2019/0206090 A1 | 7/2019 | Ray et al. |
| 2019/0207759 A1 | 7/2019 | Chan et al. |
| 2019/0208004 A1* | 7/2019 | Florissi .................. G16B 45/00 |
| 2019/0214848 A1 | 7/2019 | Waffner |
| 2019/0244243 A1 | 8/2019 | Goldberg et al. |
| 2019/0253134 A1 | 8/2019 | Coleman et al. |

OTHER PUBLICATIONS

J. Leskovec, "Graphs Over Time: Densification Laws, Shrinking Diameters and Possible Explanations," Proceedings of the Eleventh ACM SIGKDD International Conference on Knowledge Discovery in Data Mining, Aug. 21-24, 2005, pp. 177-187.
H. Zha et al., "Bipartite Graph Partitioning and Data Clustering," Proceedings of the Tenth International Conference on Information and Knowledge Management, Oct. 5-10, 2001, pp. 25-32.
A. Oghabian et al., "Biclustering Methods: Biological Relevance and Application in Gene Expression Analysis," PLOS ONE, Mar. 20, 2014, 10 pages, vol. 9, No. 3.
S. Ryza, "How to: Tune Your Apache Spark Jobs," https://blog.cloudera.com/blog/2015/03/how-to-tune-your-apache-spark-jobs-part-1/, Mar. 9, 2015, 23 pages.
White, "Hadoop: The Definitive Guide," O'Reilly Media, Inc., Fourth Edition, Sebastopol, CA, Apr. 2015, 756 pages.
L. Shashank, "Spark on Yarn," https://slideshare.net/datamantra/spark-on-yarn-54201193, Oct. 21, 2015, 47 pages.
D. Ucar et al., "Combinatorial Chromatin Modification Patterns in the Human Genome Revealed by Subspace Clustering," Nucleic Acids Research, May 1, 2011, pp. 4063-4075, vol. 39, No. 10.
V.K. Vavilapalli et al., "Apache Hadoop YARN: Yet Another Resource Negotiator," Proceedings of the 4th Annual Symposium on Cloud Computing (SOCC), Article No. 5, Oct. 2013, 16 pages.
A.C. Murthy et al., "Apache Hadoop YARN: Moving beyond MapReduce arid Batch Processing with Apache Hadoop 2," Addison-Wesley Professional, Mar. 29, 2014, 78 pages.
Global Alliance for Genomics and Health, "Beacons," https://genomicsandhealth.org/work-products-demonstration-projects/beacons, Jun. 27, 2014, 2 pages.
Data Working Group, "Global Alliance Genomics API," http://ga4gh.org/#documentation, Dec. 28, 2015, 2 pages.
Aaron Krol, "Beacon Project Cracks the Door for Genomic Data Sharing," http://www.bio-itworld.com/2015/8/14/beacon-project-cracks-door-genomic-data-sharing.html, Aug. 14, 2015, 3 pages.
Wikipedia, "Apache Spark," https://en.wikipedia.org/wiki/Apache_Spark, Apr. 10, 2017, 6 pages.
M.K. Gardner et al., "Parallel Genomic Sequence-Searching on an Ad-Hoc Grid: Experiences, Lessons Learned, and Implications," Proceedings of the 2006 ACM/IEEE SC/06 Conference, IEEE Computer Society, 2006, 14 pages.
A.G. Craig et al., "Ordering of Cosmid Clones Covering the Herpes Simplex Virus Type I (HSV-I) Genome: A Test Case for Fingerprinting by Hybridisation," Nucleic Acids Research, vol. 18, 1990, pp. 2653-2660.
T.R. Golub et al., "Molecular classification of Cancer: Class Discovery and Class Prediction by Gene Expression Monitoring," Science, vol. 286, Oct. 15, 1999, pp. 531-537.
D. Singh et al., "Gene Expression Correlates of Clinical Prostate Cancer Behavior," Cancer Cell, vol. 1, Mar. 2002, pp. 203-209.
P.P. Jayaraman et al., "Analytics-as-a-Service in a Multi-Cloud Environment Through Semantically-Enabled Hierarchical Data Processing," Software: Practice and Experience, Aug. 2017, pp. 1139-1156, vol. 47, No. 8.
J.Y.L. Lee et al., "Sufficiency Revisited: Rethinking Statistical Algorithms in the Big Data Era," The American Statistician, Dec. 15, 2016, 22 pages.
S. Wang et al., "Genome Privacy: Challenges, Technical Approaches to Mitigate Risk, and Ethical Considerations in the United States," Annals of the New York Academy of Sciences, Jan. 2017, pp. 73-83, vol. 1387, No. 1.
K. Xu et al., "Privacy-Preserving Machine Learning Algorithms for Big Data Systems," IEEE 35th International Conference on Distributed Computing Systems (ICDCS), Jun. 29-Jul. 2, 2015, pp. 318-327.
Dell, "Dell Boomi Platform: Connect Every Part of Your Business to Transform How You do Business," https://marketing.boorni.com/rs/777-AVU-348/images/Boomi-Integration-Cloud.pdf, 2017, 4 pages.
X. Wu et al., "Privacy Preserving Data Mining Research: Current Status and Key Issues," Proceedings of the 7th International Conference on Computational Science, Part III: ICCS 2007, May 2007, pp. 762-772.
A.P. Kulkarni et al., "Survey on Hadoop and Introduction to YARN," International Journal of Emerging Technology and Advanced Engineering, May 2014, pp. 82-87, vol. 4, No. 5.
R.R. Miller et al., "Metagenomics for Pathogen Detection in Public Health," Genome Medicine, Sep. 20, 2013, 14 pages, vol. 5, No. 81.
T. Thomas et al., "Metagenomics—A Guide from Sampling to Data Analysis," Microbial Informatics and Experimentation, Oct. 13, 2011, 12 pages, vol. 2, No. 3.
U.S. Appl. No. 14/982,351 filed in the name of Patricia Comes Soares Florissi et al., filed Dec. 29, 2015 and entitled "Distributed Catalog Service for Multi-Cluster Data Processing Platform."
U.S. Appl. No. 15/395,340 filed in the name of Bryan Duerk et al., filed Dec. 30, 2016 and entitled "Data-Driven Automation Mechanism for Analytics Workload Distribution."
U.S. Appl. No. 15/485,843 filed in the name of Patricia Gomes Soares Florissi et al., filed Apr. 12, 2017 and entitled "Scalable Distributed in-Memory Computation.".
U.S. Appl. No. 15/582,743 filed in the name of Patricia Gomes Soares Florissi et al., filed Apr. 30, 2017 and entitled "Scalable Distributed in-Memory Computation Utilizing Batch Mode Extensions."
U.S. Appl. No. 15/281,248 filed in the name of Patricia Gomes Soares Florissi et al., filed Sep. 30, 2016 and entitled "Methods and Apparatus Implementing Data Model for Disease Monitoring, Characterization and Investigation".
U.S. Appl. No. 15/827,663 filed in the name of Patricia Gomes Soares Florissi et al, filed Nov. 30, 2017 and entitled "Global Benchmarking and Statistical Analysis at Scale."

* cited by examiner

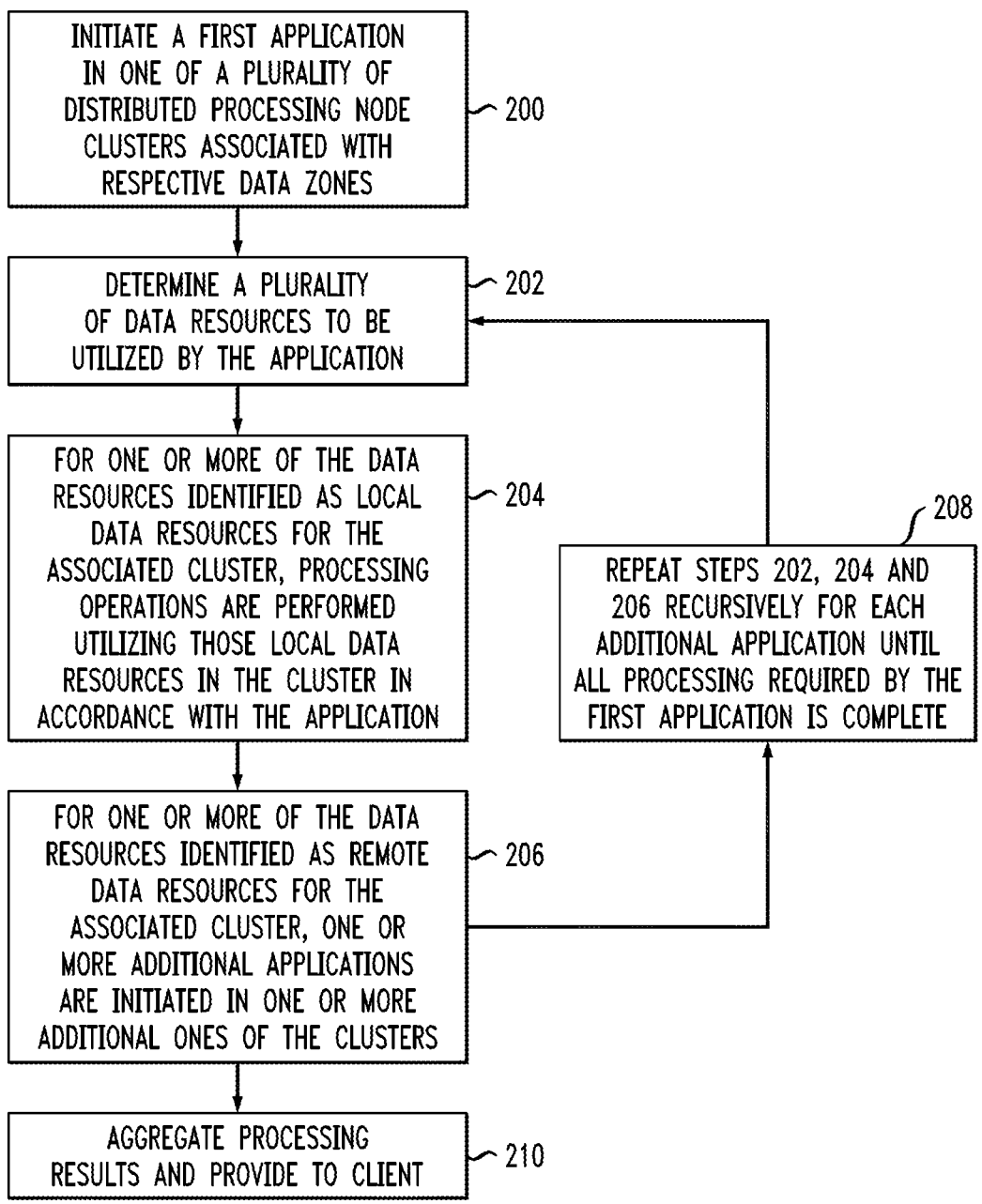

BEACON-BASED DISTRIBUTED DATA PROCESSING PLATFORM

PRIORITY CLAIM

The present application is a continuation of U.S. patent application Ser. No. 14/982,355, filed Dec. 29, 2015, which claims priority to U.S. Provisional Patent Application Ser. No. 62/143,404, entitled "World Wide Hadoop Platform," and U.S. Provisional Patent Application Ser. No. 62/143,685, entitled "Bioinformatics," both filed Apr. 6, 2015, and incorporated by reference herein in their entirety.

RELATED APPLICATIONS

The present application is related to U.S. patent application Ser. No. 14/982,341, entitled "Multi-Cluster Distributed Data Processing Platform," and U.S. patent application Ser. No. 14/982,351, entitled "Distributed Catalog Service for Multi-Cluster Data Processing Platform," each of which is incorporated by reference herein in its entirety.

FIELD

The field relates generally to information processing systems, and more particularly to information processing systems that implement distributed processing across a plurality of processing nodes.

BACKGROUND

The need to extract knowledge from data collected on a global scale continues to grow. In many cases the data may be dispersed across multiple geographic locations, owned by different entities, and in different formats. Although numerous distributed data processing frameworks exist today, these frameworks have significant drawbacks. For example, data-intensive computing tasks often use data processing frameworks such as MapReduce or Spark. However, these frameworks typically require deployment of a distributed file system shared by all of the processing nodes, and are therefore limited to data that is accessible via the shared distributed file system. Such a shared distributed file system can be difficult to configure and maintain over multiple local sites that are geographically dispersed and possibly also subject to the above-noted differences in ownership and data format. In the absence of a shared distributed file system, conventional arrangements may require that data collected from sources in different geographic locations be copied from their respective local sites to a single centralized site configured to perform data analytics. Such an arrangement is not only slow and inefficient, but it can also raise serious privacy concerns regarding the copied data.

SUMMARY

Illustrative embodiments of the present invention provide information processing systems that are configured to execute distributed applications over multiple distributed data processing node clusters associated with respective distinct data zones. Each data zone in a given embodiment illustratively comprises a Hadoop YARN cluster configured to support multiple distributed data processing frameworks, such as MapReduce and Spark. These and other similar arrangements disclosed herein can be advantageously configured to provide analytics functionality in a decentralized and privacy-preserving manner, so as to overcome the above-noted drawbacks of conventional systems. This is achieved in some embodiments by orchestrating execution of distributed applications across the multiple YARN clusters. Computations associated with data available locally within a given YARN cluster are performed within that cluster. Accordingly, instead of moving data from local sites to a centralized site, computations are performed within the local sites where the needed data is available. This provides significant advantages in terms of both performance and privacy. Additional advantages are provided in terms of security, governance, risk and compliance.

In one embodiment, a method comprises initiating a first application in a first one of a plurality of distributed processing nodes, and responsive to initiation of the first application, identifying a plurality of beacon entities to be contacted in conjunction with execution of at least a portion of the first application. The method also comprises, for each of at least a subset of the identified beacon entities, initiating an additional application in an additional one of the plurality of distributed processing nodes. The method further comprises aggregating processing results from the first and one or more additional processing nodes, and providing the aggregated processing results to a client.

The plurality of distributed processing nodes may comprise a plurality of YARN clusters associated with respective data zones, with each of the clusters being configured to perform processing operations utilizing local data resources locally accessible within its corresponding data zone. The data zones in some embodiments are associated with respective ones of the beacon entities.

These and other illustrative embodiments include, without limitation, methods, apparatus, systems, and processor-readable storage media.

BRIEF DESCRIPTION OF THE DRAWINGS

FIG. 2 is a flow diagram of an exemplary process implemented in the multi-cluster distributed data processing platform of FIG. 1.

DETAILED DESCRIPTION

Illustrative embodiments of the present invention will be described herein with reference to exemplary information processing systems and associated computers, servers, storage devices and other processing devices. It is to be appreciated, however, that embodiments of the invention are not restricted to use with the particular illustrative system and device configurations shown. Accordingly, the term "information processing system" as used herein is intended to be broadly construed, so as to encompass, for example, processing systems comprising cloud computing and storage systems, as well as other types of processing systems comprising various combinations of physical and virtual processing resources. An information processing system may therefore comprise, for example, a plurality of data centers each comprising one or more clouds hosting multiple tenants that share cloud resources.

Figure 1:
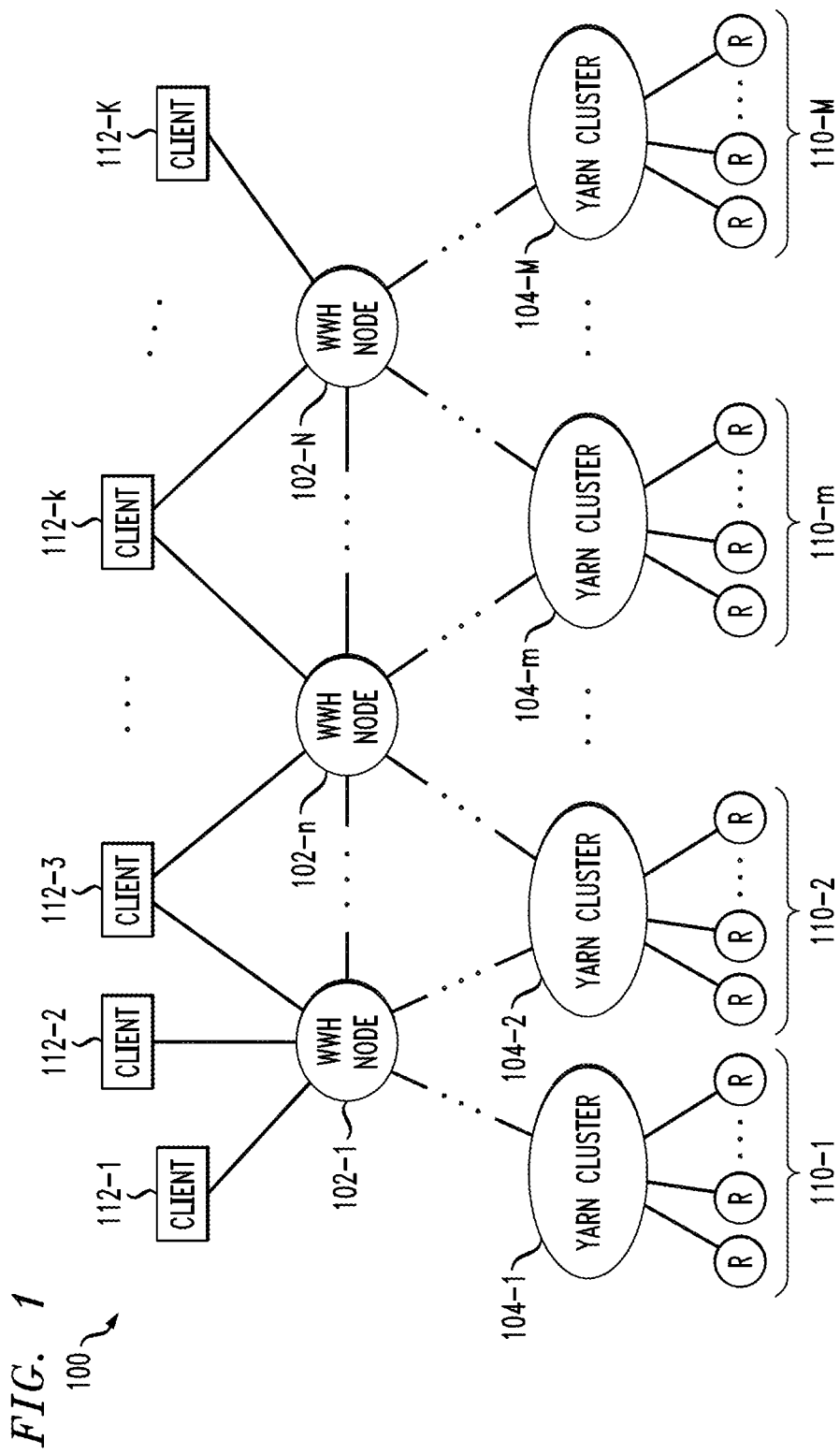
FIG. 1 is a block diagram of an information processing system comprising a multi-cluster distributed data processing platform in an illustrative embodiment of the invention.

FIG. 1 shows an information processing system 100 comprising a multi-cluster distributed data processing platform in an illustrative embodiment. The system 100 comprises a plurality of processing nodes 102, individually denoted as 102-1, . . . 102-n, . . . 102-N, each of which communicates with one or more Apache Hadoop YARN ("Yet Another Resource Negotiator") clusters, individually denoted as 104-1, 104-2, . . . 104-m, . . . 104-M. The processing nodes 102 are configured to communicate with one another and with their associated YARN clusters 104 over one or more networks that are not explicitly shown in the figure. Apache Hadoop YARN is also referred to as Hadoop 2.0, and is described in, for example, V. K. Vavilapalli et al., "Apache Hadoop YARN: Yet Another Resource Negotiator," Proceedings of the 4th Annual Symposium on Cloud Computing, SOCC '13, pp. 5:1-5:16, ACM, New York, N.Y., USA, 2013, which is incorporated by reference herein.

The processing nodes 102 are illustratively implemented as respective worldwide data nodes, and more particularly as respective worldwide Hadoop (WWH) nodes, although numerous alternative processing node types can be used in other embodiments. The WWH nodes are assumed to be configured to perform operations in accordance with any framework supported by Hadoop YARN clusters comprising respective ones of the YARN clusters 104. Examples of frameworks supported by each of the Hadoop YARN clusters include MapReduce, Spark, Hive, MPI and numerous others. The acronym WWH as used herein is additionally or alternatively intended to refer to a "worldwide herd" arrangement where the term "herd" in this context illustratively connotes multiple geographically-distributed Hadoop platforms. More generally, WWH is used to denote a worldwide data processing platform potentially comprising multiple clusters.

In the FIG. 1 embodiment, the multi-cluster distributed data processing platform more particularly comprises a WWH platform having one or more layers of WWH nodes 102 and a plurality of potentially geographically-distributed YARN clusters 104. Each of the YARN clusters 104 comprises a corresponding cluster of distributed data processing nodes. The WWH platform is illustratively configured for worldwide scale, geographically-dispersed computations and other types of cluster-based processing based on locally-accessible data resources, as will be described in more detail elsewhere herein.

It is to be appreciated that a wide variety of other types of processing nodes 102 can be used in other embodiments. Accordingly, the use of WWH nodes in the FIG. 1 embodiment and other embodiments disclosed herein is by way of illustrative example only, and should not be construed as limiting in any way.

It should also be noted that one or more of the WWH nodes 102 in some embodiments can be part of a corresponding one of the YARN clusters 104. For example, in some embodiments of a WWH platform as disclosed herein, the YARN clusters 104 themselves each comprise one or more layers of WWH nodes. Accordingly, these and other embodiments need not include a separate layer of WWH nodes 102 above the YARN clusters 104. The WWH nodes 102 may be viewed as examples of what are more generally referred to herein as distributed data processing nodes. The YARN clusters 104 are each also assumed to comprise a plurality of additional or alternative distributed data processing nodes.

Each YARN cluster 104 includes a resource manager for that cluster, and from a larger perspective YARN can be viewed as a cluster-wide operating system that allows applications to utilize the dynamic and parallel resource infrastructure a computer cluster offers. However, conventional YARN implementations are generally configured to operate in single-cluster environments, and do not provide any support for managing distributed applications which span across more than one cluster.

The WWH platform in the FIG. 1 embodiment is an example of what is more generally referred to herein as a "multi-cluster distributed data processing platform." This WWH platform and other WWH platforms disclosed herein advantageously extends YARN to multi-cluster environments. For example, the WWH platform in some embodiments is configured to orchestrate the execution of distributed WWH applications on a worldwide scale, across multiple, potentially geographically-distributed YARN clusters. The WWH platform therefore provides a platform for running distributed applications across multiple data zones each having a corresponding YARN cluster.

Other types of multi-cluster distributed data processing platforms may be implemented in other embodiments. Accordingly, references herein to a WWH platform, YARN clusters and associated features are intended as illustrative examples only, and should not be construed as limiting in any way. For example, other embodiments can be implemented without using WWH nodes or YARN clusters. Accordingly, it should be understood that the distributed data processing techniques disclosed herein are more generally applicable to a wide variety of other types of multi-cluster platforms.

Each of the YARN clusters 104 in the system 100 is associated with a corresponding set of local data resources 110, individually denoted as local data resources sets 110-1, 110-2, . . . 110-m, . . . 110-M. The local data resource sets each provide one or more local data resources to the corresponding YARN cluster for analytics processing. Results of the processing performed within a given YARN cluster utilizing one or more locally available data resources accessible to that YARN cluster are illustratively provided to one or more other ones of the YARN clusters or to an associated one of the WWH nodes 102 for additional processing associated with provision of analytics functionality within the system 100.

The data resources of each of the sets 110 of data resources are individually identified using the letter R in FIG. 1. Although these data resources are illustratively shown as being external to the YARN clusters 104, this is by way of example only and it is assumed in some embodiments that at least a subset of the data resources of a given set 110 are within the corresponding YARN cluster 104. Accordingly, a given YARN cluster can perform processing operations using a combination of internal and external local data resources.

The results of the analytics processing performed by a given one of the YARN clusters 104 illustratively comprise results of local analytics processing using YARN frameworks such as MapReduce, Spark and numerous others.

It should be understood that the above-noted analytics results are merely examples of what are more generally referred to herein as "processing results" of a given cluster. Such results can take different forms in different embodiments, as will be readily appreciated by those skilled in the art. For example, such processing results can comprise local analytics results that have been processed in a variety of different ways within a YARN cluster before being provided to one of more of the WWH nodes 102 for additional processing. Numerous other types of processing results can be used in other embodiments.

The WWH nodes 102 are each coupled to one or more clients 112. By way of example, the set of clients 112 may include one or more desktop computers, laptop computers, tablet computers, mobile telephones or other types of communication devices or other processing devices in any combination. The clients are individually denoted in the figure as clients 112-1, 112-2, . . . 112-$k$, . . . 112-K. The clients 112 may comprise, for example, respective end users or associated hardware entities, software entities or other equipment entities. For example, a "client" as the term is broadly used herein can comprise a software-implemented entity running on a user device or other processing device within the system 100.

The variables N, M and K denote arbitrary values, as embodiments of the invention can be configured using any desired number of WWH nodes 102, YARN clusters 104 and clients 112. For example, some embodiments may include multiple YARN clusters 104 and multiple clients 112 but only a single WWH node 102, or multiple WWH nodes 102 corresponding to respective ones of the YARN clusters 104. Numerous alternative arrangements are possible, including embodiments in which a single system element combines functionality of at least a portion of a WWH node and functionality of at least a portion of a YARN cluster. Thus, alternative embodiments in which the functions of a WWH node and a YARN cluster are at least partially combined into a common processing entity are possible.

The WWH nodes 102 in some embodiments are implemented at least in part as respective analysis nodes. The analysis nodes may comprise respective computers in a cluster of computers associated with a supercomputer or other high performance computing (HPC) system. The term "processing node" as used herein is intended to be broadly construed, and such nodes in some embodiments may comprise respective compute nodes in addition to or in place of providing analysis node functionality.

The system 100 may include additional nodes that are not explicitly shown in the figure. For example, the system 100 may comprise one or more name nodes. Such name nodes may comprise respective name nodes of a Hadoop Distributed File System (HDFS), although other types of name nodes can be used in other embodiments. Particular objects or other stored data of a storage platform can be made accessible to one or more of the WWH nodes 102 via a corresponding name node. For example, such name nodes can be utilized to allow the WWH nodes 102 to address multiple HDFS namespaces within the system 100.

Each of the WWH nodes 102 and YARN clusters 104 is assumed to comprise one or more databases for storing analytics processing results and possibly additional or alternative types of data.

Databases associated with the WWH nodes 102 or the YARN clusters 104 and possibly other elements of the system 100 can be implemented using one or more storage platforms. For example, a given storage platform can comprise any of a variety of different types of storage including network-attached storage (NAS), storage area networks (SANs), direct-attached storage (DAS), distributed DAS and software-defined storage (SDS), as well as combinations of these and other storage types.

A given storage platform may comprise storage arrays such as VNXx and Symmetrix VIVIAX® storage arrays, both commercially available from EMC Corporation. Other types of storage products that can be used in implementing a given storage platform in an illustrative embodiment include software-defined storage products such as ScaleIO™ and ViPR®, server-based flash storage devices such as DSSD™, cloud storage products such as Elastic Cloud Storage (ECS), object-based storage products such as Atmos, scale-out all-flash storage arrays such as XtremIO™, and scale-out NAS clusters comprising Isilon® platform nodes and associated accelerators in the S-Series, X-Series and NL-Series product lines, all from EMC Corporation. Combinations of multiple ones of these and other storage products can also be used in implementing a given storage platform in an illustrative embodiment.

Additionally or alternatively, a given storage platform can implement multiple storage tiers. For example, a storage platform can comprise a 2 TIERS™ storage system from EMC Corporation.

These and other storage platforms can be part of what is more generally referred to herein as a processing platform comprising one or more processing devices each comprising a processor coupled to a memory.

A given processing device may be implemented at least in part utilizing one or more virtual machines or other types of virtualization infrastructure such as Docker containers or other types of Linux containers (LXCs). The WWH nodes 102 and YARN clusters 104, as well as other system components, may be implemented at least in part using processing devices of such processing platforms.

Communications between the various elements of system 100 may take place over one or more networks. These networks can illustratively include, for example, a global computer network such as the Internet, a wide area network (WAN), a local area network (LAN), a satellite network, a telephone or cable network, a cellular network, a wireless network implemented using a wireless protocol such as WiFi or WiMAX, or various portions or combinations of these and other types of communication networks.

As a more particular example, some embodiments may utilize one or more high-speed local networks in which associated processing devices communicate with one another utilizing Peripheral Component Interconnect express (PCIe) cards of those devices, and networking protocols such as InfiniBand, Gigabit Ethernet or Fibre Channel. Numerous alternative networking arrangements are possible in a given embodiment, as will be appreciated by those skilled in the art.

It is to be appreciated that the particular arrangement of system elements shown in FIG. 1 is for purposes of illustration only, and that other arrangements of additional or alternative elements can be used in other embodiments. For example, numerous alternative system configurations can be used to implement multi-cluster distributed data processing functionality as disclosed herein.

Additional details regarding example processing functionality that may be incorporated in at least a subset of the WWH nodes in illustrative embodiments are described in U.S. Pat. No. 9,020,802, entitled "Worldwide Distributed Architecture Model and Management," and U.S. Pat. No. 9,158,843, entitled "Addressing Mechanism for Data at World Wide Scale," which are commonly assigned herewith and incorporated by reference herein.

The operation of the system 100 will now be described in further detail with reference to the flow diagram of FIG. 2. The process as shown includes steps 200 through 204, and is suitable for use in the system 100 but is more generally applicable to other types of multi-cluster distributed data processing platforms.

In step 200, a first application is initiated in one of a plurality of distributed processing node clusters associated with respective data zones, with each of the clusters being configured to perform processing operations utilizing local data resources locally accessible within its corresponding data zone. With reference to the FIG. 1 embodiment, a first application is initiated in one of the YARN clusters 104, possibly via one of the WWH nodes 102, by a given one of the clients 112. The first application is illustratively what is referred to herein as a WWH application, which is a distributed application for which processing is orchestrated over multiple ones of the YARN clusters 104.

In step 202, a plurality of data resources to be utilized by the application are determined. These data resources in the context of the FIG. 1 embodiment illustratively comprise data resources from multiple ones of the data resource sets 110.

In step 204, for one or more of the plurality of data resources that are identified as local data resources, processing operations are performed utilizing the local data resources in the associated cluster in accordance with the first application. Assuming by way of example that the first application in the FIG. 1 embodiment is initiated in the first YARN cluster 104-1, the data resources identified as local data resources would include one or more of the data resources from the set 110-1.

In step 206, for one or more of the plurality of data resources that are identified as remote data resources, respective additional applications are initiated in one or more additional ones of the plurality of distributed processing node clusters. By way of example, if the first application initiated in cluster 104-1 requires processing operations utilizing remote data resources, such as local data resources of another cluster 104-2, an additional application is initiated in cluster 104-2 so that the processing operations can be performed utilizing the local data resources available to cluster 104-2.

The identification of the local or remote status of particular data resources in steps 204 and 206 illustratively involves accessing a distributed catalog service to identify for each of the plurality of data resources to be utilized by the application whether the data resource is a local data resource or a remote data resource. The distributed catalog service is illustratively distributed over the clusters with each of the clusters having visibility of a corresponding distinct portion of the distributed catalog based on its locally accessible data resources. In some embodiments, the distributed catalog service comprises a distributed WWH catalog having a corresponding instance implemented within each of the clusters. Additional details regarding such a WWH catalog and other types of distributed catalog services that may be used in illustrative embodiments will be provided elsewhere herein.

In step 208, steps 202, 204 and 206 are repeated recursively for each additional application that is initiated from the first application until all processing required by the first application is complete.

For example, assume again with reference to the FIG. 1 embodiment that one of the clients 112 initiates the first application as a first YARN application in the first YARN cluster 104-1. The first cluster 104-1 can then initiate the one or more additional applications in the one or more additional clusters 104-2 through 104-M as respective YARN applications for which the first cluster 104-1 serves as a client such that the one or more additional clusters are unaware that the one or more additional applications are part of a multi-cluster distributed application.

Moreover, at least one of the additional clusters may then determine an additional plurality of data resources to be utilized by the corresponding additional application and identify for each of the plurality of additional data resources to be utilized by the additional application whether the data resource is a local data resource that is locally accessible within the data zone of the additional cluster or a remote data resource that is not locally accessible within the data zone of the additional cluster.

If the additional plurality of data resources includes one or more remote data resources not locally accessible to the additional cluster, the additional cluster initiates one or more other applications in one or more other ones of the clusters that have local access to the one or more remote data resources.

Accordingly, processing operations are performed utilizing the data resources in the corresponding one or more additional clusters in accordance with the one or more additional applications. Each remote data resource identified in a given iteration of step 206 is actually a local data resource in the particular cluster in which the corresponding processing operations are eventually performed. In this embodiment, "all processing" is intended to be broadly construed so as to encompass all cluster-based computations to be performed within the clusters utilizing their respective sets of local data resources.

In step 210, processing results from the first and one or more additional clusters are aggregated and the aggregated processing results are provided to the client that submitted the first application.

The aggregation may be performed in some embodiments by the cluster on which the first application was initiated, which is illustratively YARN cluster 104-1 in the particular example described above. Alternatively, in other embodiments, aggregation can occur incrementally on multiple ones of the clusters.

The processing results from the first and one or more additional clusters advantageously preserve privacy of those clusters in their respective local data resources. For example, the processing results from a given one of the clusters may be permitted to be transmitted to another one of the clusters but the corresponding local data resources of the given cluster that are utilized to obtain the transmitted processing results are not permitted to be transmitted to another one of the clusters.

Similar advantages are provided with regard to other aspects of data protection, including data security.

The particular processing operations and other system functionality described in conjunction with the flow diagram of FIG. 2 are presented by way of illustrative example only, and should not be construed as limiting the scope of the invention in any way. Alternative embodiments can use other types of processing operations for implementing multi-cluster distributed data processing functionality. For example, the ordering of the process steps may be varied in other embodiments, or certain steps may be performed concurrently with one another rather than serially. Also, one or more of the process steps may be repeated periodically for different types of analytics functionality, or multiple instances of the process can be performed in parallel with one another on different WWH platforms or other types of platforms implemented within a given information processing system.

It is to be appreciated that functionality such as that described in conjunction with the flow diagram of FIG. 2 can be implemented at least in part in the form of one or more software programs stored in memory and executed by a processor of a processing device such as a computer or server. As will be described below, a memory or other storage device having executable program code of one or more software programs embodied therein is an example of what is more generally referred to herein as a "processor-readable storage medium."

Illustrative embodiments can provide a number of significant advantages relative to conventional arrangements.

For example, some embodiments provide WWH platforms that are faster and more efficient than conventional analytics systems. Moreover, multi-cluster distributed data processing platforms in some embodiments are implemented in a decentralized and privacy-preserving manner. These and other multi-cluster distributed data processing platforms advantageously overcome disadvantages of conventional practice, which as indicated previously often rely on copying of local data to a centralized site for analysis, leading to privacy and performance concerns.

In some embodiments, a multi-cluster distributed data processing platform is configured to leverage Big Data profiles and associated Big Data analytics in processing local and remote data resources across multiple geographic regions or other types of data zones.

Additional details regarding Big Data profiles and associated Big Data analytics that can be implemented in illustrative embodiments of the present invention are described in U.S. Pat. No. 9,031,992, entitled "Analyzing Big Data," which is commonly assigned herewith and incorporated by reference herein.

A multi-cluster distributed data processing platform in an illustrative embodiment can utilize the data scattered across multiple regional data centers located worldwide, while preserving data privacy and adjusting for differences in data formats and other factors between the various data centers.

A WWH platform in some embodiments leverages one or more frameworks supported by Hadoop YARN, such as MapReduce, Spark, Hive, MPI and numerous others, to support distributed computations while also minimizing data movement, adhering to bandwidth constraints in terms of speed, capacity and cost, and satisfying security policies as well as policies relating to governance, risk management and compliance.

Figure 3A:
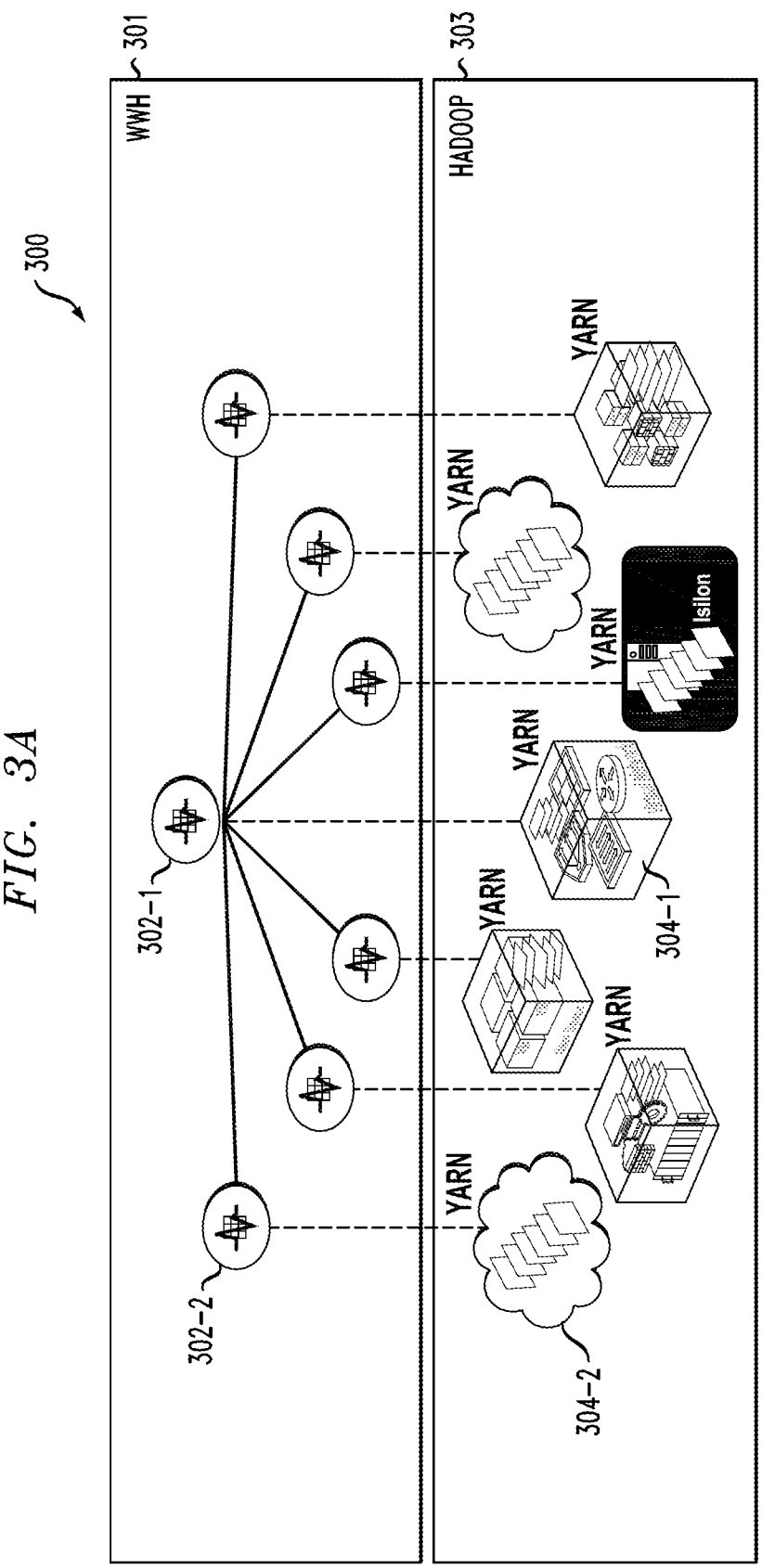
FIGS. 3A and 3B show relationships between WWH nodes and associated Hadoop YARN clusters in another illustrative embodiment. These two figures are collectively referred to herein as FIG. 3.
Figure 3B:
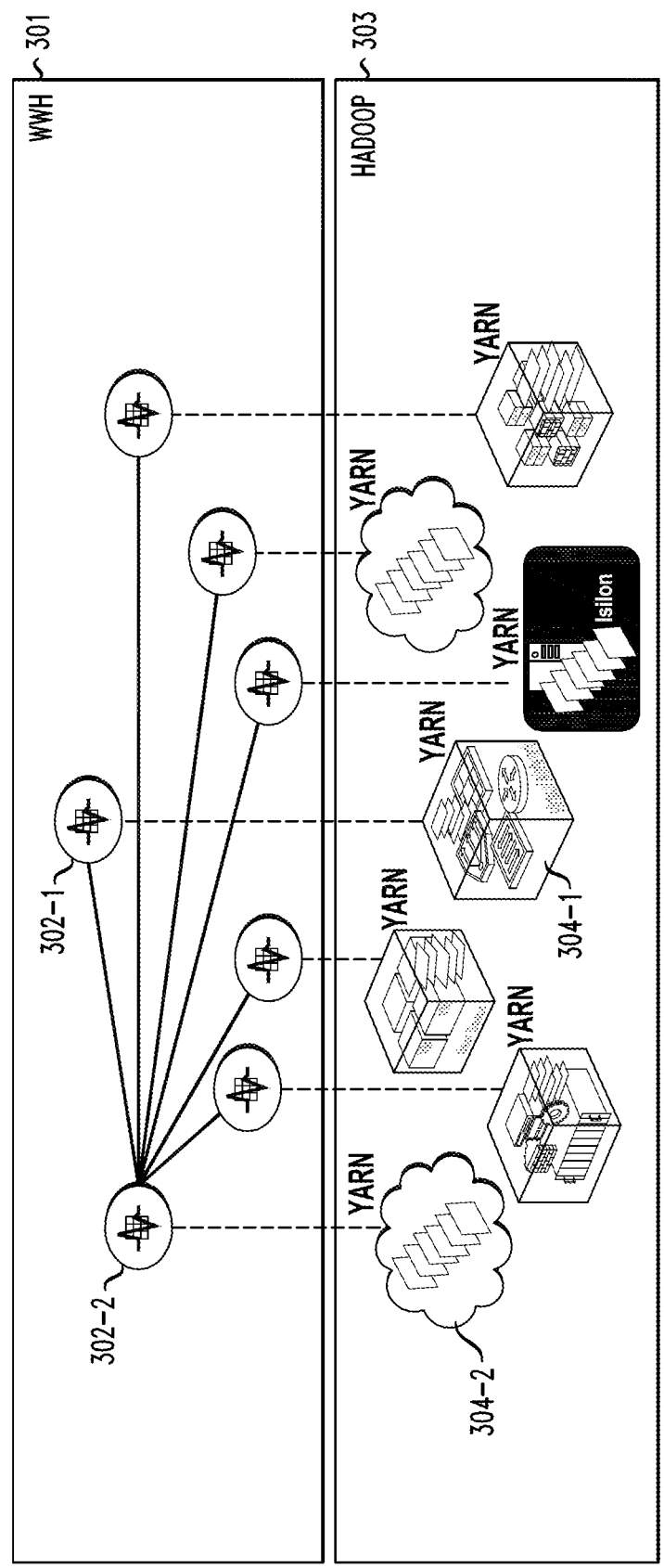

FIGS. 3A and 3B illustrate another information processing system 300 comprising a WWH platform. The WWH platform in this embodiment comprises a WWH node layer 301 that includes multiple WWH nodes 302 such as WWH nodes 302-1 and 302-2. The WWH platform further comprises a YARN cluster layer 303 that includes multiple YARN clusters 304 such as YARN cluster 304-1 and YARN cluster 304-2. The WWH nodes 302 are associated with respective ones of the YARN clusters 304.

The YARN clusters 304 are examples of what are more generally referred to herein as "distributed processing node clusters." Thus, like the YARN clusters 104 of the FIG. 1 embodiment, each of the YARN clusters 304 is assumed to include a cluster of multiple computers or other processing devices. Other types of distributed processing node clusters can be used in other embodiments. The use of Hadoop YARN in the FIG. 3 embodiment is by way of example only, and other embodiments need not utilize Hadoop YARN.

Also, although single layers 301 and 303 of respective sets of WWH nodes 302 and YARN clusters 304 are shown in this figure, other embodiments can include multiple layers of WWH nodes, multiple layers of YARN clusters, or both multiple layers of WWH nodes and multiple layers of YARN clusters.

In the information processing system 300, there is a one-to-one correspondence between the WWH nodes 302 and the respective YARN clusters 304, although this is also by way of illustrative example only. In other embodiments, a given WWH node may be associated with multiple YARN clusters. Additionally or alternatively, a given YARN cluster can be associated with multiple WWH nodes.

It is also possible that one or more of the WWH nodes 302 may each comprise a data processing node of the corresponding YARN cluster 304. Thus, in some embodiments, the separate layers 301 and 303 of the FIG. 3 embodiment are merged into a single layer of YARN clusters one or more of which each include one or more WWH nodes. Such an arrangement is considered yet another illustrative example of a WWH platform, or more generally a multi-cluster distributed data processing platform, as those terms are broadly utilized herein.

The YARN clusters 304 in the FIG. 3 embodiment are assumed to be associated with respective distinct data zones. Each of the YARN clusters 304 is configured to perform processing operations utilizing local data resources locally accessible within its corresponding data zone. The YARN clusters as illustrated in the figure illustratively comprise respective processing platforms including various arrangements of multi-node clouds, virtual infrastructure components such as virtual machines (VMs) and virtual networks, Isilon® platform nodes, and other example arrangements of distributed processing nodes.

By way of example, at least a subset of the YARN clusters 304 may comprise respective geographically-distributed regional data centers each configured to perform analytics processing utilizing the locally accessible data resources of its corresponding data zone. Additional or alternative types of boundaries may be used to separate the system 300 into multiple data zones. Accordingly, geographical distribution of the data zones and their respective clusters is not required.

The WWH nodes 302 illustratively utilize processing results from one or more of the YARN clusters 304 in orchestrating distributed applications over multiple YARN clusters in the system 300. This is achieved in a manner that preserves the privacy of those clusters in their respective local data resources. For example, processing results from a given one of the clusters may be permitted to be transmitted to another one of the clusters while the local data resources of the given cluster that are utilized to obtain the processing results are not permitted to be transmitted to another one of the clusters.

As illustrated in FIG. 3A, the WWH layer 301 may be viewed as comprising an "analytics layer" of the system. The YARN clusters 304 can be interconnected in different ways at that layer through use of different connections between the WWH nodes 302. In this particular figure, a first WWH node 302-1 is shown as being interconnected with each of the other WWH nodes 302 of the WWH layer 301.

FIG. 3B illustrates that alternative interconnections of the WWH nodes 302 are possible, including the arrangement shown in which another WWH node 302-2 initiates connections with each of the other WWH nodes 302 in orchestrating a given distributed application over multiple ones of the YARN clusters 304. It is to be appreciated that, in the FIG. 3 embodiment, any of the WWH nodes 302 can initiate a distributed application on its corresponding one of the YARN clusters 304 and that distributed application can subsequently initiate multiple additional applications involving respective additional ones of the clusters.

Again, the particular arrangements of layers, nodes and clusters shown in FIG. 3 are presented by way of example only, and should not be construed as limiting in any way.

The WWH platform in the FIG. 3 embodiment and one or more other embodiments disclosed herein illustratively adheres to local processing within each cluster using data locally accessible to that cluster. This is achieved without the need for implementing a distributed file system over the multiple clusters. Also, movement of data resources between clusters is avoided. Instead, data resources are processed locally within their respective YARN clusters.

This orchestration of distributed applications over multiple YARN clusters is facilitated in illustrative embodiments through the use of what is referred to herein as a WWH catalog. The WWH catalog is a catalog of data resources, and is an example of what is more generally referred to herein as a "distributed catalog service."

In some embodiments, each cluster that is part of the WWH platform has access to or otherwise comprises an instance of the WWH catalog implemented for that cluster. The WWH catalog instance implemented for a given cluster illustratively contains detailed information regarding local data resources of that cluster, such as, for example, file names and metadata about the files and their content, and references to one or more other clusters in the case of a non-local resource. This creates a hierarchical structure to execution of a WWH application within the WWH platform.

It should be noted that each YARN cluster need not include its own instance of the WWH catalog. For example, in some embodiments, only a subset of the YARN clusters of a multi-cluster distributed data processing platform implement respective instances of a distributed WWH catalog. In such an arrangement, YARN clusters that do not include respective WWH catalog instances can nonetheless participate in performance of computations associated with a distributed WWH application.

A WWH application identifies data files and other input data items from among the various data resources characterized by the WWH catalog. A given such input data item can more particularly comprise, for example, a text file, an XML file, a result relation of a database query or a result of an API query.

Data resources characterized by the WWH catalog can be considered global in the sense that clients are oblivious to the particular location of the resource. For example, a given resource can be comprised of several other resources, each residing in a different data zone. A meta-resource is a piece of data that describes a corresponding data resource. It generally includes the location of the resource and information about how to access the resource.

The WWH catalog is distributed over the clusters of the WWH platform with each of the clusters having visibility of only its corresponding instance of the WWH catalog. In some embodiments, the distributed instances of the WWH catalog are implemented as respective YARN applications running on respective ones of the YARN clusters of the WWH platform.

A given instance of the WWH catalog on a corresponding one of the YARN clusters typically comprises a plurality of entries with each such entry comprising a meta-resource including information characterizing location and accessibility of a corresponding one of the data resources. By way of example, the meta-resource for a given local data resource may comprise a file path to a storage location of that local data resource in the corresponding YARN cluster. Also by way of example, the meta-resource for a given remote data resource may comprise information identifying another cluster for which that data resource is a local data resource.

A given meta-resource of the WWH catalog may additionally or alternatively comprise one or more other types of information, such as, for example, information regarding transformation of the data resource into one or more designated formats, access control information, policy rules, etc.

The WWH catalog therefore illustratively provides a catalog of entries, each comprising a meta-resource. Each meta-resource describes the respective resource and may contain the code or an API required to transform the resource to the format required by the application. End users or other types of clients may browse the WWH catalog via a browsing API or other type of browsing interface in order to obtain information about meta-resources, and WWH applications may query it for information about how to access the data. As noted above, the WWH catalog is assumed to be distributed across multiple data zones and their respective YARN clusters. Such a distributed arrangement helps to provide security and privacy for the underlying data resources.

Although distributed implementations of the WWH catalog are advantageous in some embodiments, it is possible in other embodiments for the WWH catalog to be implemented in only a single cluster of a WWH platform. Other alternative implementations may include distributed implementations in which the WWH catalog is distributed over only a subset of the clusters of a WWH platform, rather than over all of the clusters of the WWH platform.

The WWH platform and its associated WWH catalog in illustrative embodiments implement a recursiveness property that allows a given distributed application initiated on one of the YARN clusters to initiate additional applications on respective additional ones of the YARN clusters. Those additional applications can similarly initiate more applications on other ones of the YARN clusters different than the YARN clusters on which the additional applications were initiated. In this manner, a distributed application can be executed utilizing local data resources of multiple YARN clusters while preserving the privacy of each of the YARN clusters in its local data resources.

In some embodiments, security measures are deployed that prevent the data zones from being accessible to the outside world. For example, firewalls, routers and gateways may prevent public access to a cluster of a given data zone, allowing access to the cluster only from within a certain access point. The WWH platform in illustrative embodiments is configured to allow such "hidden" data zones to take part in both sharing data and computation.

The execution of a WWH application can be represented in some embodiments as a tree or a directed graph. In such an arrangement, each data zone participating in the execution of the application may be viewed as having two roles: (1) it receives a request to execute an application from a client, and (2) it can send requests for execution to other data zones, acting like a client. Role (1) can be represented as a "parent" node in the graph, and role (2) can be represented as an edge from a parent node to one or more "child" nodes. Each data zone may therefore be represented as the parent node of one or more child nodes, but may also be represented as the child node of another parent node representative of another data zone. A given parent node may not have access to data resources needed by a given application, but one or more of its associated child nodes may have access to those resources. The structure of the tree or directed graph representative of a given WWH application can be made visible with appropriate permissions via the distributed WWH catalog.

A WWH platform configured to run applications across multiple clusters associated with respective distinct data zones is advantageous in terms of both privacy and performance. Privacy is provided in that an application submitted to an initial cluster corresponding to a specific data zone accesses the data local to that data zone. The results of the application execution in the initial cluster may be transferred to other clusters corresponding to respective other data zones, but such processing results are typically aggregated and therefore need not include any private information. Furthermore, the recursiveness property mentioned above can in some embodiments be configured so as to hide even the knowledge of which of the clusters participate in the application execution. For similar reasons, performance is greatly improved. Usually raw data stays in its original location and only the results which are of much smaller size may be transferred between clusters. This contributes to improved performance both because of the inherent parallelism and the reduced data transfer between clusters.

As is apparent from the above, the overall privacy and efficiency of the WWH platform is maintained in some embodiments by adhering to local processing within clusters and their associated data zones. In order to keep the processing local, the WWH catalog includes meta-resources that direct the computation to the cluster where the data is stored, such that the computation moves and the data does not.

The WWH platform in illustrative embodiments provides significant advantages relative to conventional systems. For example, the WWH platform in some embodiments is oblivious to the particular local file systems utilized in the respective YARN clusters. Moreover, the WWH platform keeps local raw data private within each of the clusters, does not need a centralized controller or scheduler, and is not limited to use with only the MapReduce framework but is more generally suitable for use with any of a wide variety of frameworks that are supported by YARN.

The WWH platform utilizes a distributed WWH catalog having instances accessible to respective ones of the YARN clusters, and is thus agnostic to where exactly the data resides, and its exact format, and does not require a global file system.

The WWH platform is strongly privacy aware. It supports and encourages local processing of local data and provides simple ways for sending intermediate processing results which do not contain private information between clusters.

The WWH platform provides similar advantages for other aspects of Governance, Risk and Compliance (GRC). For example, by pushing processing closer to where the data is located, the WWH platform facilitates enforcement of policies relating to governance, management of risk, and compliance with regulatory requirements, all at the local level.

The WWH platform supports multiple data zones. A data zone is illustratively a distinct YARN cluster with its own local data. Such a data zone will usually execute a YARN application such as a MapReduce application on its local data. The WWH platform provides a framework which spans across multiple data zones, and enables the combination of processing results based on local data resources of the respective data zones in a global manner. Thus, the WWH platform provides and encourages cooperation between different data zones. However, the WWH platform does not encourage moving raw data between data zones, for both performance and privacy reasons, as well as for other related reasons such as the above-noted facilitation of GRC at the local level.

The WWH platform in some embodiments has an open architecture in the sense that any YARN cluster can join the WWH platform, and therefore the WWH platform in such an embodiment does not require any single centralized controller. Every participating YARN cluster is in control of the data it wishes to share with the outside world. An authorized external client can connect to any data zone supported by the WWH platform and there is no single entry point.

The WWH platform can be illustratively implemented utilizing YARN applications. For example, when a client wishes to run a WWH application it contacts a first one of the clusters, and runs a YARN application on that cluster. When other clusters need to be contacted, one or more containers of the first cluster act like respective clients for the other clusters, and run YARN applications on those other clusters. Thus in each individual cluster the distributed WWH application is seen as an individual YARN application and YARN itself is not aware of the multiple data zone aspects of the WWH application or the WWH platform.

Like YARN itself, the WWH platform in some embodiments is functionally separated into a platform layer and a framework layer. The WWH framework layer can be configured to support WWH frameworks for executing WWH applications that utilize any of a wide variety of underlying YARN frameworks. A developer can write WWH frameworks, and clients will be able to use those WWH frameworks, in a manner similar to how YARN frameworks such as MapReduce or Spark are utilized on single clusters. For example, some embodiments of WWH platforms described herein are provided with a WWH framework for running MapReduce applications in different data zones associated with respective multiple YARN clusters and using a global reducer in a particular YARN cluster to compute the final results. Alternatively, the global reducer can be implemented at least in part outside of the YARN clusters, such as within a given one of the WWH nodes.

Additional details regarding illustrative embodiments of a WWH platform will now be described with reference to FIGS. 4 through 7.

In these embodiments, it is assumed that a WWH application comprises executable code that is configured to process a set of location-dependent data resources using a set of distributed services provided by the WWH platform.

The location-dependent data resources can include Big Data or other types of data subject to processing using distributed analytics applications.

Like YARN applications utilizing frameworks such as MapReduce and Spark, WWH applications can utilize corresponding WWH frameworks denoted herein as WWH-MapReduce and WWH-Spark. The WWH applications illustratively include client applications that utilize these and other WWH frameworks. Any framework supported by YARN can have a corresponding WWH framework implemented using the techniques disclosed herein.

Software developers associated with the WWH platform illustratively include the above-noted clients that create applications which benefit from the distributive nature of the WWH platform using the WWH frameworks. For example, such a client may comprise a developer that writes an application comprising Mapper, Reducer and GlobalReducer components and then submits a job using a WWH-MapReduce-GlobalReduce framework.

Other developers include platform developers that write the components which are considered integral parts of the WWH platform, and framework developers that develop the WWH frameworks to be utilized by clients in creating their applications. Examples of WWH frameworks include the above-noted WWH-MapReduce, WWH-Spark and WWH-MapReduce-GlobalReduce frameworks.

Figure 4:
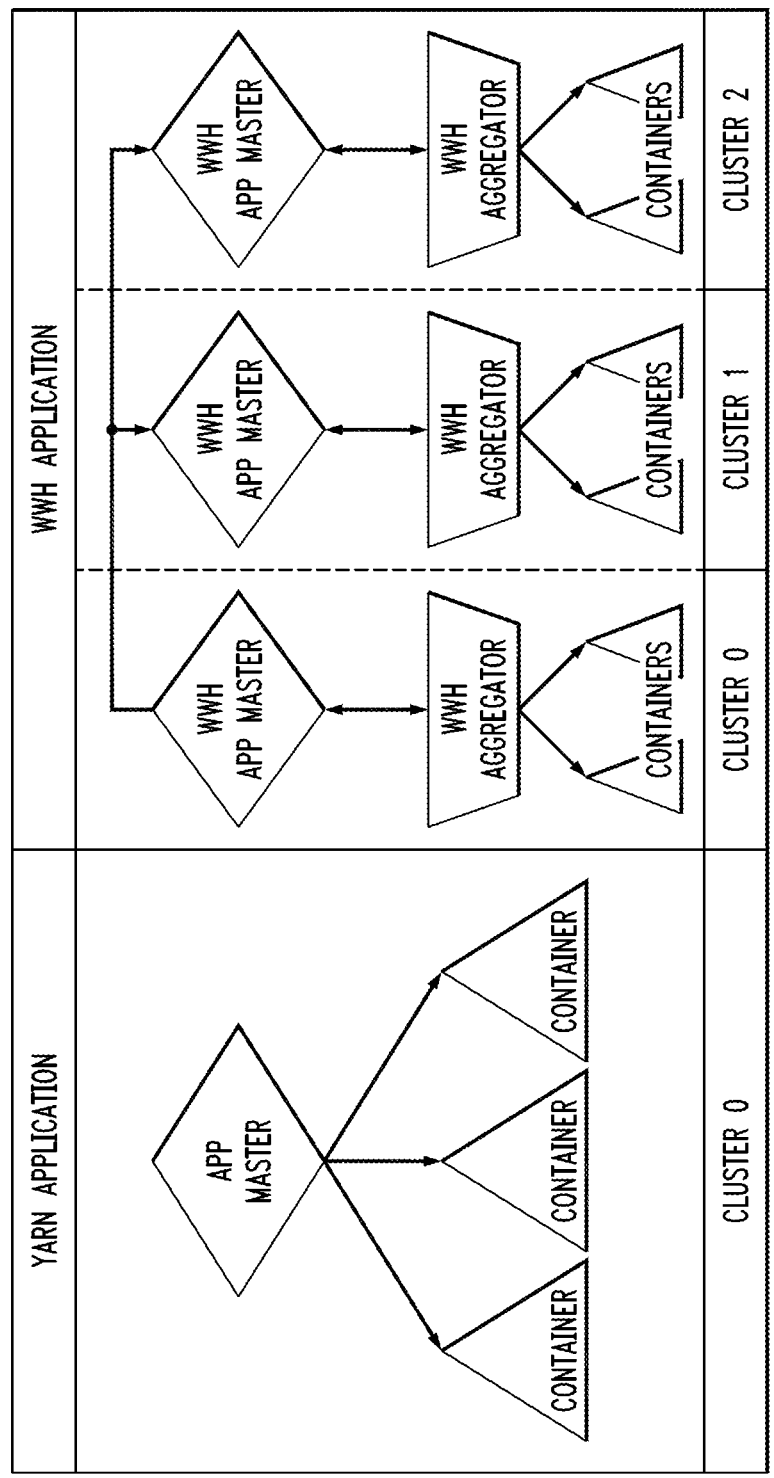
FIG. 4 compares a YARN application running on a single cluster with a distributed WWH application running on multiple clusters in an illustrative embodiment.

Referring now to FIG. 4, a YARN application running on a single cluster denoted Cluster 0 is compared to a WWH application running on multiple clusters including Cluster 0 and two additional clusters denoted Cluster 1 and Cluster 2.

As illustrated in the figure, the YARN application comprises an application master that controls the execution of a corresponding application using multiple containers in the same cluster. The WWH application comprises multiple application masters running on respective ones of Cluster 0, Cluster 1 and Cluster 2. Each of the application masters of the WWH application is associated with an application running in the corresponding cluster and includes a corresponding WWH aggregator. Each of the WWH aggregators is controlled by its application master and utilizes multiple containers within its cluster in conjunction with execution of the associated application.

A given container illustratively comprises a collection of physical resources on a single data processing node, such as memory (e.g., RAM), CPU cores, and disks. There can be multiple containers on a single node, or a single large container on that node. Each node of a given cluster is assumed to comprise one or more containers of a designated minimum memory size (e.g., 512 MB or 1 GB). The application master can request one or more containers as a multiple of the minimum memory size.

The multiple containers utilized by one of the WWH aggregators on a given one of the clusters correspond to respective local data resources that are locally accessible within that cluster. The WWH aggregator is illustratively configured to request initiation of one or more additional applications on one or more respective other ones of the clusters with the additional application utilizing remote data resources locally accessible within the one or more other clusters. The WWH application master component corresponding to the WWH aggregator may be configured to access a resolving API or other type of resolving interface of the distributed WWH catalog instance of the corresponding cluster in order to determine for each of the plurality of data resources to be utilized by the application whether the data resource is a local data resource or a remote data resource.

Although each WWH application master in this embodiment is shown as interacting with only a single WWH aggregator, this is by way of illustrative example only and in other embodiments a given WWH application master can be configured to control multiple WWH aggregators.

Also, the particular separation between WWH application master and WWH aggregator components is exemplary only, and in other embodiments a given WWH aggregator or its associated functionality can be incorporated at least in part within the corresponding WWH application master rather than external to that WWH application master as illustrated in FIG. 4 and other embodiments herein.

The WWH application masters are also referred to herein as respective WWH-ApplicationMaster ("WAM") components. Such components are assumed to comprise WWH platform components that are "private" and therefore not modifiable by framework developers. These private components are assumed to be defined and implemented by the platform developers.

Other WWH platform components considered private in illustrative embodiments include WWH Node Manager and WWH Catalog Service. These and other WWH platform components will be described in greater detail below.

The WWH aggregators are also referred to herein as WWH-Aggregator components. Such components are assumed to comprise WWH platform components that are "exposed" and therefore are modifiable by framework developers. For example, a framework developer can create an extension to an abstract WWH-Aggregator class. An example of such an extension for a WWH-MapReduce framework is denoted herein as WWH-Aggregator-For-MapReduce. The role of the WWH-Aggregator is generally to aggregate processing results from multiple clusters and to present the aggregated processing results to an end user or other client that initiated the distributed application.

It should be noted that references herein to private and exposed WWH platform components are made by way of example only, and in other embodiments additional or alternative components may be in respective ones of the private and exposed categories. Also, in other embodiments, all or substantially all WWH platform components may be designated as private, or all or substantially all WWH platform components may be designated as exposed.

A given WWH-Application illustratively comprises a set of executable components, such as binaries, classes and other components, including the WWH-ApplicationMaster class and one or more derivatives of the WWH-Aggregator class bundled with associated arguments for a Resource Manager of the corresponding YARN cluster in which the WWH-Application is initiated. These components collectively permit initiation of the corresponding distributed application.

A given WWH-Aggregator may utilize the containers, files and other data resources that are local to the particular cluster on which it runs. In addition, the given WWH-Aggregator may recursively request the execution of a remote WWH-Aggregator in a remote cluster. This may be achieved at least in part utilizing a Representational State Transfer (REST) application programming interface (API) of the corresponding WWH-ApplicationMaster.

As noted above, client applications can be configured to utilize one of a plurality of available WWH frameworks, such as one of the WWH-MapReduce, WWH-Spark and WWH-MapReduce-GlobalReduce frameworks. The latter WWH framework and a corresponding WWH global MapReduce application flow utilizing that framework will be described in greater detail below. The global MapReduce application is just one example of a distributed WWH application that can be executed using a WWH platform as disclosed herein.

Figure 5:
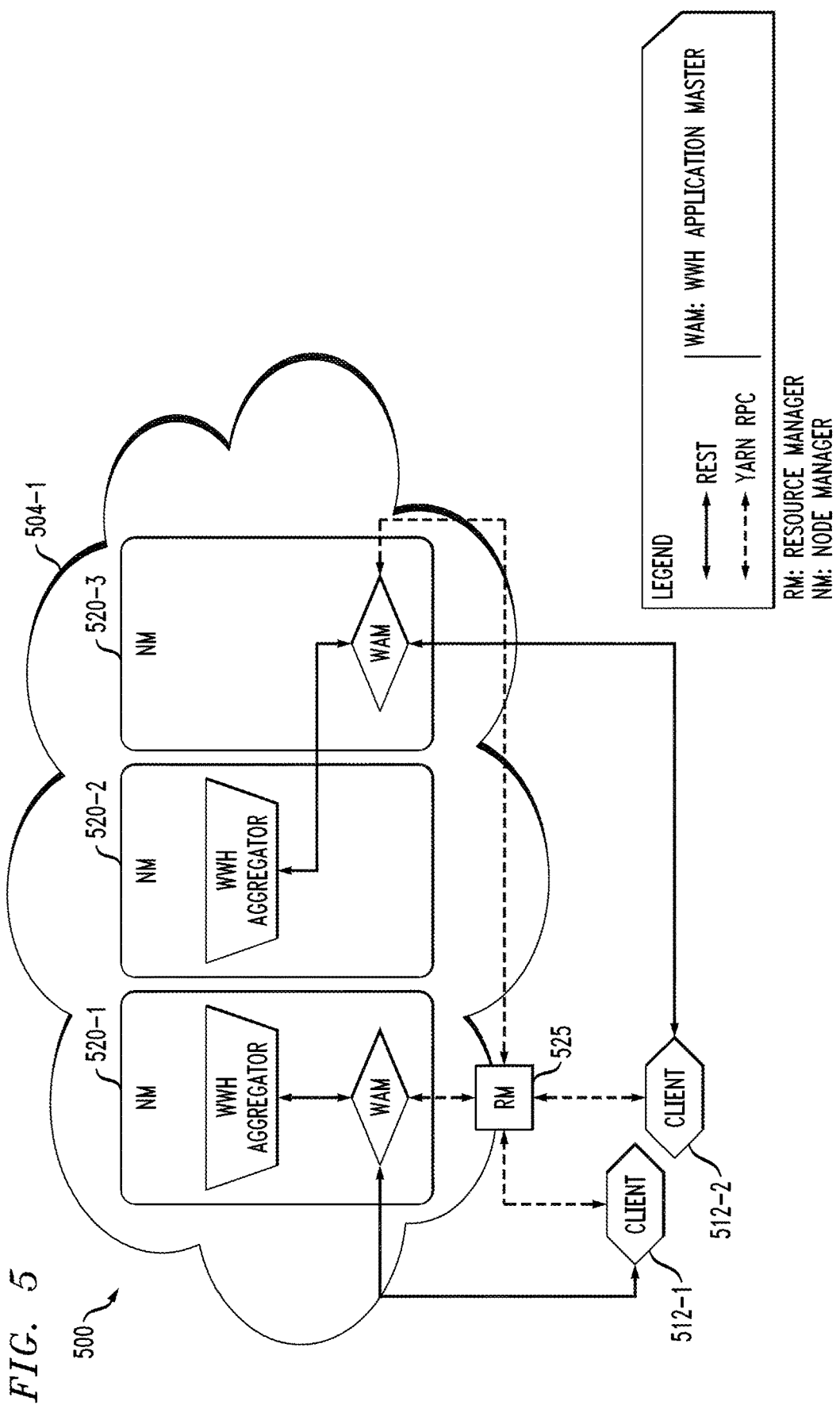
FIGS. 5 and 6 illustrate example arrangements of WWH platform components in respective illustrative embodiments.
Figure 6:
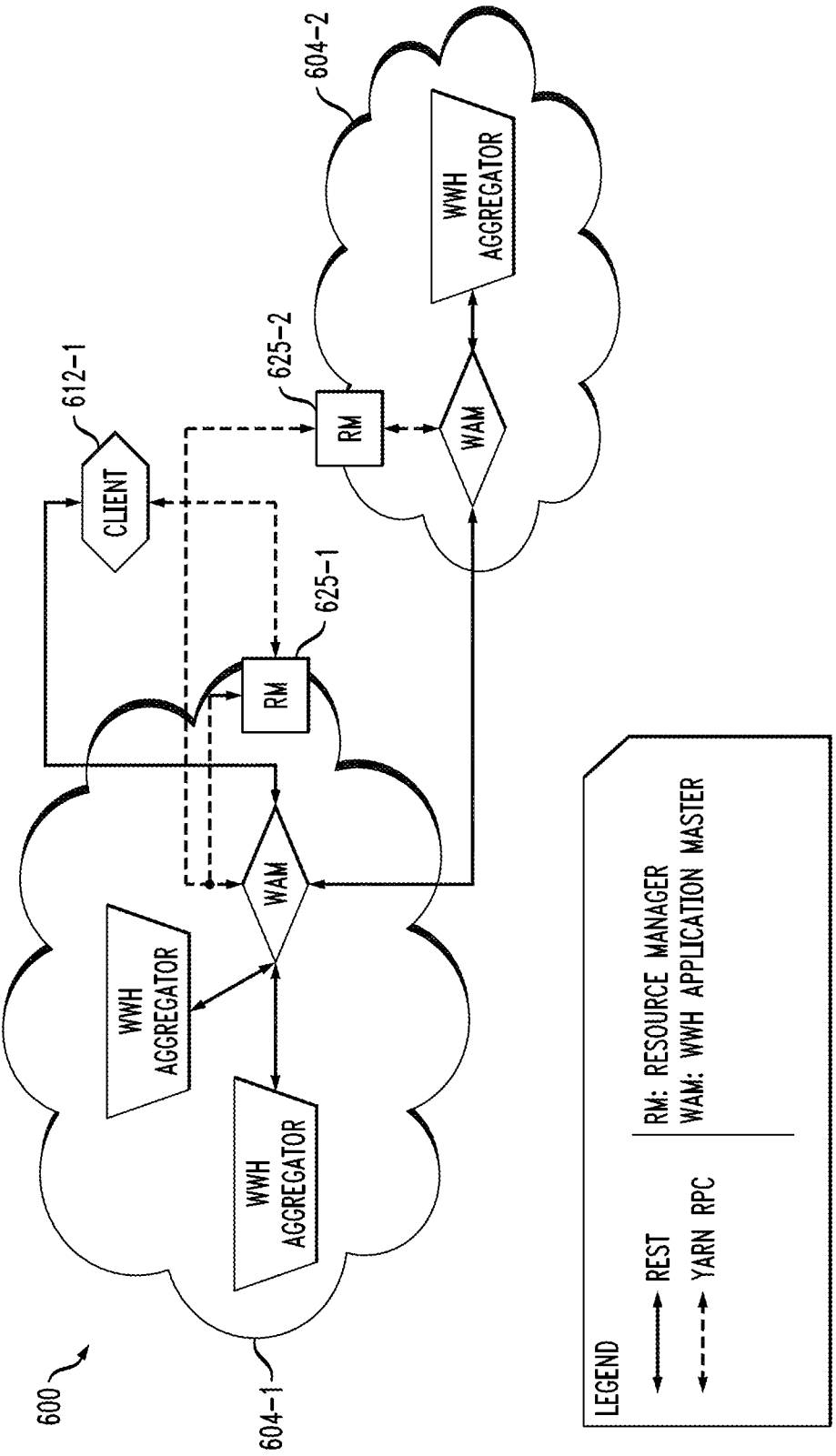

FIGS. 5 and 6 illustrate example arrangements of WWH components in respective illustrative embodiments.

Referring initially to FIG. 5, a portion 500 of a WWH platform is shown. The portion 500 includes only a single YARN cluster 504-1, although it is to be appreciated that the WWH platform is assumed to comprise multiple additional clusters that are not explicitly shown in the figure. Clients 512-1 and 512-2 interact with the cluster 504-1. The cluster 504-1 comprises a plurality of distributed data processing nodes having respective node managers (NMs) 520-1, 520-2 and 520-3. The cluster 504-1 has an associated resource manager (RM) 525. The resource manager 525 is assumed to comprise a YARN resource manager. It is responsible for allocating resources and scheduling of containers within its corresponding cluster 504-1.

A given one of the node managers 520 manages a corresponding one of the data processing nodes of the cluster 504-1. This includes keeping up-to-date with the resource manager 525, managing the life-cycle of application containers, monitoring resource usage of individual containers, monitoring node health, and managing logs and other auxiliary services that can be utilized by YARN applications.

On startup, the given node manager registers with the resource manager 525, and then sends heartbeats with its status and waits for instructions. Its primary goal is to manage application containers assigned to it by the resource manager. For each container there is a single node manager that is responsible for its lifecycle.

In this embodiment, clients 512-1 and 512-2 communicate with respective WWH application master (WAM) components running on data processing nodes having node managers 520-1 and 520-3. This communication occurs via REST APIs of the respective WAM components. The clients 512 and WAM components also communicate with the resource manager 525 via YARN remote procedure calls (RPCs) as illustrated. It should be noted that the node managers 520 are responsible for the execution of the application processes within their corresponding cluster 504-1.

FIG. 6 shows a portion 600 of a WWH platform in another illustrative embodiment. In this embodiment, first and second YARN clusters 604-1 and 604-2 have associated resource managers 625-1 and 625-2. A client 612-1 interacts with a WAM component in cluster 604-1 via a REST API of the WAM component in that cluster. That WAM component interacts with two WWH aggregators also running in the cluster 604-1, and with another WAM component implemented in cluster 604-2. The other WAM component implemented in cluster 604-2 interacts with a single WWH aggregator also running in the cluster 604-2. The resource manager 625-1 communicates with the client 612-1 and the WAM component of cluster 604-1 via YARN RPCs. Similarly, the resource manager 625-2 communicates with the WAM components in respective clusters 604-1 and 604-2 via YARN RPCs. Communications between the WAM components and between a given one of the WAM components and its corresponding WWH aggregator(s) are carried out via the REST API of the given WAM component.

Figure 7:
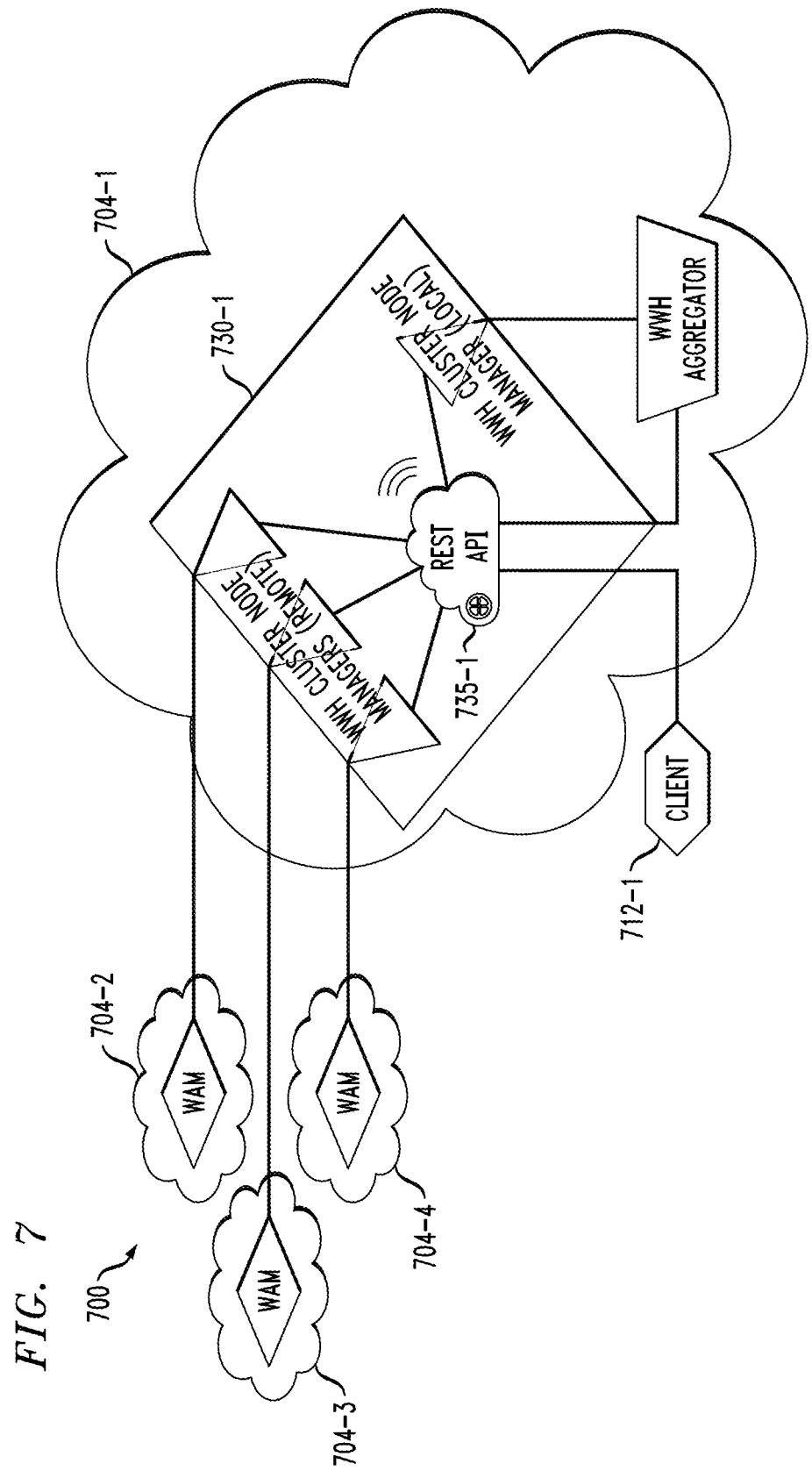
FIG. 7 shows a more detailed view of a WWH application master in a given cluster and its interaction with similar components in respective additional clusters.

FIG. 7 shows a more detailed view of a WAM component in a given cluster and its interaction with similar components in respective additional clusters. In this illustrative embodiment, a portion 700 of a WWH platform comprises YARN clusters 704-1, 704-2, 704-3 and 704-4. It is assumed that each of the YARN clusters has an associated resource manager, although the resource managers are not explicitly shown in the figure. The YARN cluster 704-1 comprises a WAM component 730-1. The cluster 704-1 is the local cluster of the WAM component 730-1, and the other clusters 704-2, 704-3 and 704-4 are respective remote clusters relative to the local cluster 704-1.

The WAM component comprises a REST API 735-1, a WWH cluster node manager for its local cluster 704-1, and additional WWH cluster node managers for respective ones of the remote clusters 704-2, 704-3 and 704-4. Each of the remote clusters 704-2, 704-3 and 704-4 includes a WAM component that is assumed to be configured in a manner similar to WAM component 730-1 of local cluster 704-1.

A client 712-1 interacts with WAM component 730-1 via the REST API 735-1. The WAM component 730-1 communicates with the WWH aggregator of its local cluster 704-1 via the REST API and the local cluster node manager. Also, the WWH aggregator is configured to interact with the local and remote cluster node managers. For example, the WWH aggregator can communicate with the local and remote cluster node managers of the WAM component 730-1 via the REST API 735-1. Accordingly, in this embodiment, the REST API 735-1 allows both the client 712-1 and the WWH aggregator of the WAM component 730-1 to communicate with the local and remote cluster node managers.

The WAM component 730-1 is also referred to herein as a WWH-ApplicationMaster, and as previously described is assumed to be a private component of the WWH platform that cannot be altered by framework developers. The WWH-ApplicationMaster is a YARN ApplicationMaster, and is the main process which provides WWH-related services in this embodiment. It contains the REST API 735-1, which allows external clients to access the corresponding WWH-Application, and facilitates job distribution between the different components of the WWH-Application as utilized by the WWH-Aggregator. The local and remote cluster node managers of the WWH-ApplicationMaster collectively comprise a set of WWH-ClusterNodeManager threads that are created on demand and are responsible for the actual distribution and monitoring of jobs for the local and remote clusters. The WWH-ApplicationMaster is also responsible for communication between clusters. This is achieved in the present embodiment by using the remote cluster node managers each behaving as a YARN client to a corresponding remote cluster.

A WWH-ClusterNodeManager is also assumed to be a private component of the WWH platform. As noted above, the WWH-ClusterNodeManager is a thread inside the WWH-ApplicationMaster. It can be either local or remote depending on whether it communicates with the resource manager in the same cluster as the WAM component or with the resource manager in a remote cluster.

A local WWH-ClusterNodeManager is responsible for executing the local application via the execution of a supplied WWH-Aggregator and for updating the WWH-ApplicationMaster REST API so that recursively the parent or invoking WWH-Aggregator will be able to fetch back the processing results.

A remote WWH-ClusterNodeManager recursively serves as a client to the remote WWH-ApplicationMaster and passes the jobs through its remote REST API.

The WWH-ClusterNodeManager components are created on demand when a job is submitted to the WWH-ApplicationMaster. Note that since the WWH-ClusterNodeManager is a YARN client, the communication between the WWH-ClusterNodeManager and the other clusters is in accordance with YARN protocols.

As mentioned previously, the WWH-Aggregator component is assumed to be an exposed component of the WWH platform, and is therefore subject to modification by framework developers. The WWH-Aggregator is illustratively implemented as a child container of the WWH-ApplicationMaster. It may use the containers, files and other local data resources of the cluster it is running in. Additionally or alternatively, it may recursively request execution of a remote WWH-Aggregator in a remote cluster using the REST API of the WWH-ApplicationMaster. The WWH-Aggregator is responsible for aggregating the processing results of submitted jobs and producing a meaningful result for the client. Each WWH-Aggregator illustratively has an associated WWH-ApplicationMaster container that is responsible for that WWH-Aggregator.

It is to be appreciated that the particular arrangements of WWH platform components illustrated in FIGS. 4 through 7 are presented by way of illustrative example only. Numerous other arrangements of additional or alternative components can be used to implement a multi-cluster distributed data processing platform in other embodiments.

Additional examples of software stack arrangements for illustrative embodiments of multi-cluster distributed data processing platforms are shown in FIGS. 8 through 11.

Figure 8:
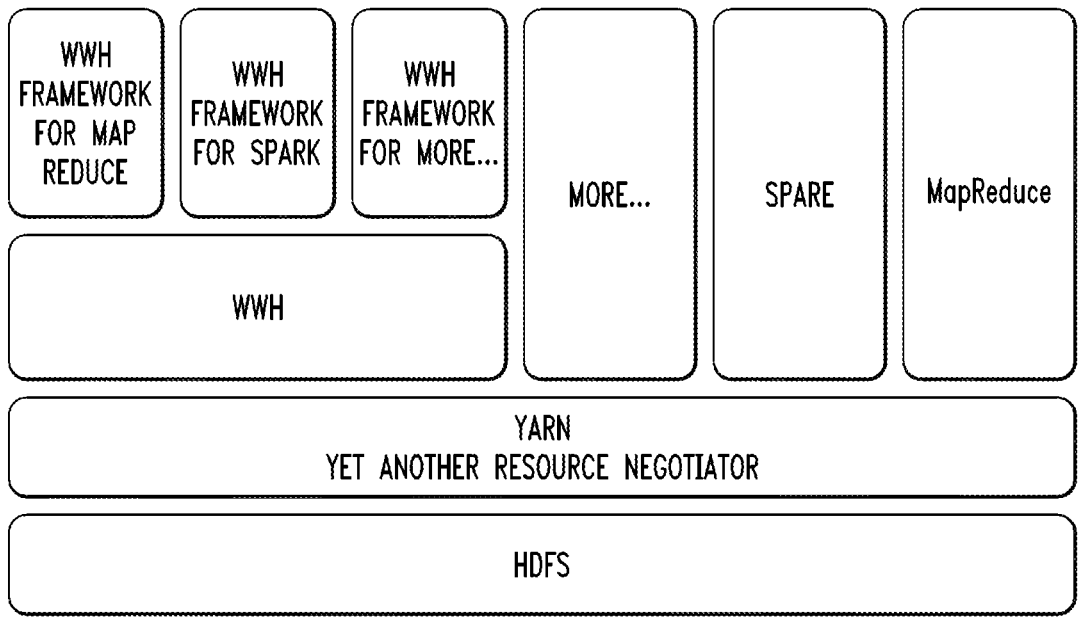
FIGS. 8 through 11 show example software stack diagrams of multi-cluster distributed data processing platforms in illustrative embodiments.

With reference now to FIG. 8, a given multi-cluster distributed data processing platform can comprise a YARN layer built over an underlying HDFS. The YARN layer supports YARN frameworks such as MapReduce and Spark, and possibly numerous others. It also supports a WWH framework that itself includes WWH-MapReduce and WWH-Spark frameworks, and possibly numerous other WWH frameworks.

Figure 9:
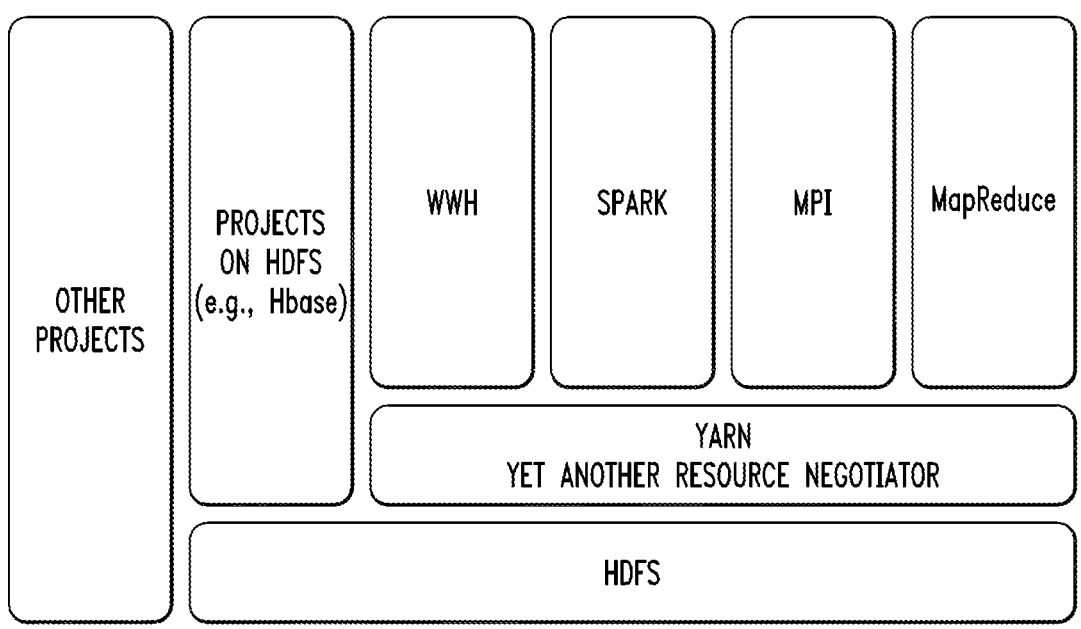
Figure 10:
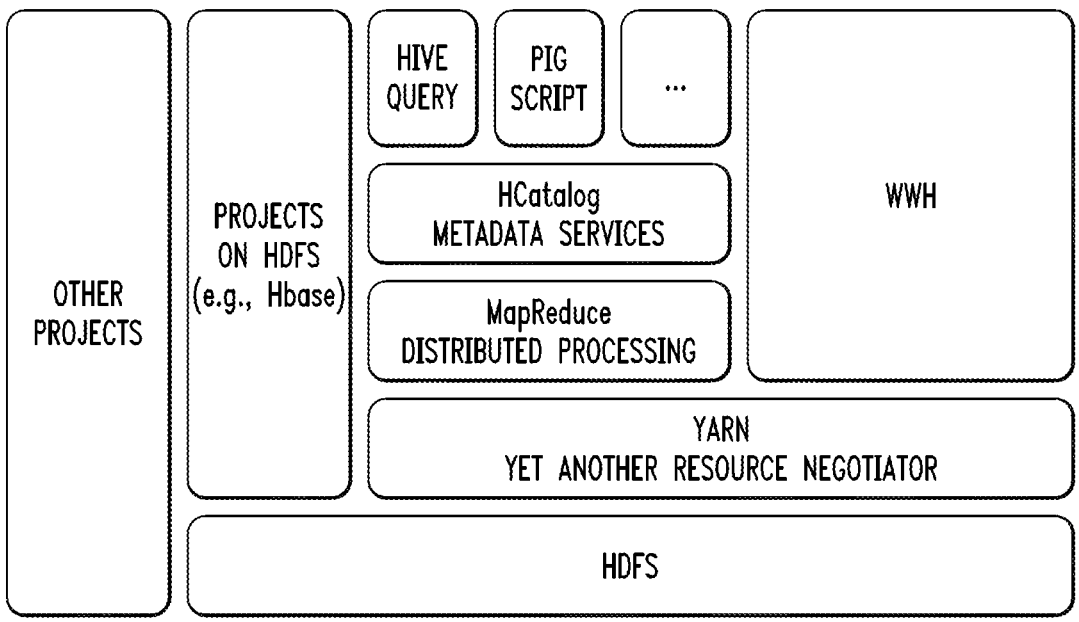
Figure 11:
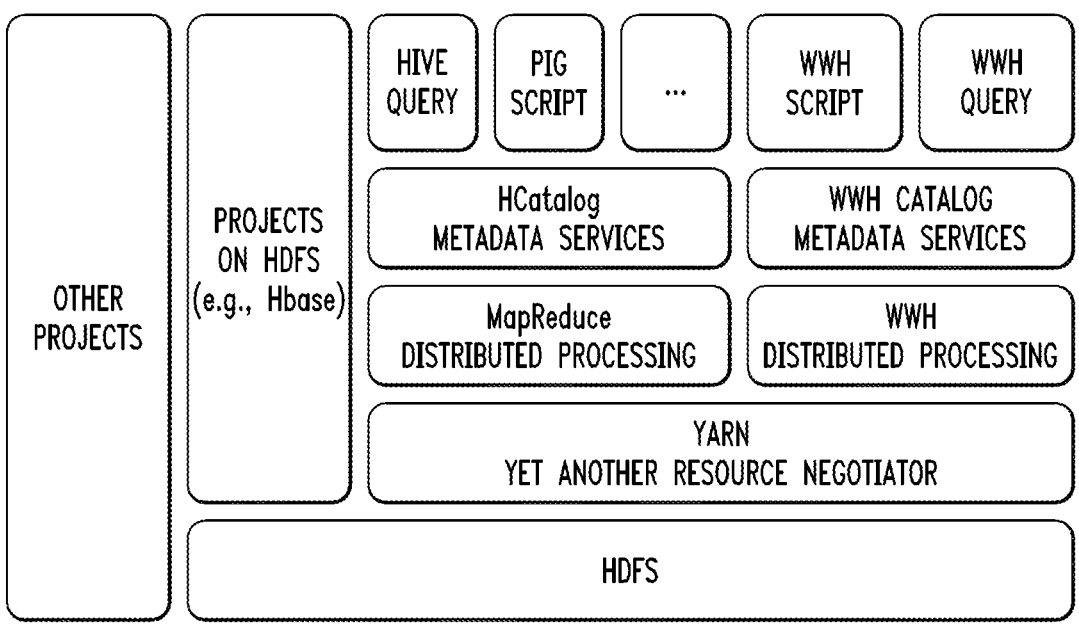

FIGS. 9, 10 and 11 show various alternative arrangements of software components that may be utilized in a software stack of a multi-cluster distributed data processing platform in other embodiments.

For example, with reference to FIG. 9, a YARN layer supports multiple frameworks including WWH, MapReduce, Spark and MPI, and makes use of an underlying HDFS. The HDFS can also support other projects, such as, for example, Hbase. Other projects not involving use of YARN or HDFS can also be implemented in the platform.

Another example platform software stack is illustrated in FIG. 10. In this embodiment, a YARN layer supports multiple frameworks including WWH and MapReduce distributed processing, and makes use of an underlying HDFS. The MapReduce distributed processing utilizes HCatalog metadata services to support Hive queries, Pig scripts and other functionality. The HDFS can also support other projects, such as, for example, Hbase. Other projects not involving use of YARN or HDFS can also be implemented in the platform.

With reference now to FIG. 11, a further example of a platform software stack is shown. In this embodiment, a YARN layer supports multiple frameworks including WWH distributed processing and MapReduce distributed processing, and makes use of an underlying HDFS. The MapReduce distributed processing utilizes HCatalog metadata services to support Hive queries, Pig scripts and other functionality. The WWH distributed processing utilizes WWHCatalog metadata services to support WWH queries and WWH scripts. Again, the HDFS can also support other projects, such as, for example, Hbase, and other projects not involving use of YARN or HDFS can also be implemented in the platform.

It is to be appreciated that the particular platform software stacks illustrated in FIGS. 8 through 11 are examples only, and numerous other multi-cluster distributed data processing platforms can be configured using respective alternative types and configurations of software components.

Figure 12:
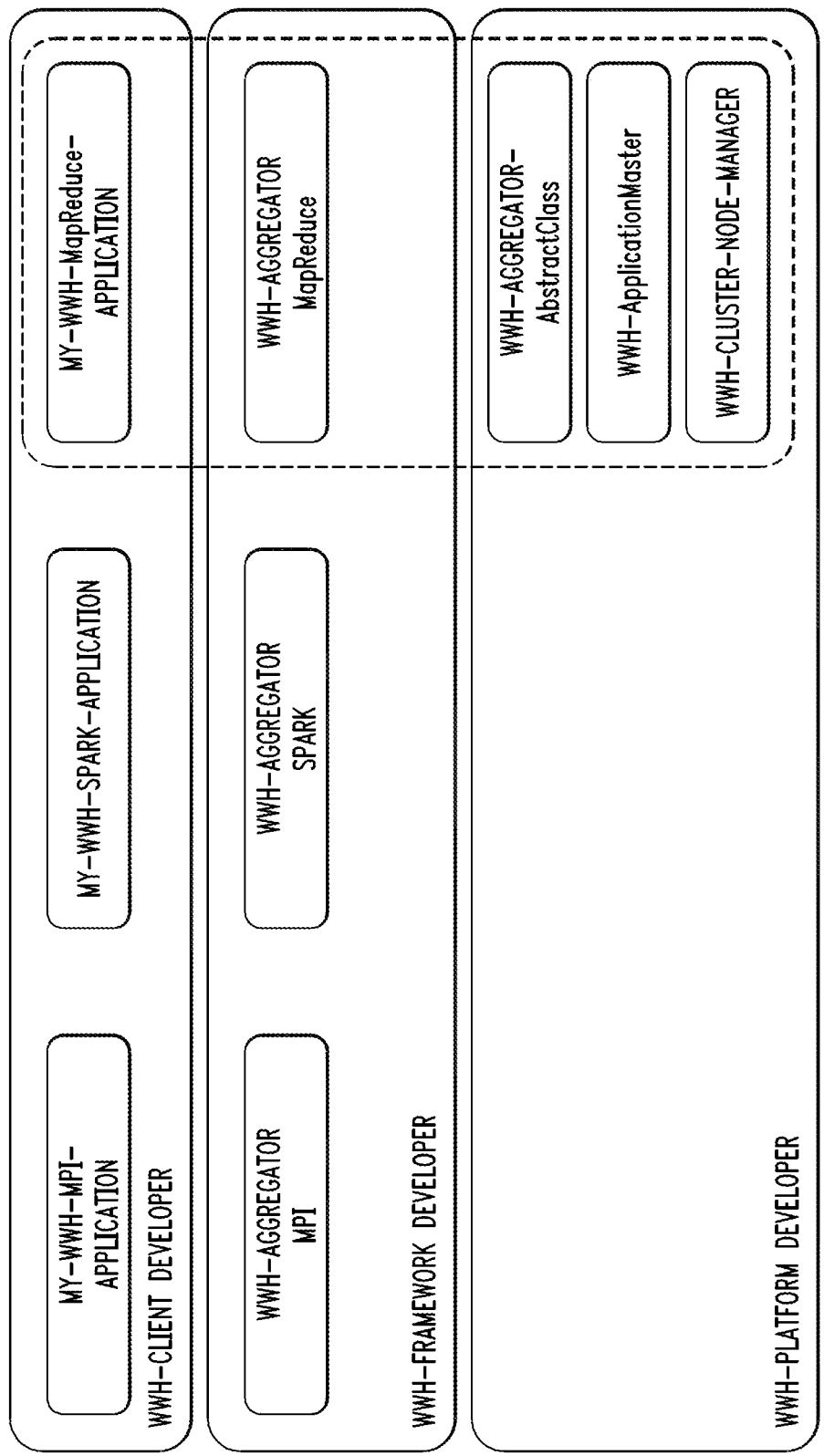
FIGS. 12 through 16 illustrate example operating configurations of multi-cluster distributed data processing platform components in illustrative embodiments.
Figure 13:
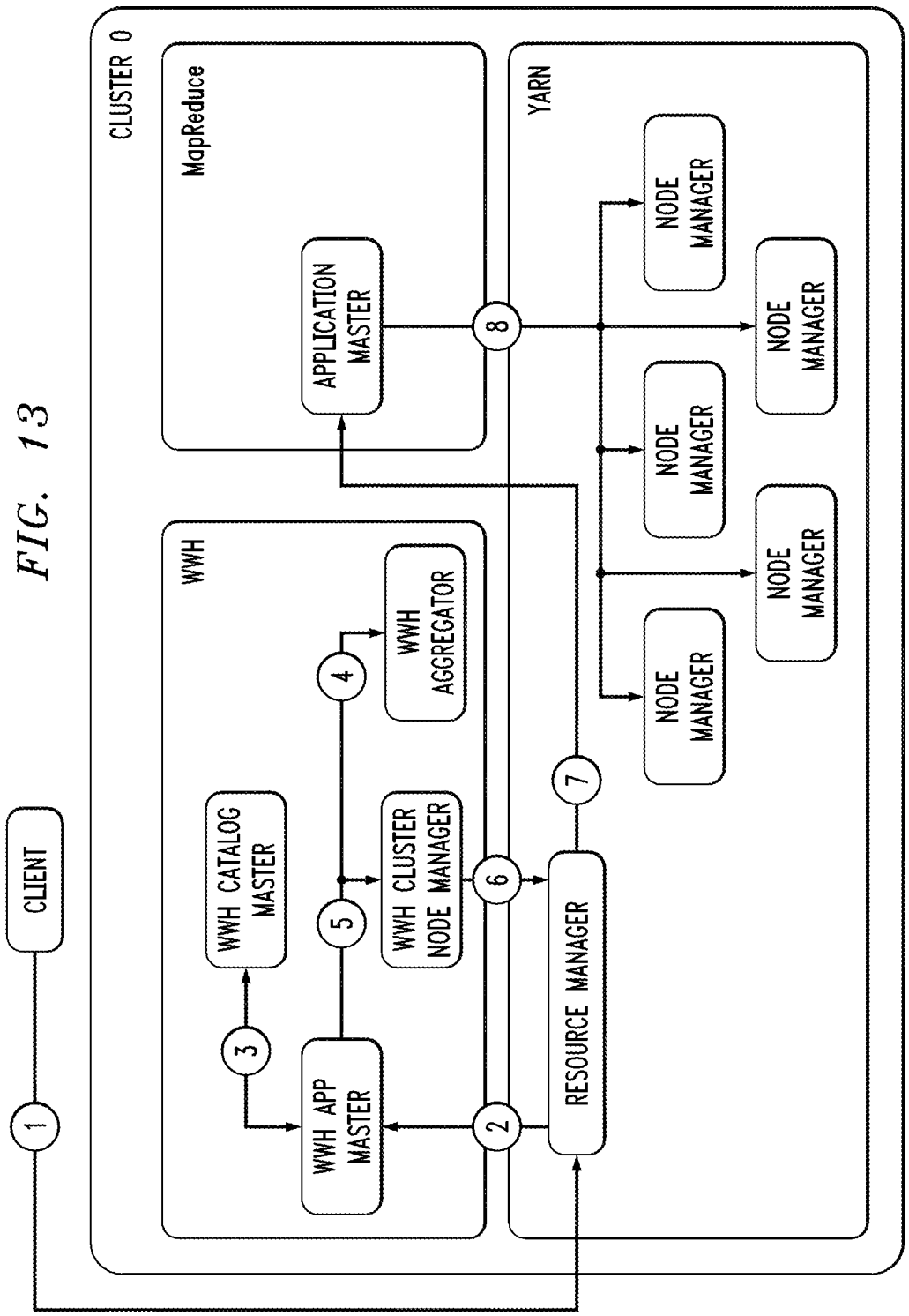
Figure 14:
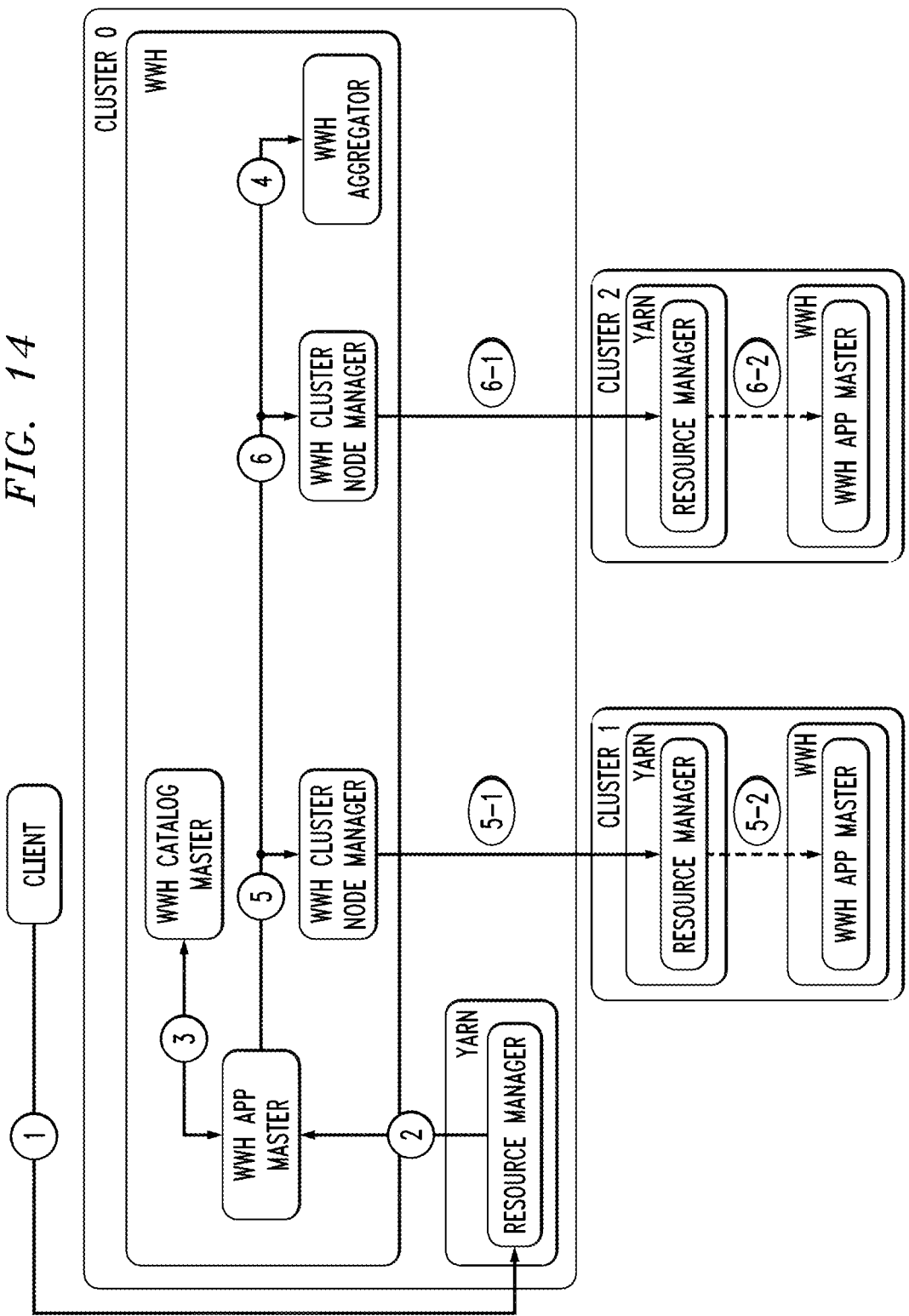
Figure 15:
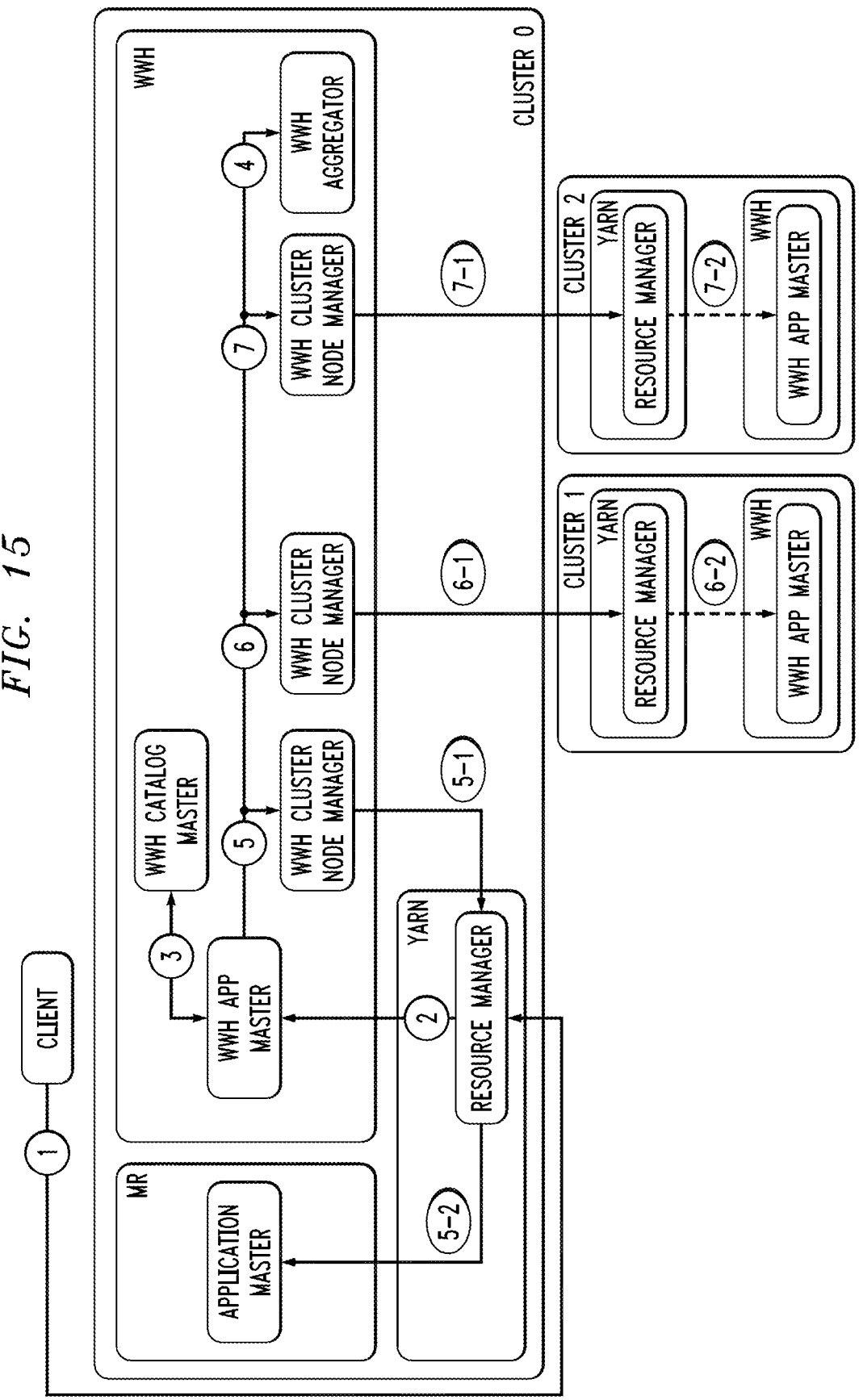

FIGS. 12 through 16 illustrate example operating configurations of multi-cluster distributed data processing platform components in illustrative embodiments. The circled numbers shown in FIGS. 13, 14 and 15 are indicative of example processing sequence flows utilized in these illustrative embodiments.

Referring initially to FIG. 12, example relationships between the portions of a given WWH implementation that are accessible to a WWH client developer, WWH framework developer and WWH platform developer are shown. In this embodiment, the WWH platform developer implements WWH-ApplicationMaster, WWH-ClusterNodeManager, and WWH-Aggregator-AbstractClass. The WWH framework developer implements WWH-AggregatorMapReduce, WWH-AggregatorSpark and WWH-AggregatorMPI. The WWH client developer implements My-WWH-MapReduceApplication, My-WWH-SparkApplication and My-WWH-MPIApplication. My-WWH-MapReduceApplication is a client-developed application that utilizes underlying framework and platform components including WWH-AggregatorMapReduce, WWH-AggregatorAbstractClass, WWH-ApplicationMaster and WWH-ClusterNodeManager, as illustrated.

With reference now to FIG. 13, an embodiment is illustrated in which all of the data resources required by an application submitted by a client are local resources within the cluster that initiates the application. In this embodiment, a YARN cluster comprises a single resource manager, and multiple node managers corresponding to respective data processing nodes of the YARN cluster.

The client in the FIG. 13 embodiment submits an application using the Global Map Reducer framework to Cluster 0 and all the data resources actually reside in Cluster 0 itself. First, the client submits an application to the Resource Manager residing in Cluster 0 (1), which creates an instance of the WWH Application Master (2) and passes to the WWH Application Master all the parameters received by the client, including the mapper, the local reducer, the global reducer, and the list of resources to be used. The WWH Application Master uses the Resolving API to communicate with the WWH Catalog Master, passing the list of resources to be used (3). Since all the resources are local in this embodiment, the WWH Catalog Master will return the actual address of the list of resources to the WWH Application Master. The WWH Application Master will then create an instance of the WWH Aggregator (4), to manage the collection of results from the WWH Cluster Node Managers and to execute the Global Reduce operation later on. Next, the WWH Application Master will create an instance of the WWH Cluster Node Manager (5) passing the mapper, the local reducer and the list of local resources. The WWH Cluster Node Manager just created will behave as a local client to the Resource Manager running in Cluster 0 itself, submitting a request for the execution of a MapReduce operation in Cluster 0 (6). The local Resource Manager in Cluster 0 will then create an instance of the Application Master (7). From this point on, the Application Master just created will behave as a normal YARN application (8). The Application Master will analyze the list of resources and then negotiate with the scheduler in the local Resource Manager of Cluster 0 the allocation of processing resources with the Node Managers.

FIG. 14 illustrates an embodiment in which the data resources required by an application submitted by a client are remote data resources in respective additional YARN clusters other than the YARN cluster that initiates the application. In this embodiment, the client submits an application in Cluster 0 and the data resources reside in Cluster 1 and Cluster 2. More particularly, the client submits an application to the Resource Manager residing in Cluster 0 (1), which creates an instance of the WWH Application Master (2), which then connects with the WWH Catalog Master (3) through the Resolving API. In this embodiment, the WWH Catalog Master returns a list of resources containing resources that reside in Cluster 1 and resources that reside in Cluster 2. The WWH Application Master then creates an instance of the WWH Aggregator (4) and then creates an instance of the WWH Cluster Node Manager for communicating with Cluster 1 (5) and an instance of the WWH Cluster Node Manager for communicating with Cluster 2 (6).

Optimizations have been done in the implementation where there is a single WWH Cluster Node Manager for communication between a given pair of clusters. In other words, should another application start in Cluster 0 that also has resources residing in Cluster 1, the system would not create another instance of the WWH Cluster Node Manager in Cluster 0, but would instead actually utilize the same instance already created. The WWH Cluster Node Managers then start an application in the clusters that they are connected to (5-1 and 6-1, respectively), and become a client of the Resource Managers in those respective clusters. The Resource Managers in Cluster 1 and Cluster 2 then create a WWH Application Master in their respective clusters (5-2 and 6-2) which will execute the application with the data resources in the respective clusters.

FIG. 15 illustrates an embodiment in which the data resources required by an application submitted by a client include both local resources within the YARN cluster that initiates the application and remote data resources in respective additional YARN clusters other than the YARN cluster that initiates the application. In this embodiment, the client submits an application request to the Resource Manager residing in Cluster 0 (1) that creates a WWH Application Master (2) that then connects with the WWH Catalog Master (3). The WWH Catalog Master then returns a list of resources residing in Cluster 0, a list of resources residing in Cluster 1, and a list of resources residing in Cluster 2. The WWH Application Master then creates a WWH Aggregator (4) and then creates a WWH Cluster Node Manager for each one of the clusters that has resources involved in this computation (5, 6 and 7). The WWH Cluster Node Managers then communicate with the Resource Managers residing in the respective clusters and submit respective applications to be started there (5-1, 6-1 and 7-1). The Resource Manager in Cluster 0 starts an Application Master (5-2) while the Resource Managers in the remote clusters start respective WWH Application Masters (6-2 and 7-2).

Figure 16:
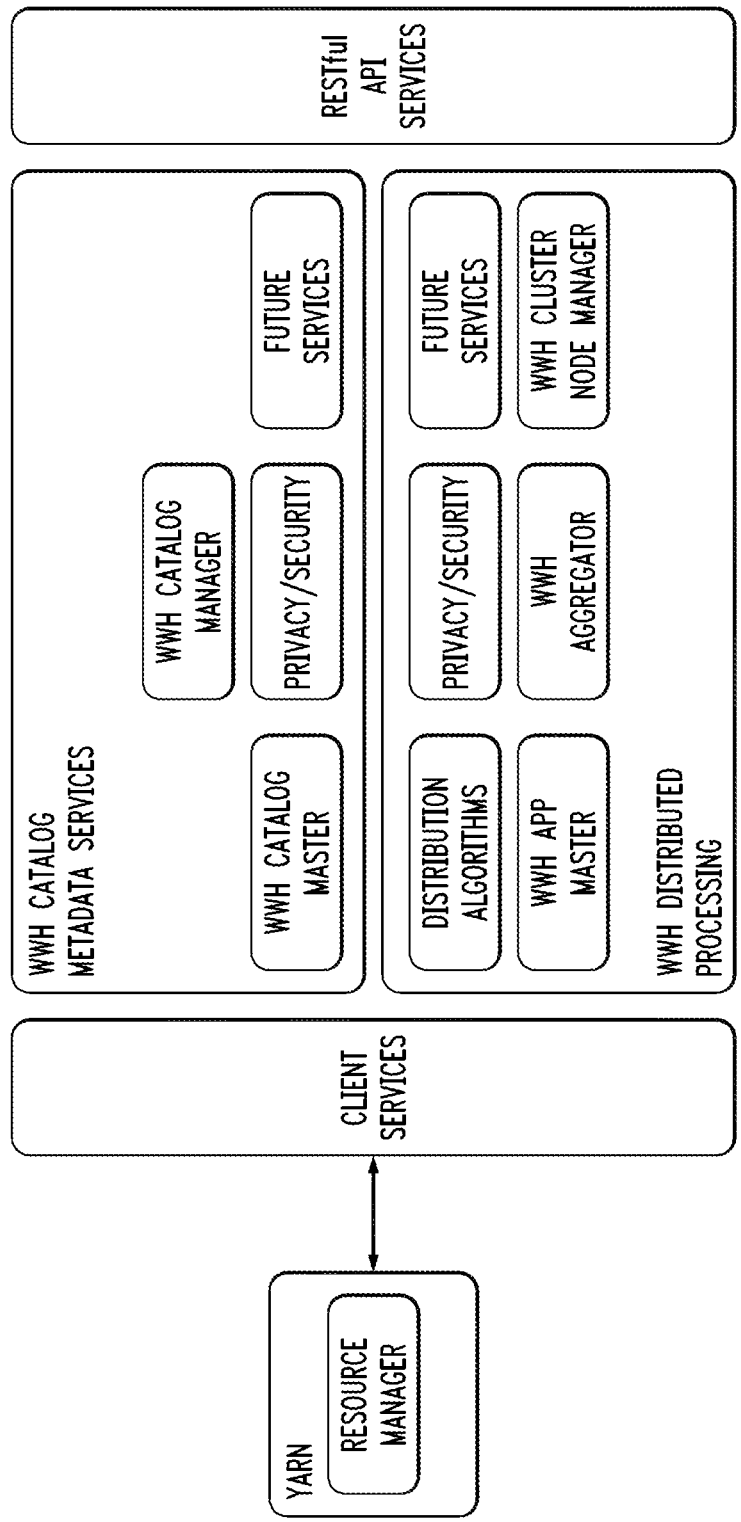

An example of one possible arrangement of WWH components in an illustrative embodiment is shown in FIG. 16. In this embodiment, a YARN cluster having a resource manager interacts via a client services interface with WWH distributed processing components and WWH catalog metadata services components. These WWH components are also accessible via RESTful API services as indicated.

Figure 17:
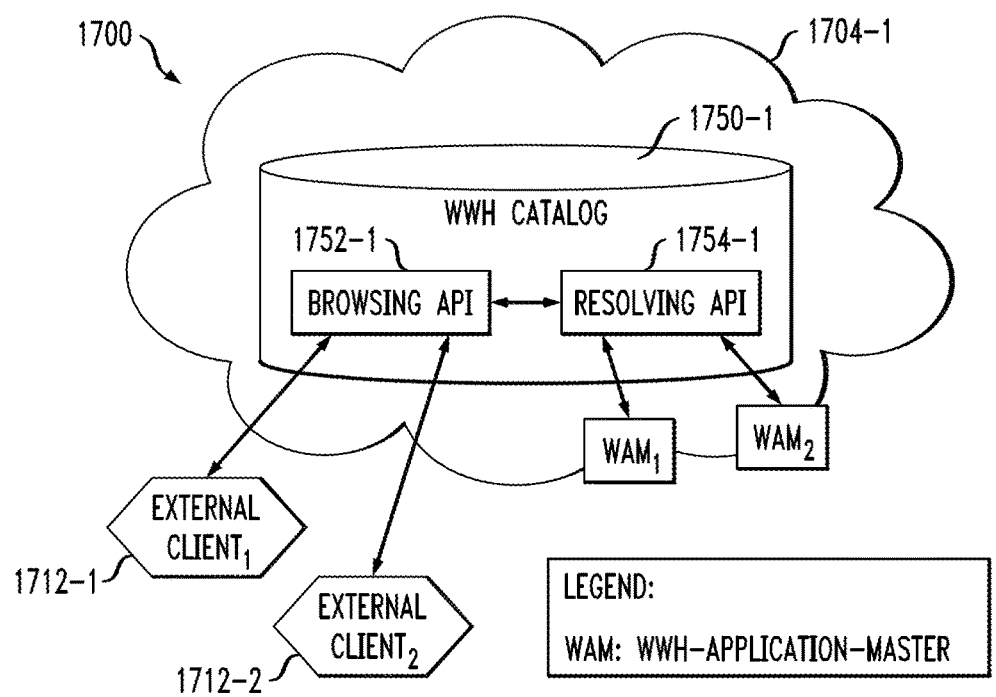
FIG. 17 shows one possible configuration of a WWH catalog of a multi-cluster distributed data processing platform in an illustrative embodiment.
Figure 18:
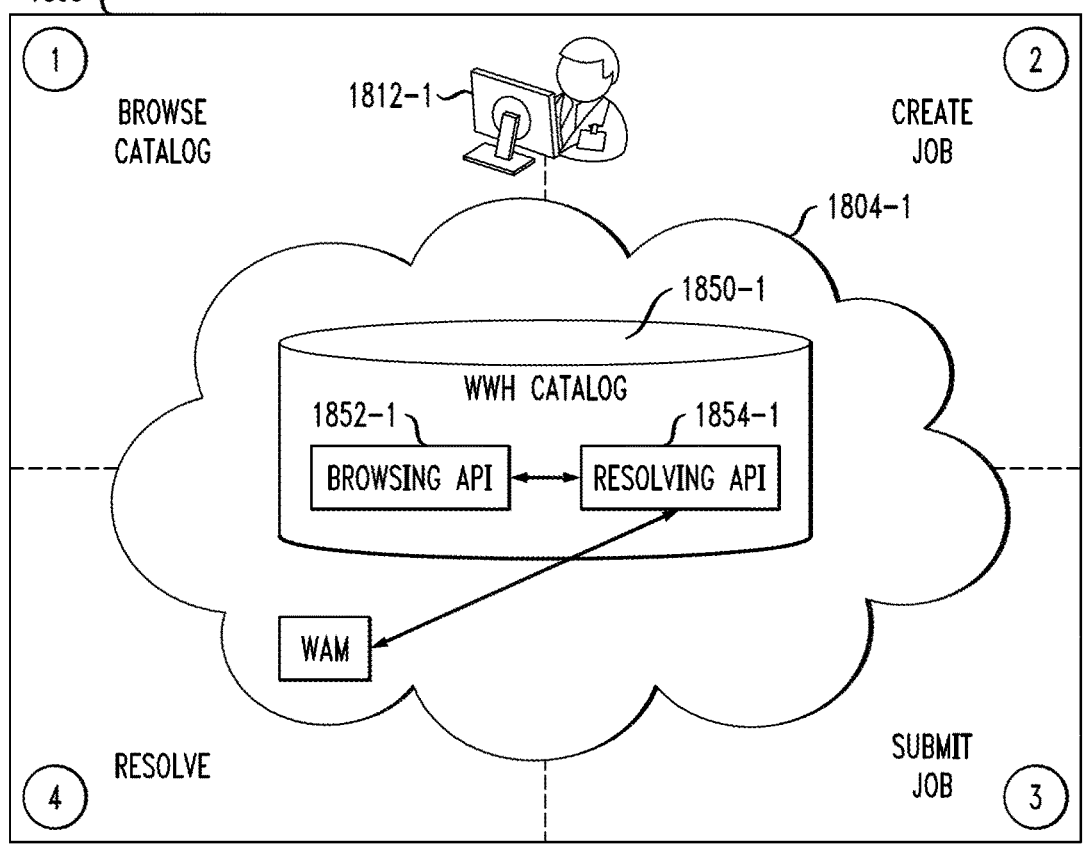
FIG. 18 illustrates a method of utilizing a WWH catalog of a multi-cluster distributed data processing platform in an illustrative embodiment.

Various features of possible configurations of the WWH catalog are illustrated in FIGS. 17 and 18.

Referring initially to FIG. 17, a portion 1700 of a multi-cluster distributed data processing platform in an illustrative embodiment comprises a first YARN cluster 1704-1. The cluster 1704-1 comprises a corresponding instance 1750-1 of a distributed WWH catalog. Although only a single cluster and corresponding WWH catalog instance is shown in this figure, it is assumed that similar instances of the distributed WWH catalog are implemented in respective ones of the other clusters of the multi-cluster distributed data processing platform. The clusters are further assumed to be associated with respective distinct data zones, with each of the clusters being configured to perform processing operations utilizing local data resources locally accessible within its corresponding data zone. The WWH catalog instance 1750-1 of cluster 1704-1 in combination with additional instances implemented for respective additional ones of the clusters collectively provide a distributed WWH catalog service with capability to resolve local or remote status of data resources in the data zones of each of the clusters responsive to requests from any other one of the clusters.

The WWH catalog instance 1750-1 of the cluster 1704-1 comprises a browsing API 1752-1 accessible to a plurality of clients including clients 1712-1 and 1712-2, and a resolving API 1754-1 accessible to one or more application master components of respective applications. The resolving API 1754-1 is also accessible to the browsing API 1752-1, and vice-versa, as indicated by the bidirectional connection between them in the figure.

The application master components in this embodiment more particularly comprise respective WAM components denoted $WAM_1$ and $WAM_2$. Each of these WAM components is assumed to be a YARN application master of a corresponding application running in the cluster 1704-1.

By way of example, a given one of the WAM components is illustratively configured to access the resolving API 1754-1 of the WWH catalog instance 1750-1 of cluster 1704-1 in order to determine for each of a plurality of data resources to be utilized by the associated application whether the data resource is a local data resource or a remote data resource relative to cluster 1704-1. The WWH catalog instance 1750-1 receives requests via its resolving API 1754-1 from the WAM components to identify for each of a plurality of data resources to be utilized by a corresponding application initiated in the cluster 1704-1 whether the data resource is a local data resource or a remote data resource relative to that cluster. The WWH catalog instance 1750-1 provides responses to those requests back to the requesting WAM components.

In the FIG. 17 embodiment, it is assumed that the distributed WWH catalog is implemented as a plurality of WWH catalog instances distributed over the clusters with each of the clusters having visibility of only its corresponding one of the instances of the distributed WWH catalog. The WWH catalog in such an arrangement and other similar arrangements herein is more generally referred to as a "distributed catalog service" of the corresponding multi-cluster distributed data processing platform.

It is further assumed that the instances of the distributed WWH catalog are implemented as respective YARN applications running on respective ones of the clusters. A given one of the instances of the distributed WWH catalog may be configured in accordance with a configuration file that is stored in a predetermined storage location of the corresponding cluster, such as, for example, a predefined location in an underlying HDFS of that cluster. The configuration file contains information about the local and remote data resources having respective meta-resources that are known to the corresponding instance of the WWH catalog. The YARN application implementing a given instance of the distributed WWH catalog is illustratively executed as part of a setup process for the corresponding cluster.

In order to deploy the WWH catalog instance on a given cluster, a special job may be submitted to that cluster. For example, a WWHCatalogSubmit job may be used in order to submit a WWH catalog instance into a cluster. The submitted job may contain a pre-resolved meta-resource pointing to one or more configuration files of respective catalogs that are to be created using this job.

In other embodiments, the configuration file may be replaced with another type of configuration object. The term "configuration object" as used herein is intended to be broadly construed so as to encompass a configuration file or other type of stored configuration information relating to a distributed catalog instance.

The distributed WWH catalog is assumed in the present embodiment to be a private component of the WWH platform, and is therefore not subject to modification by framework developers. Instead, only platform developers are permitted to modify the distributed WWH catalog in this embodiment.

As mentioned previously, a given WWH catalog instance such as WWH catalog instance 1750-1 on cluster 1704-1 illustratively comprises a plurality of entries with each such entry comprising a meta-resource comprising information characterizing location and accessibility of a corresponding one of the data resources. The resolving API 1754-1 illustratively returns a given meta-resource responsive to a request that includes a corresponding meta-resource identifier.

If a meta-resource identifier presented to WWH catalog instance 1750-1 on cluster 1704-1 resolves to a local data resource of that cluster, the resolving API 1754-1 returns the corresponding meta-resource allowing the requesting application to access the corresponding local data resource in cluster 1704-1.

If a meta-resource identifier presented to WWH catalog instance 1750-1 on cluster 1704-1 resolves to a remote data resource not locally accessible within that cluster, the resolving API 1754-1 can operate in one of a number of different evaluation modes. For example, in a "lazy" mode of evaluation, the resolving API 1754-1 returns information that allows the application to access the remote instance of the catalog in order to obtain the remote meta-resource. The returned information may be in the form of a URL for the particular remote instance of the distributed WWH catalog that is implemented in the remote cluster having local access to the resource in question. Alternatively, the resolving API 1754-1 can operate in an "eager" mode of evaluation in which it requests the remote meta-resource from the WWH catalog instance in the remote cluster and then provides the received remote meta-resource to the requesting application. This illustratively involves the resolving API 1754-1 making one or more RPCs to other WWH catalog instances in other clusters.

If a particular meta-resource identifier is not found in the WWH catalog instance 1750-1, the resolving API 1754-1 can return an error indicating that the corresponding meta-resource was not found. Alternatively, it can call a Find API that searches for the meta-resource. The Find API may go through a list of clusters that it knows and then, for each, it calls the non-lazy mode of evaluation of the resolving API. It is assumed that the Find API has access to one or more lists of clusters.

The above-noted lazy evaluation mode is the default mode for the resolving API in some embodiments. For example, this evaluation mode is particularly well-suited for embodiments in which meta-resource identifiers for remote resources are passed from a local WWH-ClusterNodeManager to a remote WWH-ClusterNodeManager in that cluster, for resolving in the remote cluster. Such an arrangement is particularly efficient in that it allows the final resolution of each data resource to be made in its local cluster.

A given one of the instances of the distributed WWH catalog such as WWH catalog instance 1750-1 of cluster 1704-1 in conjunction with its initiation as a YARN application may be registered as a service with a service registry of a resource manager of the cluster 1704-1. In such an arrangement, the service registry of the resource manager of the cluster 1704-1 is utilized to identify the browsing and resolving APIs 1752-1 and 1754-1 to requesting clients or WAM components.

FIG. 18 illustrates a method of utilizing a WWH catalog in an illustrative embodiment. In this embodiment, a portion 1800 of a multi-cluster distributed data processing platform comprises a first YARN cluster 1804-1. The cluster 1804-1 comprises a corresponding instance 1850-1 of a distributed WWH catalog. The WWH catalog instance 1850-1 of the cluster 1804-1 comprises a browsing API 1852-1 accessible to a client 1812-1. The WWH catalog instance 1850-1 further comprises a resolving API 1854-1 accessible to a WAM component of a corresponding application running in the cluster 1804-1. The features, arrangement and operation of the WWH catalog instance 1850-1 are generally similar to those of WWH catalog instance 1750-1 as previously described in conjunction with FIG. 17.

The method as illustrated in FIG. 18 includes a sequence of processing steps indicated by circled numbers.

In step 1, the client 1812-1 browses the WWH catalog instance 1850-1 of cluster 1804-1 via the browsing API 1852-1. As noted above, the WWH catalog instance may register itself as a service with the YARN resource manager under an address such as services/wwh/catalog. The client 1812-1 can therefore locate the browsing API 1852-1 of the WWH catalog instance 1850-1 of the cluster 1804-1 by querying the resource manager registry service of that cluster. The WWH catalog instance 1850-1 illustratively includes lists of meta-resources with each such meta-resource having a corresponding meta-resource identifier and containing information regarding location and accessibility of a corresponding data resource. Such lists are assumed to be provided in human-readable form to clients via the browsing API 1852-1.

In step 2, the client 1812-1 creates a processing job, illustratively an application utilizing a WWH processing framework, for submission to the cluster 1804-1. The processing job is configured to utilize data resources having respective meta-resource identifiers from the WWH catalog instance 1850-1.

In step 3, the client 1812-1 submits the job to the cluster 1804-1. The submitted job includes a list of meta-resource identifiers for respective data resources to be utilized in conjunction with execution of that job. The meta-resource identifiers are determined from the WWH catalog instance based at least in part on the browsing in step 1.

In step 4, the WAM component created by YARN for the submitted job accesses the resolving API 1854-1 in order to resolve the local or remote status of the various data resources required for execution of the job. For example, the WAM component will attempt to resolve the local or remote status for all the meta-resource identifiers submitted with the job to be executed. If a given meta-resource identifier is resolved to a remote data resource, a recursive job on the corresponding remote cluster will be initiated via a new remote cluster node manager of the WAM component.

The process will then continue in a manner similar to that previously described herein until the job is completed utilizing the cluster 1804-1 to process data resources local to that cluster and one or more additional clusters to process remote data resources. The corresponding processing results are aggregated by one or more WWH aggregators and returned to the client 1812-1.

FIGS. 19 through 24 illustrate example WWH catalog related features and functionality of illustrative embodiments. The circled numbers shown in FIGS. 21, 22, 23 and 24 are indicative of example processing sequence flows utilized in these illustrative embodiments.

Figure 19:
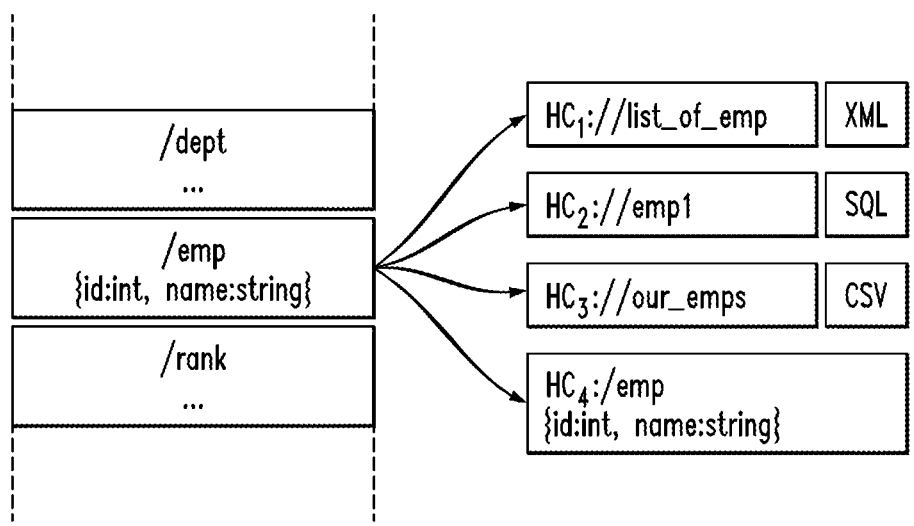
FIGS. 19 through 24 illustrate example WWH catalog related features and functionality of illustrative embodiments.

With reference to FIG. 19, an illustration of the recursive nature of a meta-resource of a WWH catalog is shown. In this embodiment, a meta-resource denoted/emp can provide access to multiple versions of the underlying data resource using various additional or alternative data formats, including XML, SQL and CSV formats.

Figure 20:
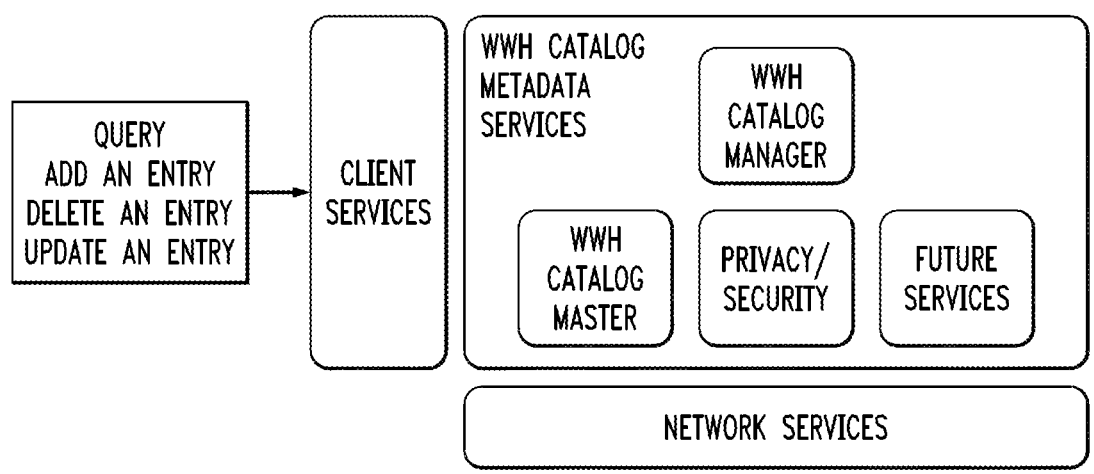

FIG. 20 illustrates an example of supported services of the WWH catalog in one embodiment. In this embodiment, a client services interface of WWH catalog metadata services supports a variety of requests such as query, add an entry, delete an entry and update an entry. The WWH catalog metadata services includes components such as a WWH Catalog Manager and a WWH Catalog Master, as well as a network services interface. The WWH catalog metadata services further support privacy and/or security services, and includes a capability to add future services.

Figure 21:
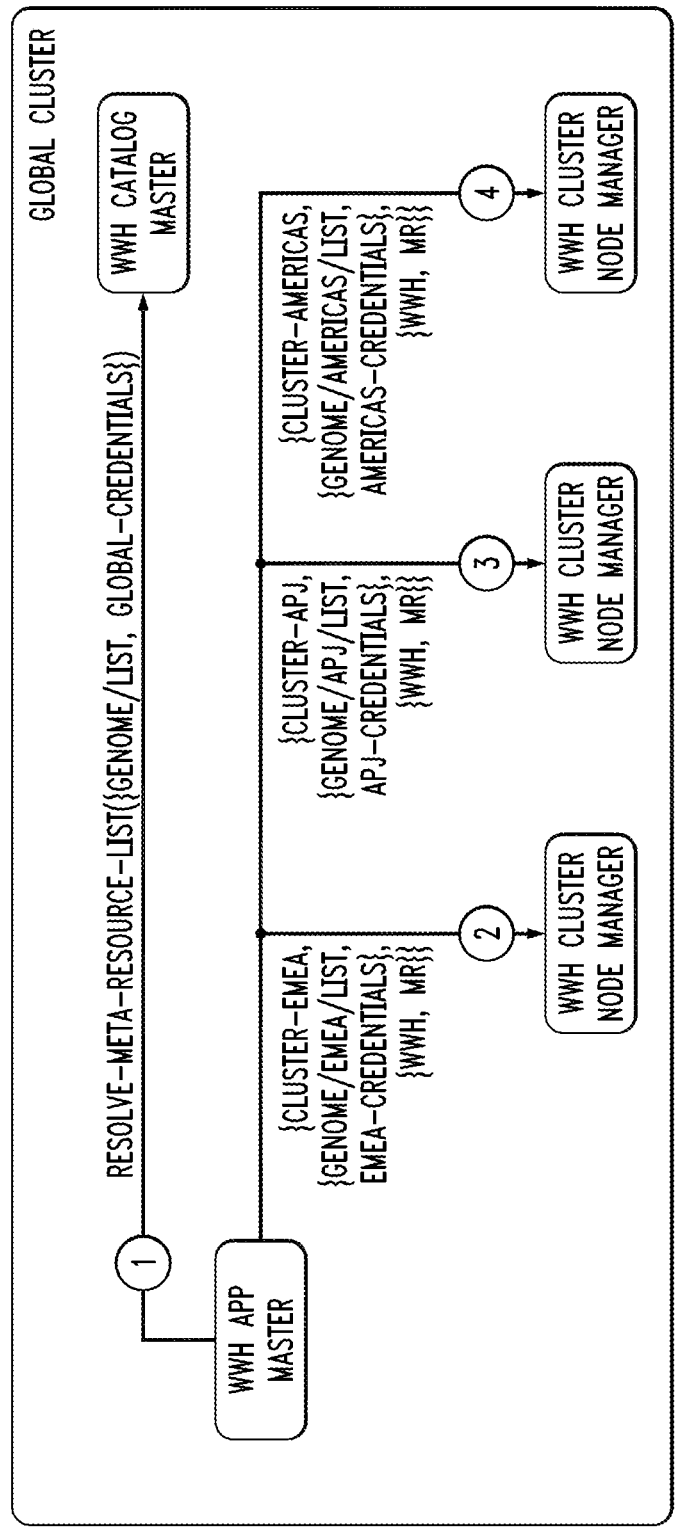
Figure 22:
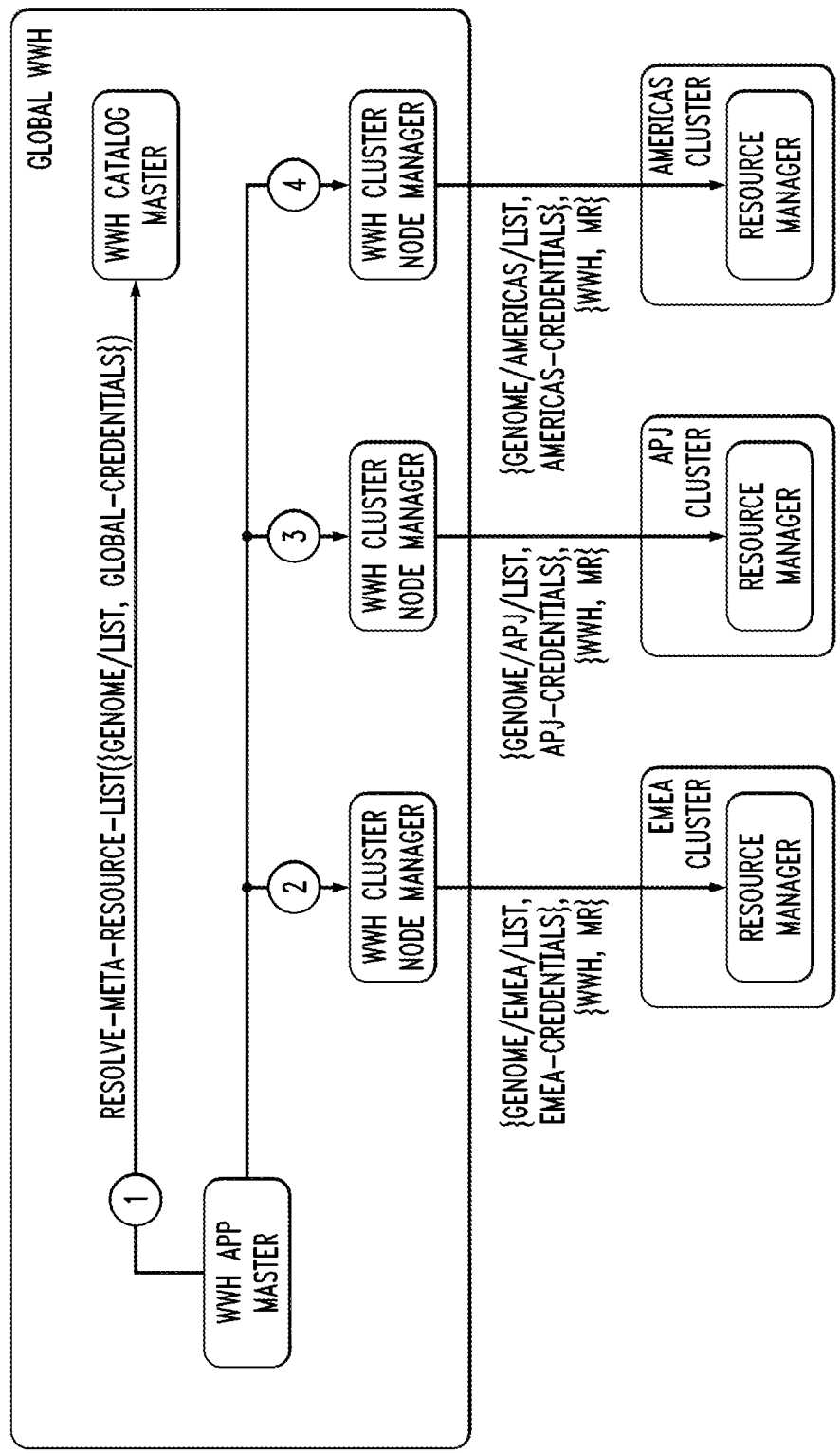
Figure 23:
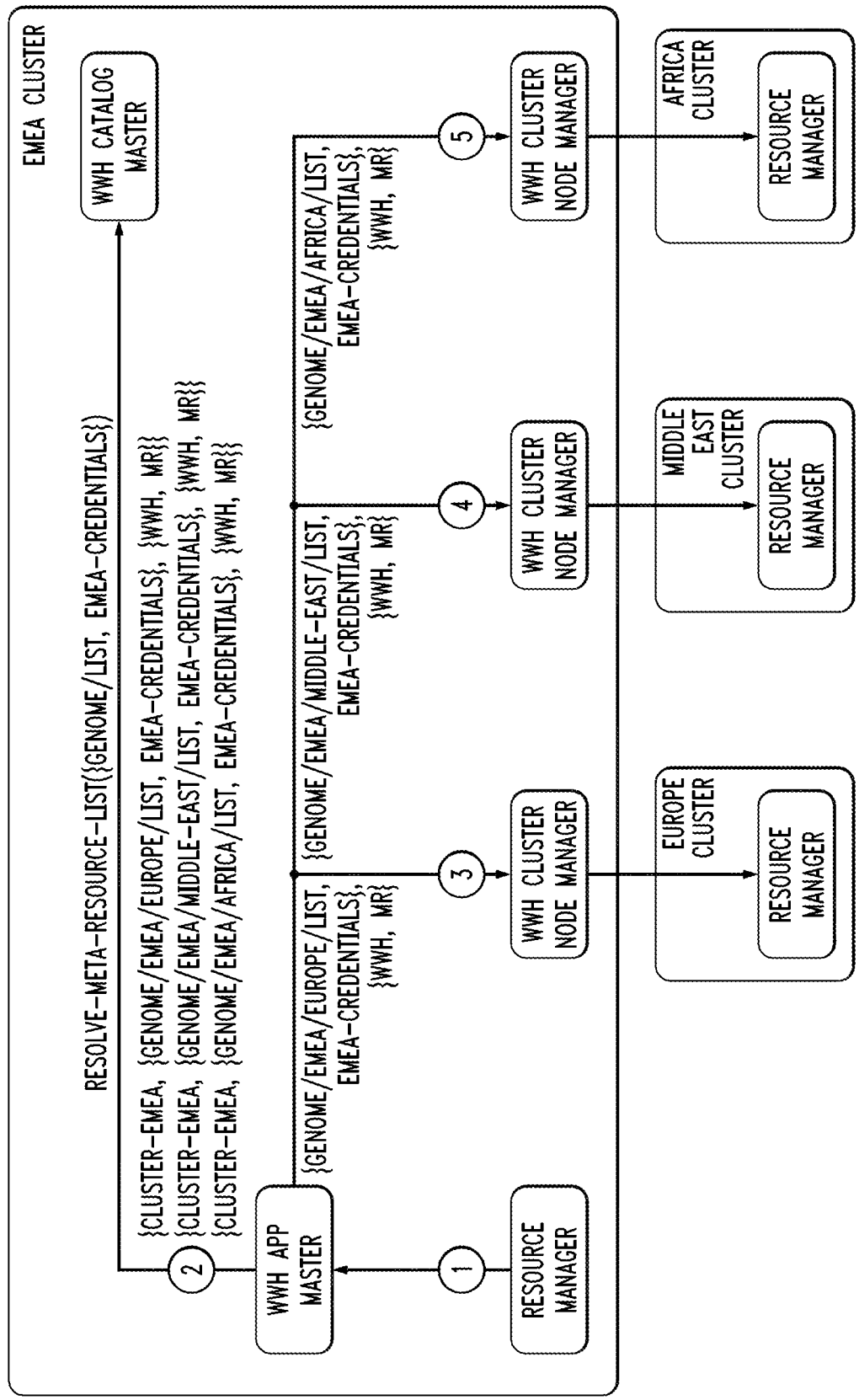

Referring now to FIGS. 21-23, example techniques for resolving a meta-resource list are shown. It is assumed for this embodiment that a multi-cluster distributed data processing platform comprises seven distinct YARN clusters in respective different geographic regions, namely, a Global cluster ("Cluster-Global"), an EMEA cluster ("Cluster-EMEA"), an APJ cluster ("Cluster-APJ"), an Americas cluster ("Cluster-Americas"), a Europe cluster ("Cluster-Europe"), a Middle East cluster ("Cluster-Middle-East"), and an Africa cluster ("Cluster-Africa"), where Global denotes a geographic region encompassing all the other regions, EMEA denotes a geographic region encompassing Europe, Middle East and Africa, APJ denotes a geographic region encompassing Asia Pacific and Japan, Americas denotes a geographic region encompassing North and South America, Europe denotes a geographic region encompassing all of the countries in Europe, Middle East denotes a geographical region encompassing all of the countries in the Middle East, and Africa denotes a geographical region encompassing all of the countries in Africa.

A WWH application master of the Global cluster submits a metadata resource list to the WWH Catalog Master, which identifies resources in the EMEA cluster, the APJ cluster and the Americas cluster. FIGS. 21, 22 and 23 illustrate interactions between WWH cluster node managers ("WWH Cluster Node Managers"), and resource managers ("Resource Managers") under the control of a WWH application master in resolving a meta-resource list denoted Genome/List. In this illustrative example, the technique for resolving a meta-resource list is implemented using the WWH framework.

Referring to FIG. 21 in particular, the WWH Application Master sends a resolve request (1) to the WWH Catalog Master passing the name of a meta-resource, the Genome/List illustrating, in this embodiment, a list of all genome files located worldwide, and passing a set of credentials to be used for Global Access. The WWH Application Master then receives from the WWH Catalog Master a list of resources that can be accessed by Cluster-EMEA, by Cluster-APJ, and by Cluster-Americas. The WWH Application Master then passes this information to each one of the WWH Cluster Node Managers that will be responsible for the communication with the respective clusters. More specifically, in this embodiment, it will pass the list of meta-resources Genome/EMEA/List and the associated credentials to access data in Cluster-EMEA to the WWH Cluster Node Manager that will communicate with Cluster-EMEA (2). It will then pass the list of meta-resources Genome/APJ/List and the associated credentials to access data in Cluster-APJ to the WWH Cluster Node Manager that will communicate with Cluster-APJ (3). In addition, it will pass the list of meta-resources Genome/Americas/List and the associated credentials to access data in Cluster-Americas to the WWH Cluster Node Manager that will communicate with Cluster-Americas (4).

With respect to FIG. 22, the embodiment illustrates the passing of parameters between the WWH Cluster Node Managers and the Resource Managers of the respective clusters with which they communicate. As previously described in conjunction with FIG. 21, the WWH Application Master sends a Resolve request to the WWH Catalog Master (1). The WWH Catalog Master then returns respective lists of resources residing in EMEA-Cluster, APJ-Cluster and Americas-Cluster. The WWH Application Master then passes the separate lists and the associated credentials to the respective WWH Cluster Node Managers (2, 3 and 4), which communicate with the Resource Managers of the respective clusters.

With respect to FIG. 23, this embodiment illustrates the recursive nature of the approach, where a sequence of activities similar to that previously described also occurs in Cluster-EMEA, once the application is submitted there. The Resource Manager in Cluster-EMEA creates a WWH Application Master (1). The WWH Application Master then sends a Resolve request to the WWH Catalog Master (2). The WWH Catalog Master then returns a list of resources residing in Cluster-Europe, Cluster-Middle-East and Cluster-Africa. The WWH Application Master then passes the separate lists and the associated credentials to the respective WWH Cluster Node Managers (3, 4 and 5).

Figure 24:
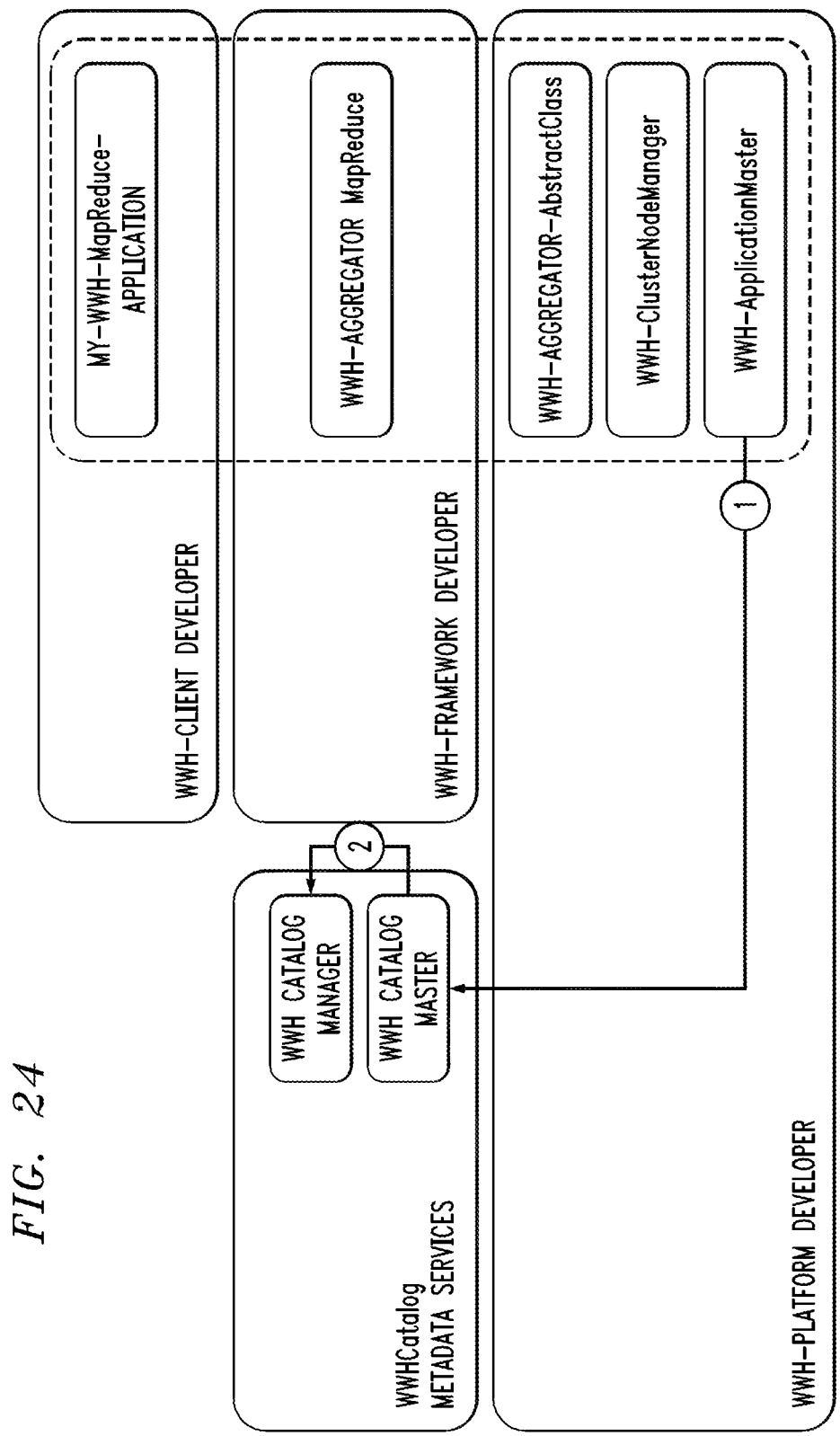

FIG. 24 illustrates the manner in which the WWH-ApplicationMaster initiates the WWH catalog in this embodiment. The arrangement is otherwise similar to that previously described in conjunction with FIG. 12.

Again, the particular WWH components and their illustrative arrangements and interactions as shown in FIGS. 19 through 24 is by way of example only, and should not be construed as limiting in any way. Numerous alternative arrangements of components configured to interact in different manners can be used in alternative implementations of WWH platforms of the type disclosed herein.

An example global MapReduce WWH framework and associated application flow utilizing the above-described WWH platform and associated WWH catalog will now be described in more detail. In this example, the WWH framework more particularly comprises the above-noted WWH-MapReduce-GlobalReduce framework. It is assumed that a client submits a WWH-MapReduce-GlobalReduce application for execution in accordance with the corresponding framework. Each of the YARN clusters in the multi-cluster distributed data processing platform in this embodiment runs a local MapReduce application. The output of all clusters is transmitted to a selected cluster and then that selected cluster runs a global MapReduce application.

It is assumed that the local cluster that receives the WWH-MapReduce-GlobalReduce application from the submitting client is denoted as cluster C0, and that there are two additional participating clusters denoted as clusters C1 and C2, respectively. It is further assumed that these clusters are in respective separate data zones and that each of the clusters has access to the local data resources of its corresponding data zone.

The clusters C0, C1 and C2 in this example are implemented as respective Docker-based clusters, each running YARN and HDFS. Each cluster runs an instance of a distributed WWH catalog as a YARN application. The different WWH catalog instances are differentiated by their respective configuration files. More particularly, each WWH catalog instance has a unique configuration file that describes the local and remote meta-resources relative to the corresponding cluster. The local meta-resources are assumed to be described by information identifying their location in the local file system (e.g., file name or file path), and the remote meta-resources are assumed to be described by information identifying their respective remote clusters. Other types of information indicative of location and accessibility of local or remote data resources can be used in other embodiments.

The client submits the WWH-MapReduce-GlobalReduce application as a YARN application to the ResourceManager that resides on C0. A corresponding WWH-ApplicationMaster is started in conjunction with the submission of the WWH-MapReduce-GlobalReduce application. The WWH-MapReduce-GlobalReduce application includes a list of meta-resource entries from the WWH catalog, an aggregator class, and mapper, reducer and global-reducer classes.

It should be noted in this regard that the aggregator class is supplied by the framework developer as part of the WWH-MapReduce-GlobalReduce framework. The client supplies the application-specific classes of mapper, reducer and global-reducer, as well as the list of meta-resource identifiers from the WWH catalog which collectively represent input data for the application.

The above-noted WWH-ApplicationMaster is created by the YARN resource manager of the cluster C0 upon submission of the WWH-MapReduce-GlobalReduce application. The WWH-ApplicationMaster utilizes the resolving API of the WWH catalog instance of cluster C0 to resolve the local or remote status of each of the meta-resource identifiers submitted with the application.

If a given meta-resource identifier is determined to represent a remote data resource not accessible in cluster C0 but accessible in one of the other clusters C1 or C2, the WWH-ApplicationMaster will initiate a recursive job at the appropriate remote cluster via a corresponding one of a plurality of WWH-ClusterNodeManagers configured to communicate with respective ones of the remote clusters C1 and C2.

For those meta-resource identifiers that resolve to local data resources of cluster C0, a local MapReduce job will be executed on cluster C0 using those resources via a local WWH-ClusterNodeManager.

When the WWH-ClusterNodeManager in C0 starts it examines the received job and requests from the ResourceManager in C0 a new container that will run the supplied aggregator class. After the ResourceManager has allocated the container, the WWH-ClusterNodeManager sends the job information bundled with the WWH-ApplicationMaster information to the WWH-Aggregator as its initializing arguments. The WWH-Aggregator then starts and submits both local and remote jobs. When the WWH-Aggregator starts, for every cluster in the provided resources list, it collects the names of all the files for that particular cluster. It requests a new job execution on the appropriate cluster, with the same aggregator, mapper and reducer classes.

The WWH-ApplicationMaster receives the jobs submitted by the WWH-Aggregator. Any such job that is local is passed to the local WWH-ClusterNodeManager that was already created. For a remote job, a remote WWH-ClusterNodeManager is created. Assume that the WWH-ApplicationMaster examines a given job and sees that it is a remote job to be assigned to C1. If it sees that there is no running WWH-ClusterNodeManager for C1, the WWH-ApplicationMaster starts one, denoted WWH-ClusterNodeManager-C0-C1, and passes the job to it.

When WWH-ClusterNodeManager-C0-C1 starts it examines the job it received and determines that it is a remote job. It then acts just like an initializing client. More particularly, WWH-ClusterNodeManager-C0-C1 submits the WWH-ApplicationMaster to the ResourceManager of C1. Once the WWH-ApplicationMaster is up, WWH-ClusterNodeManager-C0-C1 submits a job with the same parameters, except for the resources, which are the resources only relevant to C1. When the WWH-ApplicationMaster on C1 receives this job submission request it will recursively perform steps similar to those described above for the WWH-ApplicationMaster on C0.

When a WWH-Aggregator starts on a given cluster Ci, it receives the job information which contains the list of files, a mapper class and a reducer class. It then executes the job on its local cluster Ci using regular YARN services. When the job completes it reports its results and terminates.

Local and remote results generated by respective local and remote clusters are updated as follows. When the WWH-ApplicationMaster on a given cluster Ci receives a job results link it looks up the WWH-ClusterNodeManager that is responsible for sending this job (e.g., WWH-ClusterNodeManager-Cj-Ci), and passes the results to it. The WWH-ClusterNodeManager-Cj-Ci then updates the job status.

The local and remote results are aggregated in the following manner. A WWH-Aggregator-For-MapReduce-Global in conjunction with monitoring the status of the various jobs will receive links to the results generated by all the WWH-Aggregator-For-MapReduce-Local processes. Each time such a link is received, the WWH-Aggregator-For-MapReduce-Global will download the results data to its local cluster. The data is transferred via HTTP or other suitable protocols, and access control mechanisms may be utilized in conjunction with such transfer. When all the jobs are completed and their results are fully downloaded, the WWH-Aggregator on C0 will execute the aggregation code, in this case the global reduce on C0. Upon completion of the aggregation, the WWH-Aggregator will post the link for the results, just like any other WWH-Aggregator, and then terminate itself. The submitting client will then be able to obtain the aggregated processing results.

As a more particular example of a WWH application that can utilize the above-described WWH-MapReduce-GlobalReduce framework, consider an information processing system comprising multiple data centers located at different sites around the world, with the data centers maintaining respective large local document repositories. Data analysts wish to perform analytics in the form of a simple word count on the documents on all the sites. However, in performing this analysis, data centers cannot transmit complete documents to one another, but only the results of their respective local word counts. This restriction can be the result of a privacy issue (e.g., the data centers do not wish to expose their documents to the public), network bandwidth (e.g., the data is simply too large), or both.

A WWH application for performing a global word count in the above-described system can be configured as follows. First, a local word-count will be performed on each of the YARN clusters utilizing the local MapReduce framework. Then, the results of the local MapReduce processing are transmitted to a single one of the clusters, and a global reducing task is performed on the processing results in that single cluster. This last operation is illustratively performed by the previously-described global reducer which is part of the WWH-MapReduce-GlobalReduce framework. In other embodiments, alternative aggregation techniques can be used in place of the global reducer at a single cluster. For example, processing results can be aggregated incrementally using multiple ones of the clusters.

A wide variety of other types of analytics processing can be implemented using WWH platforms as disclosed herein.

As another example, bioinformatics applications for metagenomics-based biological surveillance can utilize the WWH-MapReduce-GlobalReduce framework. In one such arrangement, an initial cluster accepts sample genomes which are sent to a plurality of other clusters. Each of the clusters uses a local MapReduce process to compare the samples with private genomic information locally accessible in the corresponding cluster. The results of this local comparison in each cluster are in the form of one or more vectors which are sent back to the initial cluster. The initial cluster then runs a global reducer on the received vectors creating aggregated processing results in the form of a results matrix. This results matrix may be sent to the client for further analysis in order to detect the particular sample causing the problem.

In some embodiments configured to implement bioinformatics applications of the type described above, reads of local biological samples obtained from metagenomics sequencing are subject to mapping operations in each of the clusters. For example, one or more reads of a given biological sample may be subject to mapping based on string resemblance to target genomic sequences. Such a mapping arrangement is illustratively used to generate a hit abundance score vector for the given biological sample. Multiple such hit abundance score vectors generated for different biological samples are combined into a hit abundance score matrix that is utilized in characterizing a disease, infection or contamination, or otherwise providing analytics functionality within the system.

Yet another example is a cooperative security anomaly detection application which uses accumulating evidence to improve the quality of local detectors. Each local detector is run on a single YARN cluster of a multi-cluster WWH platform, and uses its own detecting algorithm implemented as a local MapReduce application using its own private data. The aggregated results of the detection are sent back to the initial cluster using aggregated non-private features only. The initial cluster executes a global reducer to select a set of the best global features and these are sent back to the local detectors of the respective clusters. This process continues for several iterations, with each iteration comprising a new global map-reduce application instance, until it converges. The process considerably improves local detector accuracy using the detection results received from the other clusters.

An arrangement of this type can be implemented in a system for malware detection that operates by analyzing Big Data comprising Domain Name Service (DNS) transactions associated with the web site of a large company. Clearly, such a company will be reluctant to share its transactions logs with other businesses. However, the company may well be willing to share anonymized statistical data in order to defeat a malware threat. By sharing statistical data of multiple sites in the manner described above, an improved malware detector can be constructed. Such a shared detector can use a multi-cluster distributed data processing platform of the type disclosed herein in order to enable the run of the improved detector on data in multiple sites, each using the detector on its own transaction logs and improving the probability of malware detection. No sharing of data and no common file system is needed or used. Other embodiments can incorporate additional functionality for access control, progress monitoring and support of a pluggable failure handling policy.

These example applications demonstrate the use of the WWH-MapReduce-GlobalReduce framework, and serve to illustrate the flexibility provided by the distributed WWH catalog in terms of locating relevant input data. They also demonstrate the privacy and performance features of WWH platforms.

Again, the use of MapReduce as part of a WWH framework is by way of illustrative example only. Numerous alternative frameworks can be utilized as part of a given WWH framework, including in some embodiments any framework supported by YARN, as well as other frameworks in non-YARN embodiments.

The multi-cluster distributed data processing platforms of illustrative embodiments disclosed herein provide significant advantages relative to conventional arrangements.

As mentioned previously, illustrative embodiments move the computation instead of moving the data and create an abstraction to distributed Big Data in order to overcome the drawbacks of conventional systems, providing significant advantages in terms of both performance and privacy, and related advantages such as the facilitation of GRC, as outlined in detail elsewhere herein.

Additional illustrative embodiments comprising beacon-based arrangements will now be described with references to FIGS. 25 through 28. In these embodiments, it is assumed that a beacon-based distributed data processing platform comprises a plurality of beacon lit sites. Such sites may comprise, for example, respective geographically-distributed data centers or other repositories of locally-accessible data to be processed by WWH nodes or other processing nodes of the platform.

It is further assumed that the beacons generally correspond to respective beacons configured in accordance with the Beacon Project of the Global Alliance for Genome and Health (GA4GH), but suitably modified to support WWH functionality as disclosed herein. The beacons may therefore be implemented at least in part in a manner analogous to GA4GH beacons, although a wide variety of other types of beacons can be used in other embodiments. The term "beacon" as used herein is intended to be broadly construed so as to encompass various mechanisms in which a given site can make its presence and availability known to processing nodes of a distributed data processing platform. It is possible that a given site may itself comprise a YARN cluster or at least one WWH node in some embodiments.

Figure 25:
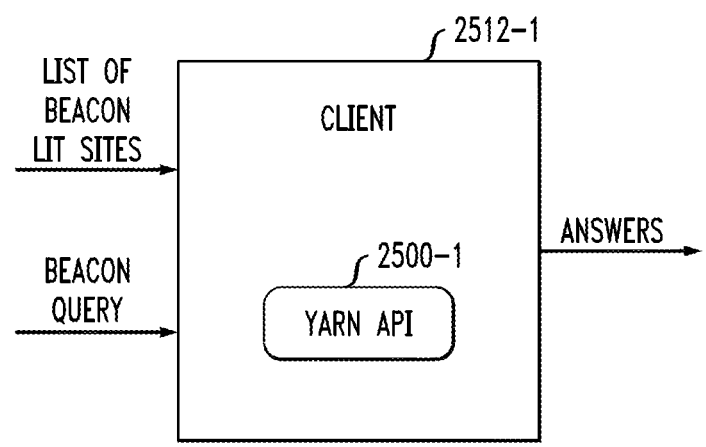
FIGS. 25 through 28 show illustrative embodiments of beacon-based distributed data processing platforms utilizing WWH functionality.

Referring now to FIG. 25, a client 2512-1 of a WWH platform comprises a YARN API 2500-1. The YARN API 2500-1 is advantageously configured to leverage the WWH functionality of the WWH platform. In this embodiment, it is assumed that the client 2512-1 receives as one of its inputs a list of beacon "lit" sites, where such a site is assumed to have its beacon activated or "lit." The client also receives a beacon query, which illustratively comprises a request for information or analysis involving one or more of the beacon lit sites on the list of beacon lit sites, and generates one or more answers in response to the beacon query, utilizing the WWH platform to access one or more of the beacon lit sites and their respective sets of locally-available data resources.

The beacon lit sites are examples of what are more generally referred to herein as "beacon entities." Such entities generally comprise respective activatable beacons, and may represent respective participants in a beacon network.

Figure 26:
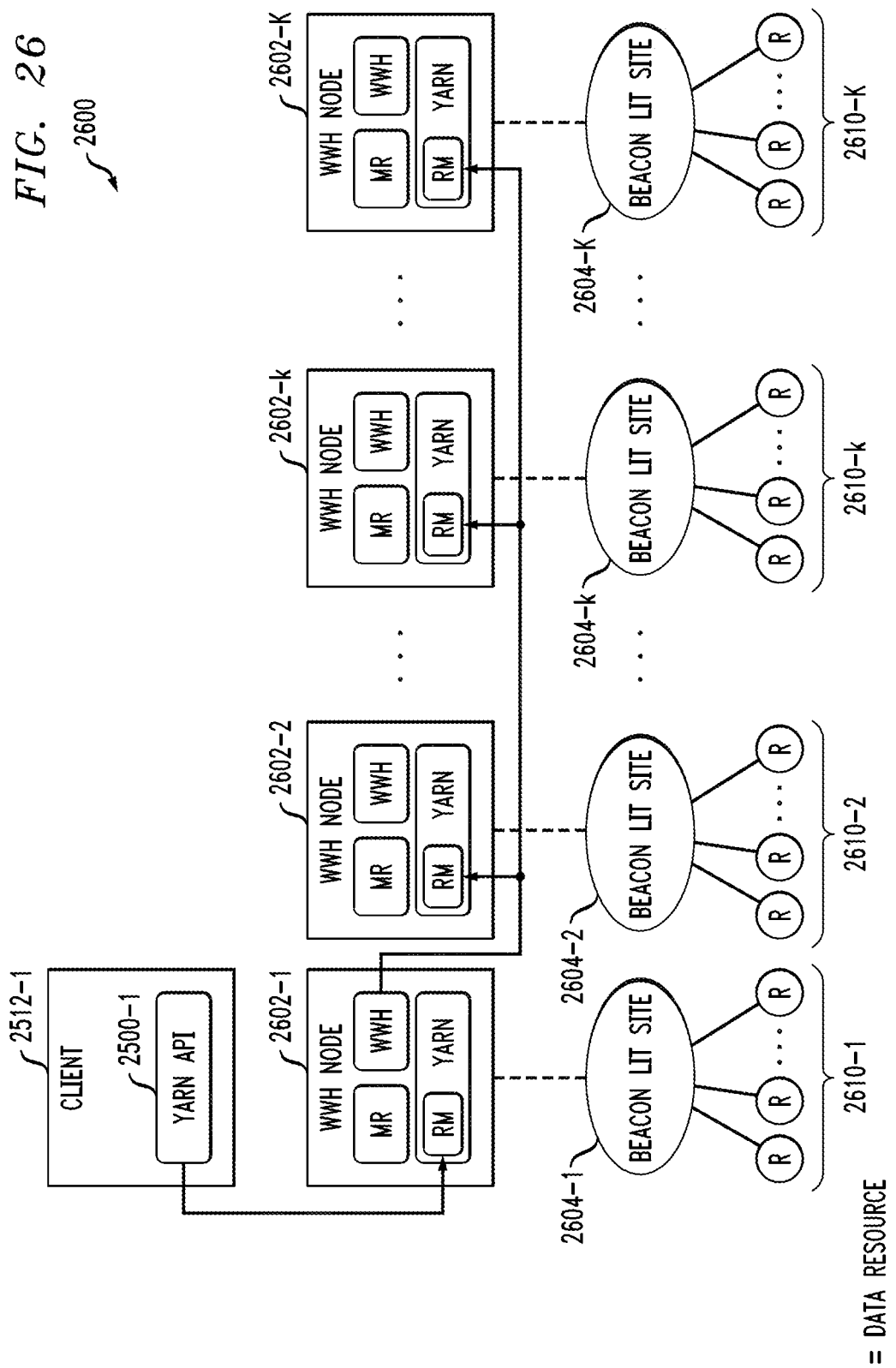

FIG. 26 shows a WWH platform 2600 in an illustrative embodiment that includes the client 2512-1 and its YARN API 2500-1. The WWH platform 2600 in this embodiment further comprises WWH nodes 2602-1, 2602-2, . . . 2602-$k$, . . . 2602-K, each comprising a YARN component, a WWH component and a MapReduce ("MR") component. The YARN components of the respective WWH nodes 2602 include respective resource managers each denoted RM. The WWH platform 2600 further comprises beacon lit sites 2604-1, 2604-2, . . . 2604-$k$, . . . 2604-K having local access to respective sets 2610-1, 2610-2, . . . 2610-$k$, . . . 2610-K of data resources, with each data resource being denoted R. Each of the WWH nodes 2602 has the capability of establishing a possible connection to at least one of the beacon lit sites 2604, with the connection being illustrated by a dashed line in the figure.

As mentioned previously, values of variables such as K used herein are arbitrary, and can vary from embodiment to embodiment. For example, other embodiments of the WWH platform can include different numbers of WWH nodes, beacon lit sites and associated sets of data resources.

In the FIG. 26 embodiment, the client 2512-1 via its YARN API 2500-1 becomes a client of the YARN component of the first WWH node 2602-1. More particularly, the YARN API 2500-1 accesses the YARN component of the first WWH node 2602-1 via the RM of the YARN component of that WWH node. The WWH component of the first WWH node 2602-1 leverages at least a subset of the other WWH nodes 2602 via their respective RMs within their respective YARN components. This allows computations or other operations associated with the beacon query to be performed in a distributed manner under the control of the WWH nodes 2602 that are closest to or have another type of association or relationship with the relevant beacon lit sites. Accordingly, in this embodiment and other similar embodiments, one or more additional WWH nodes are selected by a given one of the WWH nodes for handling at least portions of the beacon query based at least in part on proximity of the one or more additional WWH nodes to a corresponding one of the beacon entities. Again, associations or relationships other than or in addition to proximity can be used in selecting a particular WWH node for participation in processing of the beacon query.

Such an arrangement provides significant advantages relative to alternative beacon arrangements in which the client would otherwise have to interact directly with each of the beacon lit sites in order to resolve a given beacon query. In the present embodiment, the client does not need to know which beacon-based resources can be accessed and where such resources are located within the system.

Moreover, the WWH platform 2600 can not only execute beacon queries but can more generally perform any other types of computations or analytics processing operations in accordance with other frameworks supported by YARN, such as MapReduce, Spark and many others. These operations are advantageously performed in decentralized and privacy-preserving manner within the WWH platform.

Although only a single layer of WWH nodes 2602 is shown in this embodiment, other embodiments can include multiple distinct layers of WWH nodes.

It should also be noted that this embodiment and other beacon-based distributed data processing platform embodiments illustratively operate using a recursive approach similar to that described in the context of other WWH platform embodiments herein. For example, one WWH node can directly access those beacon lit sites that it has local access to while also initiating one or more applications on one or more other WWH nodes to obtain remote access to one or more other beacon lit sites. Also, advantages similar to those of the other WWH platform embodiments in terms of system performance and compliance with privacy, security and GRC requirements are obtained.

Figure 27:
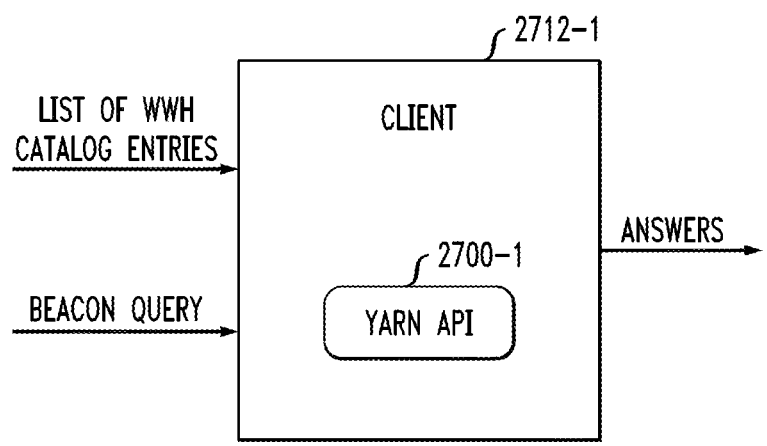
Figure 28:
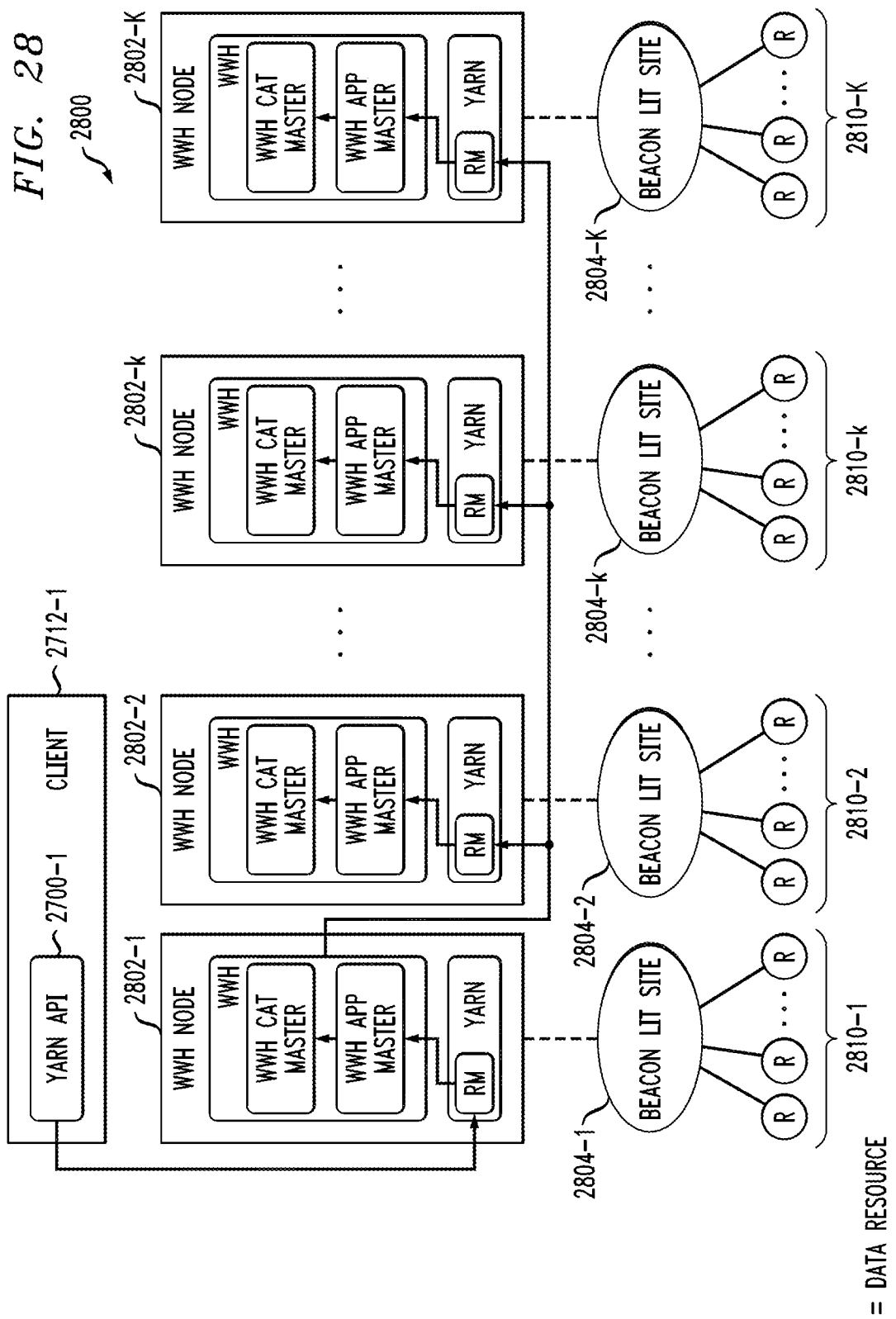

Another beacon-based distributed data processing platform embodiment is illustrated in FIGS. 27 and 28. This embodiment is similar to the embodiment previously described in conjunction with FIGS. 25 and 26, but additionally makes use of WWH catalog functionality as part of the WWH platform.

Referring now to FIG. 27, a client 2712-1 of a WWH platform comprises a YARN API 2700-1. The YARN API 2700-1 is advantageously configured to leverage the WWH functionality of the WWH platform. In this embodiment, it is assumed that the client 2712-1 receives as one of its inputs a list of WWH catalog entries. The client also receives a beacon query, which illustratively comprises a request for information or analysis involving one or more of the WWH catalog entries on the list of WWH catalog entries, and generates one or more answers in response to the beacon query, utilizing the WWH platform to access one or more of beacon lit sites and their respective sets of locally-available data resources. Accordingly, in this embodiment, the list of beacon lit sites is replaced with the list of WWH catalog entries. Such an arrangement advantageously avoids the need for client applications to have knowledge of lists of beacon lit sites for use in processing a beacon query.

FIG. 28 shows a WWH platform 2800 in an illustrative embodiment that includes the client 2712-1 and its YARN API 2700-1. The WWH platform 2800 in this embodiment further comprises WWH nodes 2802-1, 2802-2, . . . 2802-$k$, . . . 2802-K, each comprising a YARN component and a WWH component. The YARN components of the respective WWH nodes 2802 include respective resource managers each denoted RM. The WWH platform 2800 further comprises beacon lit sites 2804-1, 2804-2, . . . 2804-$k$, . . . 2804-K having local access to respective sets 2810-1, 2810-2, . . . 2810-$k$, . . . 2810-K of data resources, with each data resource being denoted R. Each of the WWH nodes 2802 has the capability of establishing a possible connection to at least one of the beacon lit sites 2804, with the connection being illustrated by a dashed line in the figure. Again, the particular numbers of WWH nodes, beacon lit sites and associated sets of data resources are arbitrary.

In the FIG. 28 embodiment, the client 2712-1 via its YARN API 2700-1 becomes a client of the YARN component of the first WWH node 2802-1. More particularly, the YARN API 2700-1 accesses the YARN component of the first WWH node 2802-1 via the RM of the YARN component of that WWH node. The WWH component of the first WWH node 2802-1 leverages at least a subset of the other WWH nodes 2802 via their respective RMs within their respective YARN components. This allows computations or other operations associated with the beacon query to be performed in a distributed manner under the control of the WWH nodes 2802 that are closest to or have another type of association or relationship with the relevant beacon lit sites to be contacted in conjunction with processing of the beacon query.

Within each of the WWH nodes 2802 in this embodiment, the YARN RM initiates a WWH Application Master as illustrated. The WWH Application Masters interact with respective WWH Catalog Masters, which represent respective instances of a distributed WWH catalog service in this embodiment.

By way of example, the use of the distributed WWH catalog service in this embodiment allows the client to identify a particular subset of beacon lit sites that should participate in execution of a given beacon query. This is illustratively only a relatively small but focused subset of the full set of beacon lit sites. Accordingly, the distributed WWH catalog functionality of the FIG. 28 embodiment will tend to reduce the amount of network traffic and processing overhead associated with execution of a given beacon query.

Like the embodiment described in conjunction with FIGS. 25 and 26, the embodiment described in conjunction with FIGS. 27 and 28 also provides significant additional advantages relative to alternative beacon arrangements in which the client would otherwise have to interact directly with each of the beacon lit sites in order to resolve a given beacon query. Moreover, the WWH platform 2800 can not only execute beacon queries but can more generally perform any other types of computations or analytics processing operations in accordance with other frameworks supported by YARN, such as MapReduce, Spark and many others. These operations are advantageously performed in decentralized and privacy-preserving manner within the WWH platform 2800. In addition, although the WWH platform 2800 is shown as comprising a single layer of WWH nodes 2802 in this embodiment, other embodiments can include multiple distinct layers of WWH nodes.

The beacon-based distributed data processing platforms described above provide enhanced processing arrangements for use in the GA4GH Beacon Project, as well as in numerous other contexts involving use of beacons. For example, by using WWH as the computing paradigm for the Beacon Project, the resulting system becomes far more extensible than client-based arrangements and it can leverage all of the frameworks supported by YARN, allowing much more sophisticated computations and other analytics operations to be performed using data resources of beacon lit sites. Moreover, it allows the analytics to be performed in a more focused and distributed manner that relieves the client of having to communicate directly with each of a relatively large number of beacon lit sites.

The WWH catalog can be used in such embodiments to store metadata regarding the participants in a network of beacon lit sites, thereby allowing for query optimization based on particular beacon lit sites. For example, such metadata can be used to determine which of the beacon network participants should be part of the execution of a given query. The WWH catalog can allow for the creation of multiple distinct virtual beacon networks, each comprising a different subset of beacon network participants, with particular types of queries being sent only to certain virtual beacon networks.

It is to be appreciated that the particular types of system features and functionality as illustrated in the drawings and described above are exemplary only, and numerous other arrangements may be used in other embodiments.

It was noted above that portions of an information processing system as disclosed herein may be implemented using one or more processing platforms. Illustrative embodiments of such platforms will now be described in greater detail. These and other processing platforms may be used to implement at least portions of other information processing systems in other embodiments of the invention. A given such processing platform comprises at least one processing device comprising a processor coupled to a memory.

One illustrative embodiment of a processing platform that may be used to implement at least a portion of an information processing system comprises cloud infrastructure including virtual machines implemented using a hypervisor that runs on physical infrastructure. The cloud infrastructure further comprises sets of applications running on respective ones of the virtual machines under the control of the hypervisor. It is also possible to use multiple hypervisors each providing a set of virtual machines using at least one underlying physical machine. Different sets of virtual machines provided by one or more hypervisors may be utilized in configuring multiple instances of various components of the system.

These and other types of cloud infrastructure can be used to provide what is also referred to herein as a multi-tenant environment. One or more system components such as WWH nodes 102 and YARN clusters 104, or portions thereof, can be implemented as respective tenants of such a multi-tenant environment.

In some embodiments, the cloud infrastructure additionally or alternatively comprises a plurality of containers implemented using container host devices. For example, a given container of cloud infrastructure illustratively comprises a Docker container or other type of LXC. The containers may be associated with respective tenants of a multi-tenant environment of the system 100, although in other embodiments a given tenant can have multiple containers. The containers may be utilized to implement a variety of different types of functionality within the system 100. For example, containers can be used to implement respective cloud compute nodes or cloud storage nodes of a cloud computing and storage system. The compute nodes or storage nodes may be associated with respective cloud tenants of a multi-tenant environment of system 100. Containers may be used in combination with other virtualization infrastructure such as virtual machines implemented using a hypervisor.

Another illustrative embodiment of a processing platform that may be used to implement at least a portion of an information processing system comprises a plurality of processing devices which communicate with one another over at least one network. The network may comprise any type of network, including by way of example a global computer network such as the Internet, a WAN, a LAN, a satellite network, a telephone or cable network, a cellular network, a wireless network such as a WiFi or WiMAX network, or various portions or combinations of these and other types of networks.

As mentioned previously, some networks utilized in a given embodiment may comprise high-speed local networks in which associated processing devices communicate with one another utilizing PCIe cards of those devices, and networking protocols such as InfiniBand, Gigabit Ethernet or Fibre Channel.

Each processing device of the processing platform comprises a processor coupled to a memory. The processor may comprise a microprocessor, a microcontroller, an application-specific integrated circuit (ASIC), a field-programmable gate array (FPGA) or other type of processing circuitry, as well as portions or combinations of such circuitry elements. The memory may comprise random access memory (RAM), read-only memory (ROM) or other types of memory, in any combination. The memory and other memories disclosed herein should be viewed as illustrative examples of what are more generally referred to as "processor-readable storage media" storing executable program code of one or more software programs.

Articles of manufacture comprising such processor-readable storage media are considered embodiments of the present invention. A given such article of manufacture may comprise, for example, a storage array, a storage disk or an integrated circuit containing RAM, ROM or other electronic memory, or any of a wide variety of other types of computer program products. The term "article of manufacture" as used herein should be understood to exclude transitory, propagating signals.

Also included in the processing device is network interface circuitry, which is used to interface the processing device with the network and other system components, and may comprise conventional transceivers.

Again, these particular processing platforms are presented by way of example only, and other embodiments may include additional or alternative processing platforms, as well as numerous distinct processing platforms in any combination, with each such platform comprising one or more computers, servers, storage devices or other processing devices.

It should therefore be understood that in other embodiments different arrangements of additional or alternative elements may be used. At least a subset of these elements may be collectively implemented on a common processing platform, or each such element may be implemented on a separate processing platform.

Also, numerous other arrangements of computers, servers, storage devices or other components are possible in an information processing system as disclosed herein. Such components can communicate with other elements of the information processing system over any type of network or other communication media.

As indicated previously, components of an information processing system as disclosed herein can be implemented at least in part in the form of one or more software programs stored in memory and executed by a processor of a processing device. For example, at least portions of the functionality of a given YARN cluster or associated data processing node in a particular embodiment are illustratively implemented in the form of software running on one or more processing devices.

It should again be emphasized that the above-described embodiments of the invention are presented for purposes of illustration only. Many variations and other alternative embodiments may be used. For example, the disclosed techniques are applicable to a wide variety of other types of information processing systems, multi-cluster distributed data processing platforms, application frameworks, processing nodes, local and remote data resources and other components. Also, the particular configurations of system and device elements, associated processing operations and other functionality illustrated in the drawings can be varied in other embodiments. Moreover, the various assumptions made above in the course of describing the illustrative embodiments should also be viewed as exemplary rather than as requirements or limitations of the invention. Numerous other alternative embodiments within the scope of the appended claims will be readily apparent to those skilled in the art.

What is claimed is:

1. A method comprising: initiating a first application in a first one of a plurality of distributed processing nodes,
   wherein the plurality of distributed processing nodes comprise a plurality of clusters associated with respective data zones, each of the clusters being configured to perform processing operations utilizing local data resources locally accessible within its corresponding data zone;
   determining a plurality of data resources to be utilized by at least a portion of the first application, the plurality of data resources comprising at least one data resource that is not locally accessible within a first data zone associated with the first distributed processing node;
   responsive to initiation of the first application, identifying a plurality of beacon entities to be contacted to determine additional ones of the plurality of distributed processing nodes having associated data zones which include the at least one data resource not locally accessible within the first data zone associated with the first distributed processing node;
   accessing a distributed catalog service to identify at least a subset of the plurality of beacon entities to be contacted in conjunction with execution of at least a portion of the first application;
   for each of at least the subset of the identified beacon entities, initiating an additional application in an additional one of the plurality of distributed processing nodes, wherein each of the beacon entities is configured to perform processing operations associated with at least one of the first and one or more additional applications utilizing data resources locally accessible within a corresponding data zone;
   aggregating first and one or more additional processing results from the first and one or more additional processing nodes, wherein the aggregated processing results at least partially conceal identifying information of the first and one or more additional processing nodes providing the first and one or more additional processing results; and
   providing the aggregated processing results to a client;
   wherein the distributed catalog service is configured to store metadata characterizing the beacon entities;
   wherein the beacon entities are configured for organization, based at least in part on the stored metadata characterizing the beacon entities, into a plurality of virtual beacon networks for use in processing respective different types of beacon queries; and
   wherein the method is implemented by at least one processing device comprising a processor coupled to a memory.

2. The method of claim 1 wherein the plurality of beacon entities comprise respective participants in a beacon network.

3. The method of claim 1 wherein the plurality of beacon entities comprise respective geographically-distributed regional data centers each configured to perform analytics processing utilizing locally accessible data resources of a corresponding data zone.

4. The method of claim 1 wherein the beacon entities have respective activatable beacons.

5. The method of claim 1 wherein the distributed catalog service is distributed over the plurality of processing nodes with each such processing node having visibility of a corresponding distinct portion of the distributed catalog based on its locally accessible data resources.

6. The method of claim 1 wherein a given one of the applications initiated in a corresponding one of the processing nodes comprises an application master component.

7. The method of claim 6 wherein the application master component is configured to access a resolving interface of a distributed catalog service.

8. The method of claim 1 wherein at least one of the additional ones of the plurality of distributed processing nodes is selected based at least in part on proximity of said at least one additional processing node to a corresponding one of the beacon entities.

9. The method of claim 1 wherein aggregating processing results from the first and one or more additional processing nodes preserves at least one policy specifying:
  that processing results generated by a given one of the additional applications initiated in a given one of the additional processing nodes utilizing data resources locally accessible within a given data zone are permitted to be transmitted to the first processing node; and
  that the data resources locally accessible within the given data zone associated with the given additional processing node utilized to obtain the transmitted processing results are not permitted to be transmitted to the first processing node.

10. A computer program product comprising a non-transitory processor-readable storage medium having stored therein program code of one or more software programs; wherein the program code when executed by at least one processing device causes said at least one processing device:
  to initiate a first application in a first one of a plurality of distributed processing nodes, wherein the plurality of distributed processing nodes comprise a plurality of clusters associated with respective data zones, each of the clusters being configured to perform processing operations utilizing local data resources locally accessible within its corresponding data zone;
  to determine a plurality of data resources to be utilized by at least a portion of the first application; the plurality of data resources comprising at least one data resource that is not locally accessible within a first data zone associated with the first distributed processing node;
  responsive to initiation of the first application, to identify a plurality of beacon entities to be contacted to determine additional ones of the plurality of distributed processing nodes having associated data zones which include the at least one data resource not locally accessible within the first data zone associated with the first distributed processing node;
  to access a distributed catalog service to identify at least a subset of the plurality of beacon entities to be contacted in conjunction with execution of at least a portion of the first application;
  for each of at least the subset of the identified beacon entities, to initiate an additional application in an additional one of the plurality of distributed processing nodes, wherein each of the beacon entities is configured to perform processing operations associated with at least one of the first and one or more additional applications utilizing data resources locally accessible within a corresponding data zone;
  to aggregate first and one or more additional processing results from the first and one or more additional processing nodes, wherein the aggregated processing results at least partially conceal identifying information of the first and one or more additional processing nodes providing the first and one or more additional processing results; and
  to provide the aggregated processing results to a client;
  wherein the distributed catalog service is configured to store metadata characterizing the beacon entities; and
  wherein the beacon entities are configured for organization, based at least in part on the stored metadata characterizing the beacon entities, into a plurality of virtual beacon networks for use in processing respective different types of beacon queries.

11. The computer program product of claim 10 wherein the distributed catalog service is distributed over the plurality of processing nodes with each such processing node having visibility of a corresponding distinct portion of the distributed catalog based on its locally accessible data resources.

12. The computer program product of claim 10 wherein the plurality of beacon entities comprise respective participants in a beacon network.

13. The computer program product of claim 10 wherein the plurality of beacon entities comprise respective geographically-distributed regional data centers each configured to perform analytics processing utilizing locally accessible data resources of a corresponding data zone.

14. The computer program product of claim 10 wherein at least one of the additional ones of the plurality of distributed processing nodes is selected based at least in part on proximity of said at least one additional processing node to a corresponding one of the beacon entities.

15. An apparatus comprising:
  at least one processing device having a processor coupled to a memory;
  wherein said at least one processing device is configured:
  to initiate a first application in a first one of a plurality of distributed processing nodes, wherein the plurality of distributed processing nodes comprise a plurality of clusters associated with respective data zones, each of the clusters being configured to perform processing operations utilizing local data resources locally accessible within its corresponding data zone;
  to determine a plurality of data resources to be utilized by at least a portion of the first application, the plurality of data resources comprising at least one data resource that is not locally accessible within a first data zone associated with the first distributed processing node;
  responsive to initiation of the first application, to identify a plurality of beacon entities to be contacted to determine additional ones of the plurality of distributed processing nodes having associated data zones which include the at least one data resource not locally accessible within the first data zone associated with the first distributed processing node;
  to access a distributed catalog service to identify at least a subset of the plurality of beacon entities to be contacted in conjunction with execution of at least a portion of the first application;
  for each of at least the subset of the identified beacon entities, to initiate an additional application in an additional one of the plurality of distributed processing nodes, wherein each of the beacon entities is configured to perform processing operations associated with at least one of the first and one or more additional applications utilizing data resources locally accessible within a corresponding data zone;
  to aggregate first and one or more additional processing results from the first and one or more additional processing nodes, wherein the aggregated processing results at least partially conceal identifying information of the first and one or more additional processing nodes providing the first and one or more additional processing results; and to provide the aggregated processing results to a client, wherein the distributed catalog service is configured to store metadata characterizing the beacon entities; and wherein the beacon entities are configured for organization, based at least in part on the stored metadata characterizing the beacon entities, into a plurality of virtual beacon networks for use in processing respective different types of beacon queries.

16. The apparatus of claim 15 wherein the distributed catalog service is distributed over the plurality of processing nodes with each such processing node having visibility of a corresponding distinct portion of the distributed catalog based on its locally accessible data resources.

17. An information processing system comprising the plurality of distributed processing nodes of claim 15.

18. The apparatus of claim 15 wherein the plurality of beacon entities comprise respective participants in a beacon network.

19. The apparatus of claim 15 wherein the plurality of beacon entities comprise respective geographically-distributed regional data centers each configured to perform analytics processing utilizing locally accessible data resources of a corresponding data zone.

20. The apparatus of claim 15 wherein at least one of the additional ones of the plurality of distributed processing nodes is selected based at least in part on proximity of said at least one additional processing node to a corresponding one of the beacon entities.

* * * * *